US008702777B2

(12) United States Patent
Krolik et al.

(10) Patent No.: US 8,702,777 B2
(45) Date of Patent: *Apr. 22, 2014

(54) STEEP-TAPER FLARED STENTS AND APPARATUS AND METHODS FOR DELIVERING THEM

(75) Inventors: Jeffrey A. Krolik, Campbell, CA (US); Eliot Kim, Santa Clara, CA (US); James H. Dreher, Santa Monica, CA (US); Farhad Khosravi, Los Altos, CA (US)

(73) Assignee: Incept, LLC, Sunnyvale, CA (US)

( * ) Notice: Subject to any disclaimer, the term of this patent is extended or adjusted under 35 U.S.C. 154(b) by 967 days.

This patent is subject to a terminal disclaimer.

(21) Appl. No.: 11/466,445

(22) Filed: Aug. 22, 2006

(65) Prior Publication Data

US 2007/0073376 A1 Mar. 29, 2007

Related U.S. Application Data

(60) Provisional application No. 60/710,521, filed on Aug. 22, 2005, provisional application No. 60/727,703, filed on Oct. 17, 2005, provisional application No. 60/757,600, filed on Jan. 9, 2006, provisional application No. 60/743,880, filed on Mar. 28, 2006, provisional application No. 60/745,177, filed on Apr. 19, 2006.

(51) Int. Cl.
*A61F 2/06* (2013.01)
(52) U.S. Cl.
USPC .......... 623/1.11; 623/1.15; 606/194; 606/198
(58) Field of Classification Search
USPC ............... 623/1.1, 1.11, 1.12, 1.18, 1.19, 1.2, 623/1.13, 1.15, 1.16, 1.23, 1.31; 606/198, 606/194, 191, 195
See application file for complete search history.

(56) References Cited

U.S. PATENT DOCUMENTS 4,921,483 A 5/1990 Wijay et al.
4,950,227 A 8/1990 Savin et al.
(Continued)

FOREIGN PATENT DOCUMENTS

EP 0876805 A2 11/1998
EP 1364676 11/2003
(Continued)

OTHER PUBLICATIONS

PCT International Search Report for PCT/US2006/032938, Applicant: Incept, LLC, Forms PCT/ISA/220 and PCT/ISA/210, dated Jan. 4, 2007, 7 pages.

(Continued)

*Primary Examiner* — Gary Jackson
*Assistant Examiner* — Katrina Stransky
(74) *Attorney, Agent, or Firm* — William A. English; Vista IP Law Group LLP

(57) ABSTRACT

A stent includes a first flaring portion including first and second sets of cells that flare outwardly when the stent is expanded from a contracted to a flared condition, and a second main portion connected to the first flaring portion. During use, the stent is introduced into a main vessel in the contracted condition and positioned with the first portion adjacent an ostium. The first portion is flared, causing first struts of the first set of cells to move from an axial towards a radial and partial circumferential orientation and causing second struts of the second set of cells to move from an axial towards a radial orientation. The second portion resists expansion when the first portion is flared. The stent is expanded further such that the second portion expands within the branch body lumen, and the first and second struts move towards a more circumferential orientation.

13 Claims, 42 Drawing Sheets

(56) References Cited

U.S. PATENT DOCUMENTS

| | | | |
|---|---|---|---|
| 5,409,495 A | 4/1995 | Osborn | |
| 5,540,712 A | 7/1996 | Kleshinski et al. | |
| 5,607,444 A | 3/1997 | Lam | |
| 5,609,605 A | 3/1997 | Marshall et al. | |
| 5,632,762 A | 5/1997 | Myler | |
| 5,667,486 A | 9/1997 | Mikulich et al. | |
| 5,716,393 A | 2/1998 | Lindenberg et al. | |
| 5,741,333 A | 4/1998 | Frid | |
| 5,749,890 A | 5/1998 | Shaknovich | |
| 5,755,769 A | 5/1998 | Richard et al. | |
| 5,902,317 A | 5/1999 | Kleshinski et al. | |
| 6,096,071 A | 8/2000 | Yadav | |
| 6,210,431 B1 | 4/2001 | Power | |
| 6,234,996 B1* | 5/2001 | Bagaoisan et al. | 604/97.01 |
| 6,409,755 B1 | 6/2002 | Vrba | |
| 6,428,569 B1* | 8/2002 | Brown | 623/1.15 |
| 6,585,758 B1* | 7/2003 | Chouinard et al. | 623/1.16 |
| 6,821,295 B1 | 11/2004 | Farrar | |
| 7,105,015 B2 | 9/2006 | Goshgarian | |
| 7,670,367 B1* | 3/2010 | Chouinard et al. | 623/1.15 |
| 2001/0007954 A1* | 7/2001 | Shaolian et al. | 623/1.11 |
| 2002/0077691 A1 | 6/2002 | Nachtigall | |
| 2002/0091434 A1 | 7/2002 | Chambers | |
| 2002/0161392 A1* | 10/2002 | Dubrul | 606/200 |
| 2002/0169500 A1* | 11/2002 | Jang | 623/1.16 |
| 2003/0083734 A1* | 5/2003 | Friedrich et al. | 623/1.15 |
| 2003/0236563 A1* | 12/2003 | Fifer | 623/1.11 |
| 2004/0093058 A1 | 5/2004 | Cottone | |
| 2004/0096606 A1* | 5/2004 | Lee et al. | 428/35.2 |
| 2004/0102838 A1 | 5/2004 | Killion | |
| 2004/0117008 A1* | 6/2004 | Wnendt et al. | 623/1.46 |
| 2004/0181272 A1 | 9/2004 | Chambers | |
| 2004/0243216 A1* | 12/2004 | Gregorich | 623/1.15 |
| 2004/0254627 A1 | 12/2004 | Thompson et al. | |
| 2005/0049678 A1 | 3/2005 | Cocks et al. | |
| 2005/0049680 A1 | 3/2005 | Fischell et al. | |
| 2005/0101968 A1 | 5/2005 | Dadourian | |
| 2005/0131519 A1* | 6/2005 | Hartley | 623/1.13 |
| 2005/0149166 A1* | 7/2005 | Schaeffer et al. | 623/1.13 |
| 2005/0154447 A1 | 7/2005 | Goshgarian | |
| 2005/0177221 A1* | 8/2005 | Mustapha | 623/1.11 |
| 2005/0288769 A1 | 12/2005 | Globerman | |
| 2006/0224233 A1 | 10/2006 | Grimfeld | |
| 2006/0265041 A1* | 11/2006 | Sanati et al. | 623/1.11 |
| 2007/0021819 A1 | 1/2007 | Krolik | |
| 2007/0021828 A1 | 1/2007 | Krolik | |
| 2007/0038283 A1 | 2/2007 | Mustapha | |
| 2007/0055358 A1 | 3/2007 | Krolik | |
| 2007/0067011 A1 | 3/2007 | Krolik | |
| 2007/0073388 A1 | 3/2007 | Krolik | |
| 2007/0088425 A1 | 4/2007 | Schaeffer | |
| 2008/0208307 A1 | 8/2008 | Ben Muvhar et al. | |
| 2008/0221655 A1 | 9/2008 | Miller | |
| 2008/0243233 A1 | 10/2008 | Ben Muvhar et al. | |

FOREIGN PATENT DOCUMENTS

| | | |
|---|---|---|
| EP | 1512381 A2 | 3/2005 |
| WO | 9717101 A | 5/1997 |
| WO | 9936015 | 7/1999 |
| WO | 2005041810 | 5/2005 |
| WO | WO 2005099629 A1 * | 10/2005 |
| WO | 2006085304 | 8/2006 |

OTHER PUBLICATIONS

PCT Written Opinion for PCT/US2006/032938, Applicant: Incept, LLC, Forms PCT/ISA/237, dated Jan. 4, 2007, 7 pages.

Office Action for US Patent Publication No. 2006/0265041 (NCPT-003), Mar. 20, 2008, 88 pages.

Office Action for US Patent Publication No. 2007/0067011 (NCPT-017), Mar. 27, 2008, 20 pages.

* cited by examiner

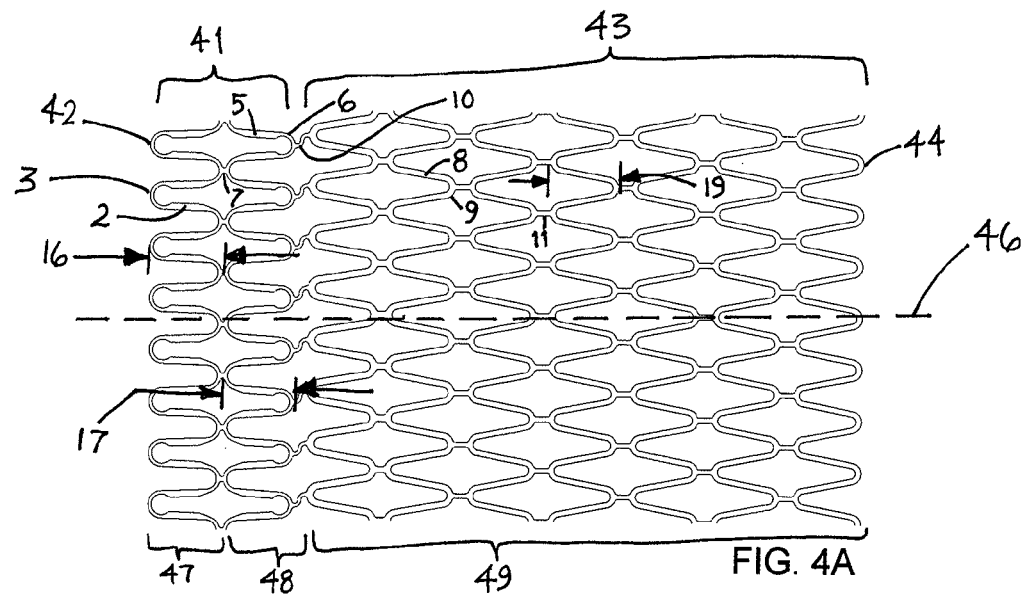
FIG. 4A
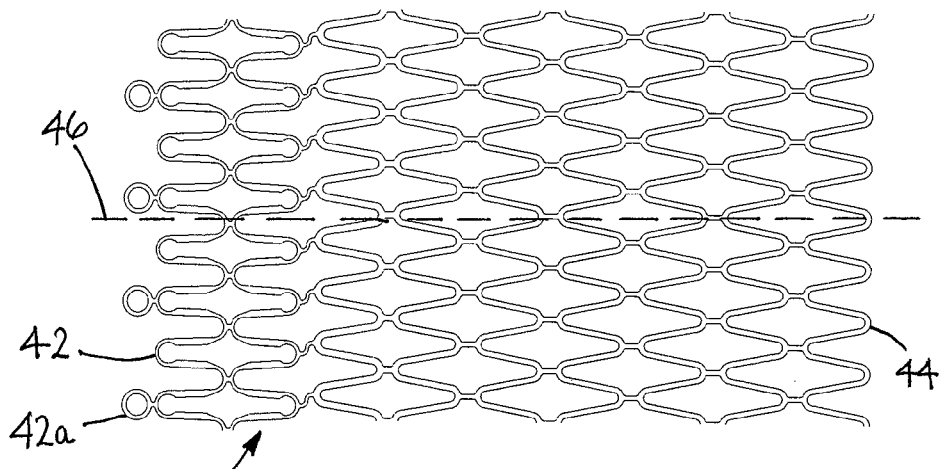
FIG. 4B
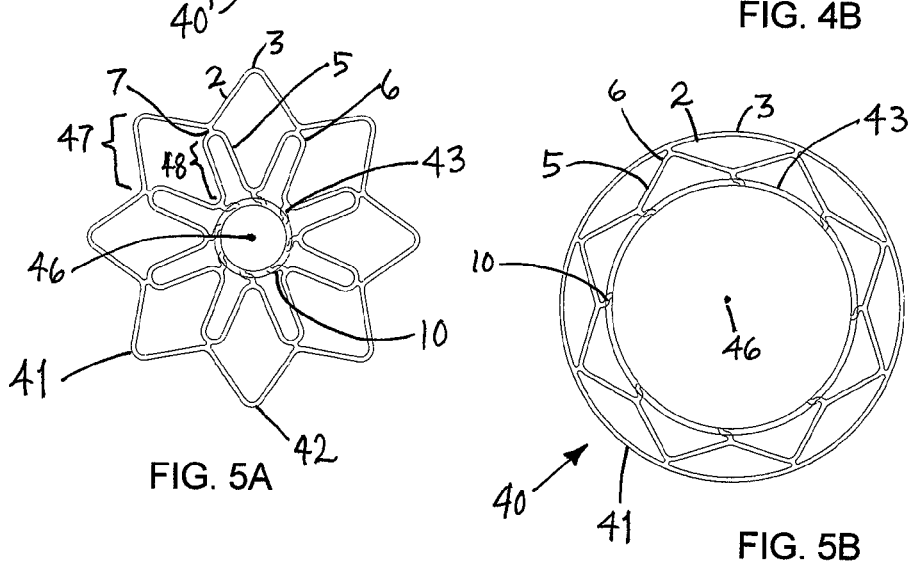
FIG. 5A
FIG. 5B

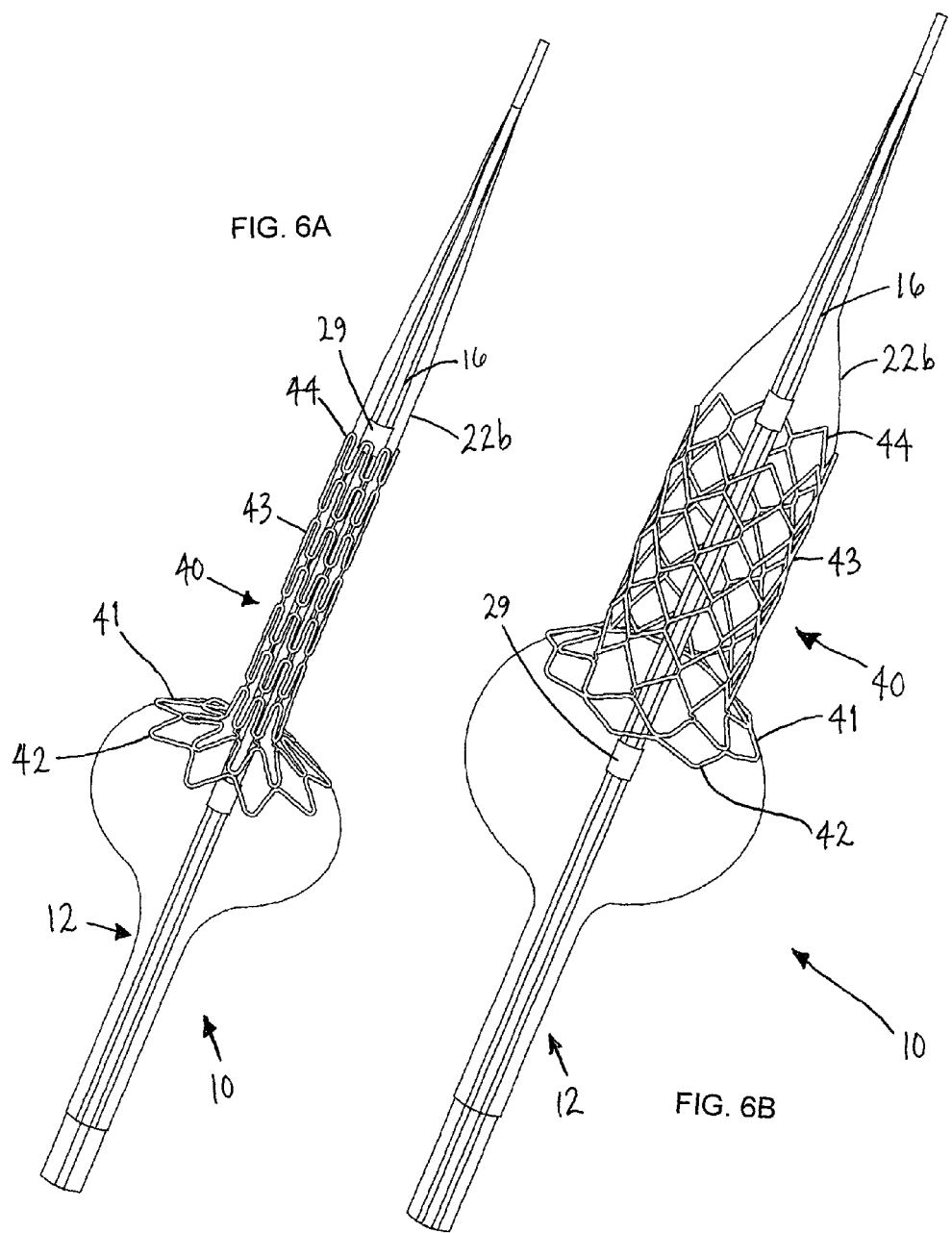

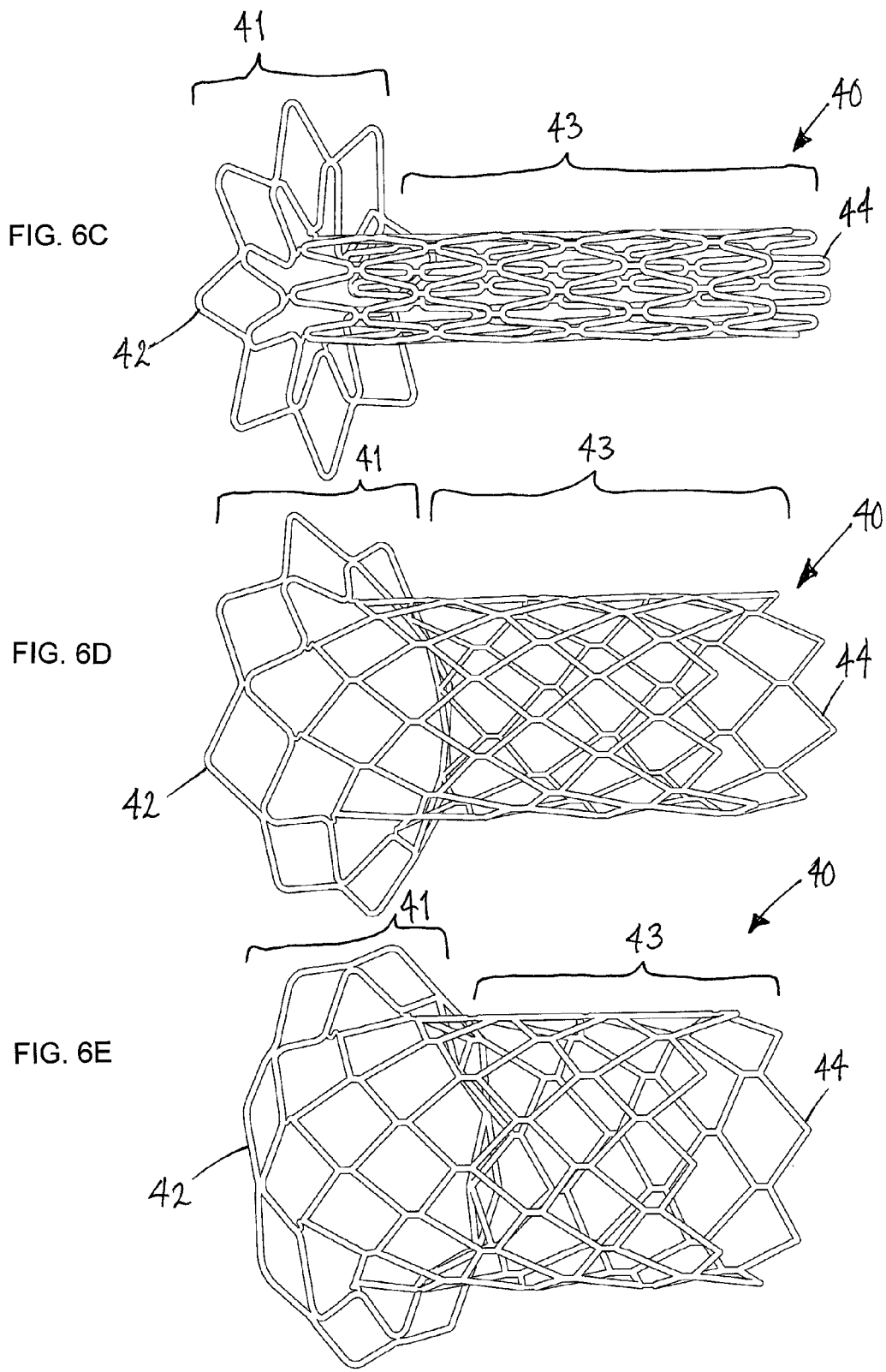

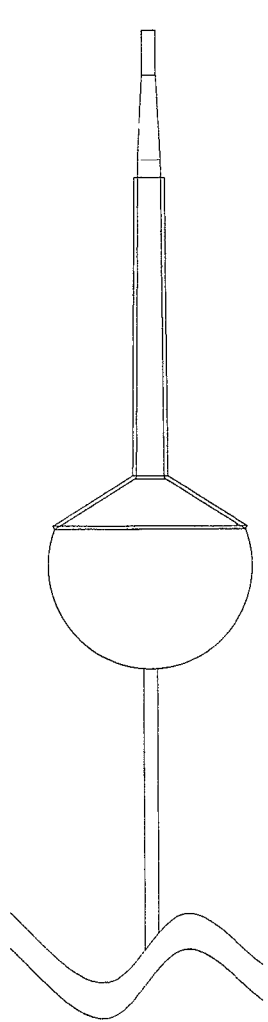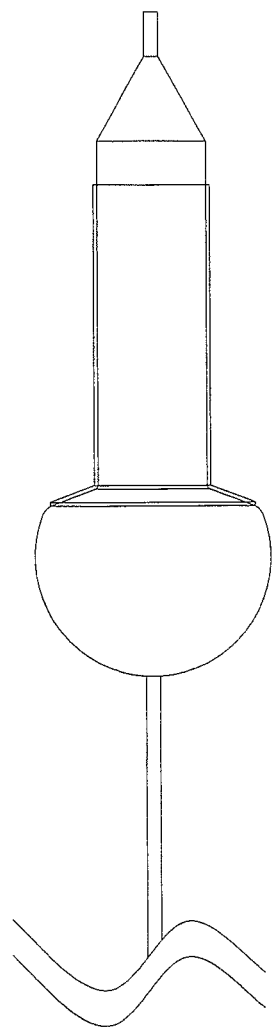

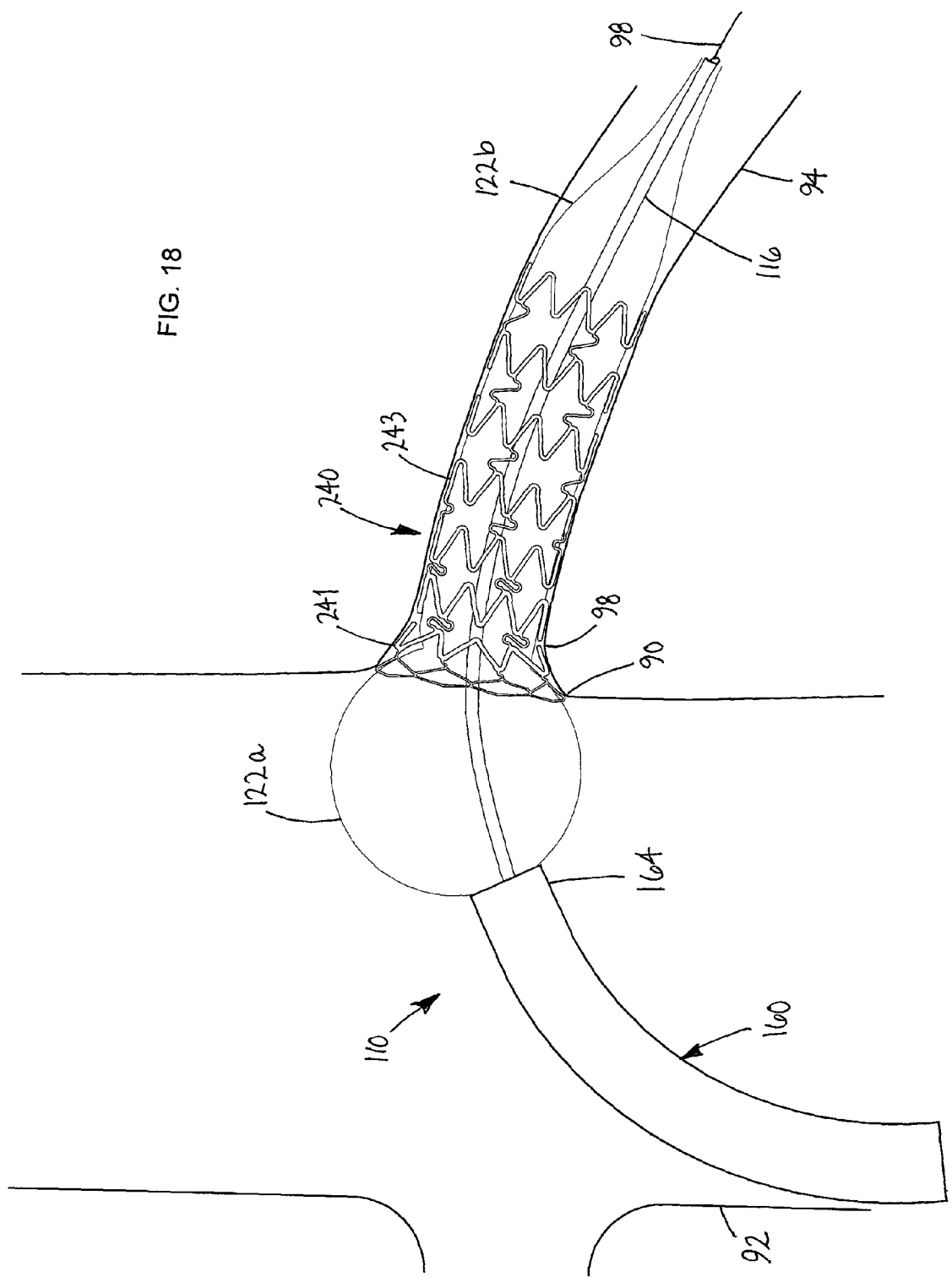

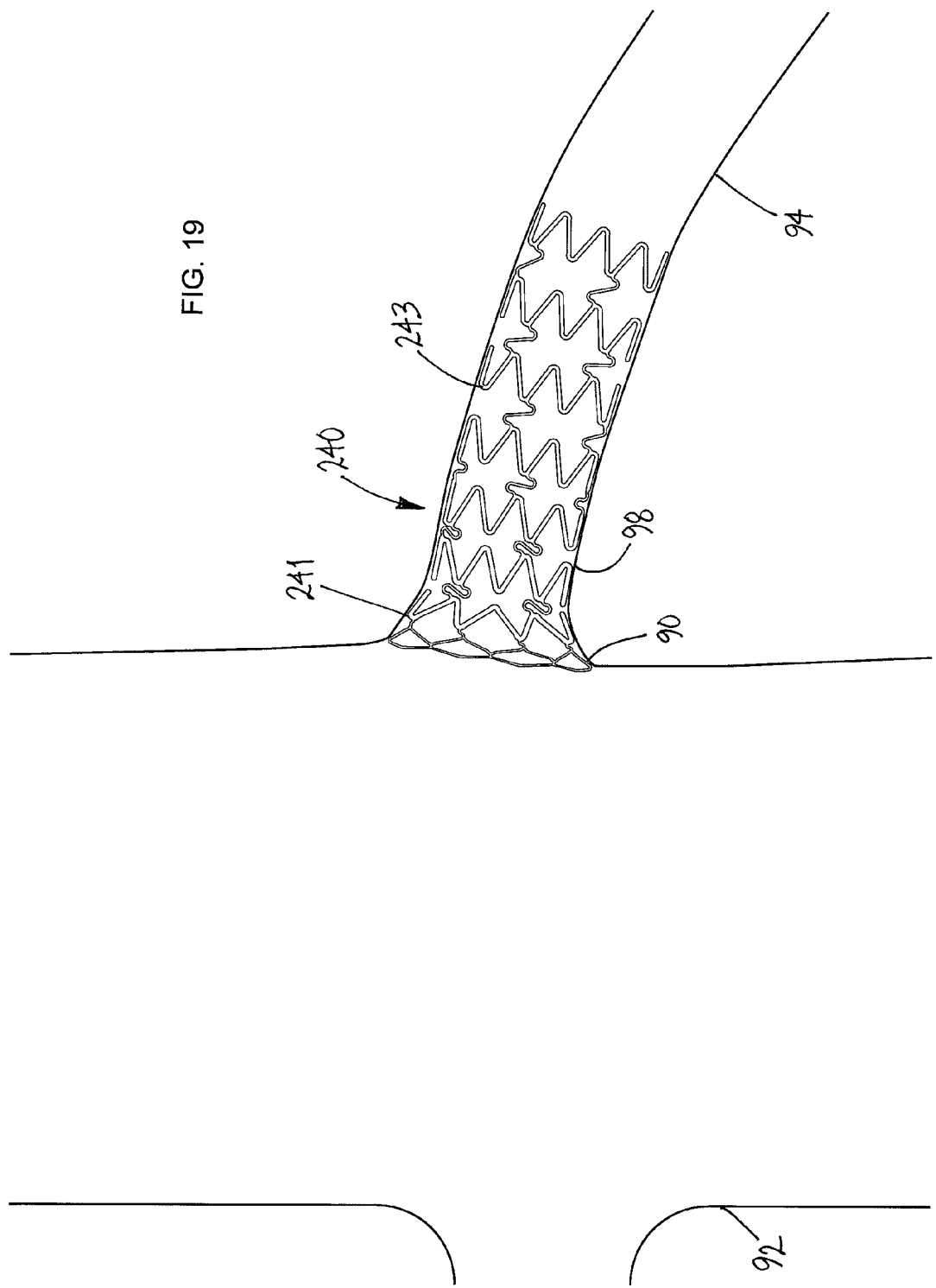

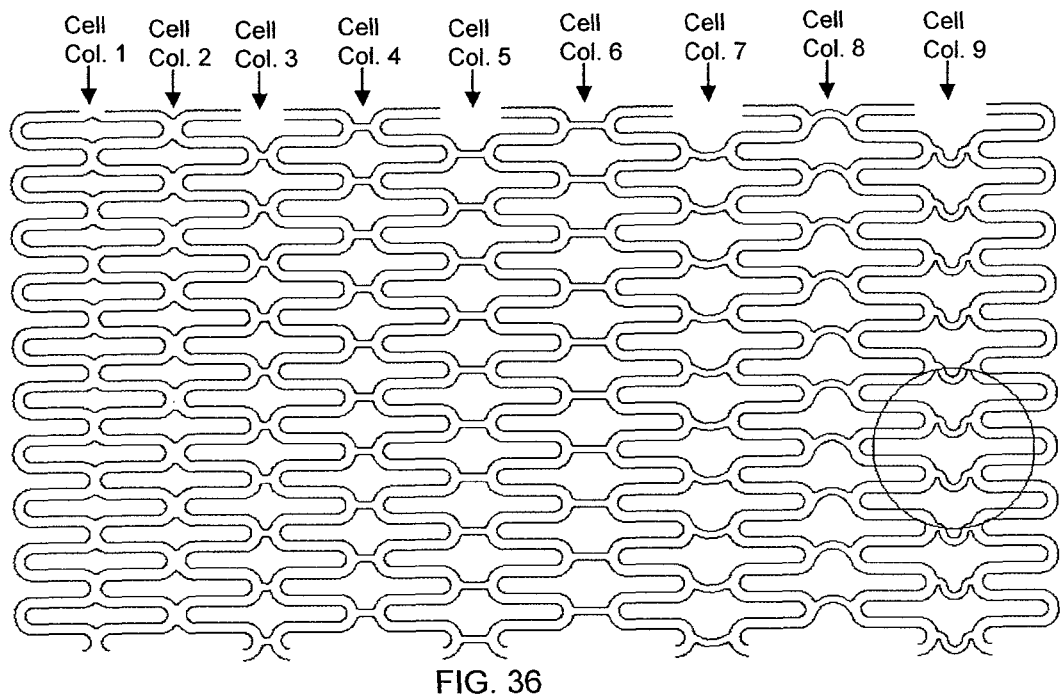
FIG. 36
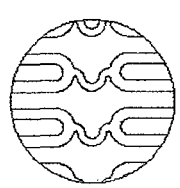 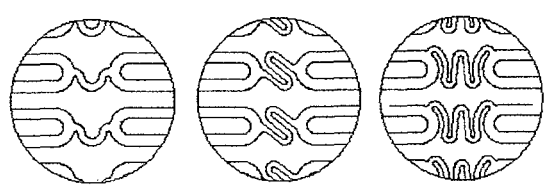
FIG. 36A    FIG. 36B    FIG. 36C

STEEP-TAPER FLARED STENTS AND APPARATUS AND METHODS FOR DELIVERING THEM

This application claims benefit of provisional applications Ser. Nos. 60/710,521, filed Aug. 22, 2005, 60/727,703, filed Oct. 17, 2005, 60/757,600, filed Jan. 9, 2006, 60/743,880, filed Mar. 28, 2006, and 60/745,177, filed Apr. 19, 2006, the entire disclosures of which are expressly incorporated by reference herein.

FIELD OF THE INVENTION

The present invention relates generally to endoluminal prostheses or "stents," and, more particularly, to flared stents, and to apparatus and methods for delivering such stents into an ostium of a blood vessel or other body lumen.

BACKGROUND

Tubular endoprosthesis or "stents" have been suggested for dilating or otherwise treating stenoses, occlusions, and/or other lesions within a patient's vasculature or other body lumens. For example, a self-expanding stent may be maintained on a catheter in a contracted condition, e.g., by an overlying sheath or other constraint, and delivered into a target location, e.g., a stenosis within a blood vessel or other body lumen. When the stent is positioned at the target location, the constraint may be removed, whereupon the stent may automatically expand to dilate or otherwise line the vessel at the target location. Alternatively, a balloon-expandable stent may be carried on a catheter, e.g., crimped or otherwise secured over a balloon, in a contracted condition. When the stent is positioned at the target location, the balloon may be inflated to expand the stent and dilate the vessel.

Sometimes, a stenosis or other lesion may occur at an ostium or bifurcation, i.e., where a branch vessel extends from a main vessel or trunk. For example, such a lesion may form within a coronary artery immediately adjacent the aortic root. U.S. Pat. No. 5,749,890 to Shaknovich discloses a stent delivery assembly for placing a stent in an ostial lesion. U.S. Pat. No. 5,632,762 to Myler discloses a tapered balloon on a catheter for positioning a stent within an ostium. U.S. Pat. No. 5,607,444 to Lam discloses an expandable ostial stent including a tubular body and a deformable flaring portion. Published application US 2002/0077691 to Nachtigall discloses a delivery system that includes a sheath for holding a stent in a compressed state during delivery and a retainer that holds a deployable stop in an undeployed position while the delivery system is advanced to a desired location.

FIGS. 1, 2, and 3 show attempts to deploy flared stents within various ostia having different shapes and/or sizes, and some of the risks of improper deployment.

Accordingly, flared stents and apparatus and methods for delivering stents within an ostium would be useful.

SUMMARY OF THE INVENTION

The present invention is directed to endoluminal prostheses or "stents," and, more particularly, to flared stents, and to apparatus and methods for delivering such stents into an ostium of a blood vessel or other body lumen.

In accordance with one embodiment, a stent is provided that includes a tubular member including first and second ends defining a longitudinal axis therebetween and a plurality of cells disposed between the first and second ends. Generally, the stent includes a first end portion configured to flare outwardly when the stent is expanded from the contracted condition to an intermediate flared condition, and a second portion adjacent the first portion configured to expand when the stent is expanded from the flared condition to a fully deployed condition. The second portion may be connected to the first end portion by a plurality of flexible connectors, which may facilitate the first end portion flaring outwardly.

In accordance with another embodiment, a stent is provided that includes a tubular member including first and second ends defining a longitudinal axis therebetween and a plurality of cells disposed between the first and second ends, the tubular member being expandable from a contracted condition to a fully expanded or deployed condition through an intermediate flared condition. The stent may include a first end portion configured to flare outwardly when the stent is expanded from the contracted condition to the flared condition, a second portion adjacent the first portion, and a plurality of flexible connectors connecting the second portion to the first end portion.

In an exemplary embodiment, the first end portion may include a first set of cells at the first end and a second set of cells adjacent the first set of cells, the second set of cells including struts or other segments extending substantially axially in the contracted condition. The connectors may connect the second set of cells to the second portion such that the connectors bend to accommodate the struts of the second set of cells assuming a generally radially outward orientation in the flared condition. In addition or alternatively, the first set of cells may include a plurality of struts or other segments extending substantially axially in the contracted condition. The axial segments of the first set of cells may assume a generally circumferential orientation in the fully deployed condition.

In accordance with still another embodiment, a stent is provided that includes a tubular member including first and second ends defining a longitudinal axis therebetween and a plurality of cells disposed between the first and second ends. Generally, the stent includes a first flaring portion at the first end configured to flare outwardly when the stent is expanded from the contracted condition to an intermediate flared condition, and a second main portion adjacent the flaring portion configured to expand when the stent is expanded from the flared condition to a fully deployed condition. The main portion may include a proximal portion immediately adjacent the flaring portion and a distal portion extending between the proximal portion and the second end.

In one embodiment, the proximal portion may have a greater radial strength than the distal portion. In addition or alternatively, the distal portion may have a radial strength greater than the flaring portion. Thus, in an exemplary embodiment, the flaring portion may be more easily expandable than the main portion, and the proximal portion of the main portion may have the greatest radial strength of the stent, e.g., to facilitate maintaining an ostium dilated after implanting the stent.

In accordance with yet another embodiment, an apparatus is provided for treating an ostium communicating between a main body lumen and a branch body lumen. Generally, the apparatus includes an elongate member including a proximal end, a distal end sized for introduction into at least one of the main body lumen and the branch body lumen, and an expandable member on the distal end, the expandable member being expandable from a first collapsed configuration to a second flared configuration and to a third expanded configuration. A stent may be provided on the distal end over the expandable member that includes a first end portion and a second portion connected to the first end portion by a plurality of flexible connectors.

The stent and/or expandable member may be configured such that, when the expandable member is expanded to the second configuration, the first end portion of the stent is expanded to a flared condition, and when the expandable member is expanded to the third configuration, the second portion is expanded radially outwardly and the first end portion is further expanded radially outwardly. In one embodiment, the expandable member may include a first balloon underlying the first end portion of the stent and a second balloon underlying at least the second portion of the stent. The first balloon may be expandable independent of the second balloon, e.g., such that the second flared configuration is defined by expansion of the first balloon.

In accordance with yet another embodiment, an apparatus is provided for treating an ostium communicating between a main body lumen and a branch body lumen. Generally, the apparatus includes an elongate member including a proximal end, a distal end sized for introduction into at least one of the main body lumen and the branch body lumen, and proximal and distal balloons on the distal end. The balloons may be expandable from a collapsed configuration to an expanded configuration, e.g., such that the distal balloon adopts a substantially cylindrical shape in the expanded configuration and the proximal balloon adopts a substantially spherical shape in the expanded configuration.

The balloons may be independently expandable and/or deflatable from one another. In addition or alternatively, the proximal balloon may be compliant or semi-compliant and the distal balloon may be substantially non-compliant.

A stent may be provided on the distal end at least partially over the balloons that includes a first flaring portion and a second main portion. Optionally, the second main portion may include a more rigid proximal main portion adjacent the flaring portion and a less rigid distal main portion. In one embodiment, the stent may be provided on the distal end of the elongate member such that the first flaring portion and at least a portion of the proximal main portion overly the proximal balloon and the distal main portion overlies the distal balloon.

In accordance with still another embodiment, a method is provided for expanding a stent. A stent may be provided on an expandable member, the stent including first and second ends, a first end portion including a first set of cells at the first end and a second set of cells adjacent the first set of cells, and a second portion connected to the first end portion. The expandable member may be expanded from a first collapsed configuration to a second flared configuration to flare the first end portion, thereby causing first struts of the first set of cells to move from a substantially axial orientation towards a radial and partial circumferential orientation and causing second struts of the second set of cells to move from a substantially axial orientation towards a radial orientation. The expandable member may then be expanded from the second configuration to a third enlarged condition, thereby causing the first and second struts to move towards a more circumferential orientation. Optionally, the second set of cells may be coupled to the second portion of the stent by a plurality of flexible connectors, the connectors accommodating radial and/or circumferential movement of the second struts.

In accordance with yet another embodiment, a method is provided for delivering a stent within an ostium communicating between a main body lumen and a branch body lumen. The stent may include first and second ends, a first end portion including a first set of cells at the first end and a second set of cells adjacent the first set of cells, and a second portion connected to the first end portion.

Initially, the stent may be introduced into the main body lumen with the stent in a contracted condition, and positioned such that the first end portion is disposed adjacent the ostium and the second portion is disposed within the branch body lumen. The first end portion may be flared, thereby causing first struts of the first set of cells to move from a substantially axial orientation towards a radial and partial circumferential orientation and causing second struts of the second set of cells to move from a substantially axial orientation towards a radial orientation. Optionally, the stent may be further positioned, the flared first end portion facilitating positioning relative to the ostium. The stent may then be expanded such that the second portion expands within the branch body lumen, and the first and second struts move towards a more circumferential orientation, thereby securing the stent relative to the ostium.

In accordance with another embodiment, a method is provided for expanding a stent that includes providing a stent on one or more expandable members, the stent including first and second ends, a first portion and a second portion connected to the first flaring portion. An expandable member is expanded to flare the first portion, the second portion having sufficient stiffness to resist expansion when the first portion is flared. An expandable member is expanded to expand the second portion to an enlarged condition, thereby causing the first portion to expand further. In one embodiment, the second portion includes a distal main portion and a proximal main portion connecting the first portion to the distal main portion. The proximal main portion may include a stiffness, radial strength, and/or other characteristics such that the proximal main portion resists expansion when the first flaring portion is flared.

In accordance with yet another embodiment, a method is provided for delivering a stent within an ostium communicating between a main body lumen and a branch body lumen, the stent including a first flaring portion, and a second main portion including a distal main portion and a proximal main portion connecting the distal main portion to the first flaring portion. The stent is introduced into the main body lumen stent in a contracted condition. The first flaring portion is expanded to a flared configuration, e.g., by expanding a first expandable member. The proximal main portion, which may partially overly the first expandable member, may resist expansion when the first flaring portion is flared by the first expandable member. The stent is expanded further, e.g., by expanding a second expandable member, such that the second main portion expands within the branch body lumen, and the first flaring portion expands further adjacent the ostium. The proximal main portion may have a greater radial strength than the distal main portion, thereby providing enhanced support of the ostium than more distally within the branch body lumen.

In accordance with still another embodiment, a stent is provided that includes a tubular member including first and second ends defining a longitudinal axis therebetween and a plurality of cells disposed between the first and second ends, the tubular member being expandable from a contracted condition to an enlarged condition. Generally, the stent includes a first flaring portion configured to flare outwardly when the stent is expanded from the contracted condition to the enlarged condition, and a second main portion adjacent the first flaring portion.

The main portion may include a plurality of bands of cells spaced apart axially from one another with adjacent bands of cells connected to one another. In an exemplary embodiment, adjacent bands of cells may be intermittently or otherwise connected, e.g., by links, such that the main portion is axially compressible when the stent is expanded.

In accordance with yet another embodiment, a method is provided for delivering a stent within an ostium communicating between a main body lumen and a branch body lumen. Generally, the stent may include first and second ends, a first flaring portion, and a second main portion adjacent the flaring portion. The stent may be introduced into the main body lumen with the stent in a contracted condition, and the flaring portion may be flared to a first expanded size. The stent may be advanced at least partially into the ostium with the flaring portion flared, and the stent may be further expanded.

For example, the main portion may be expanded within the branch body lumen, e.g., to dilate a stenosis or other lesion adjacent to or within the ostium and/or branch, and/or to anchor the main portion relative to the branch. The flaring portion may then be expanded further, e.g., to a second expanded size greater than the first expanded size, e.g., to enhance seating of the stent relative to the ostium. The main portion may foreshorten, e.g., when the main portion is expanded within the branch and/or when the flaring portion is expanded to the second expanded size. This axial compression of the main portion may enhance seating of the stent and/or may enhance support within lesion and/or ostium.

In accordance with still another embodiment, a stent is provided that includes a tubular member including first and second ends defining a longitudinal axis therebetween, and a plurality of cells disposed between the first and second ends. The tubular member may be expandable from a contracted condition to an enlarged condition, the first end having a larger cross-section than the second end in the enlarged condition. In one embodiment, the tubular member may include a first set of cells disposed at the first end, and a second set of cells disposed adjacent the first set of cells, the first and second sets of cells having first and second axial lengths, respectively, in the contracted condition, the first axial length being substantially shorter than the second axial length.

In accordance with yet another embodiment, a stent is provided that is configured to be expanded from a contracted condition to an enlarged condition, the stent including a first end portion configured to flare outwardly when the stent is expanded from the contracted condition to the enlarged condition; a second intermediate portion adjacent the first portion; and a third end portion adjacent the second portion opposite the first portion, wherein at least two of the first, second, and third portions have different mechanical properties.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 4A is a top view of a cell pattern for a stent having a flaring portion on a first end.

FIG. 4B is a top view of another cell pattern for a stent having a flaring portion on a first end and including radiopaque markers on the first end.

FIGS. 5A and 5B are ends views of the first end of the stent of FIG. 4A, showing the stent in a flared condition and a fully expanded condition, respectively.

FIGS. 6A and 6B are perspective views of a stent delivery catheter including a stent over a balloon thereon, showing the stent in a flared condition and a fully expanded condition, respectively.

FIG. 6C is a perspective view of a stent including a first end portion and a second portion, the first end portion being flared while the second portion remains in a contracted condition.

FIGS. 6D and 6E are perspective views of the stent of FIG. 6C, showing the stent fully expanded to be received in relatively large and small vessels, respectively.

FIGS. 10A and 10B are side views of the distal end of the stent delivery catheter of FIG. 9, showing the proximal balloon inflated to flare the first flaring portion of the stent and showing the distal balloon inflated to expand the second main portion of the stent, respectively.

FIGS. 13-19 are perspective views of an ostium communicating between a main vessel and a branch vessel, showing a method for delivering the stent of FIG. 12.

FIGS. 33-36 are top views of exemplary cell patterns for stents having variable properties along their lengths.

FIGS. 36A-36C are details showing alternative embodiments of links for connecting adjacent bands of cells in a stent.

DETAILED DESCRIPTION OF THE EXEMPLARY EMBODIMENTS

Figure 1A:
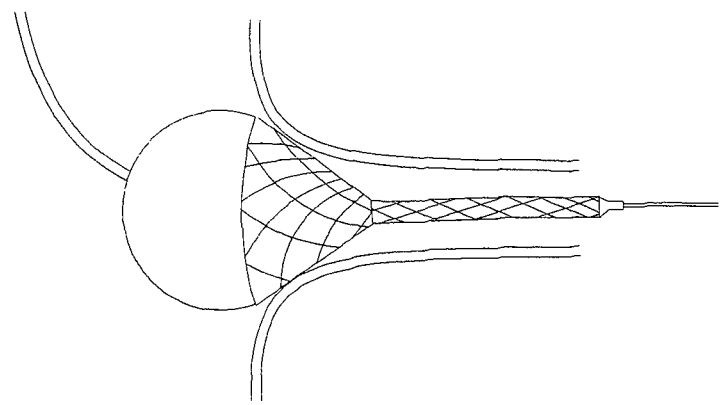
FIGS. 1A-1C are cross-sectional side views of different configurations of an ostium, showing a flared stent being deployed therein.
Figure 1B:
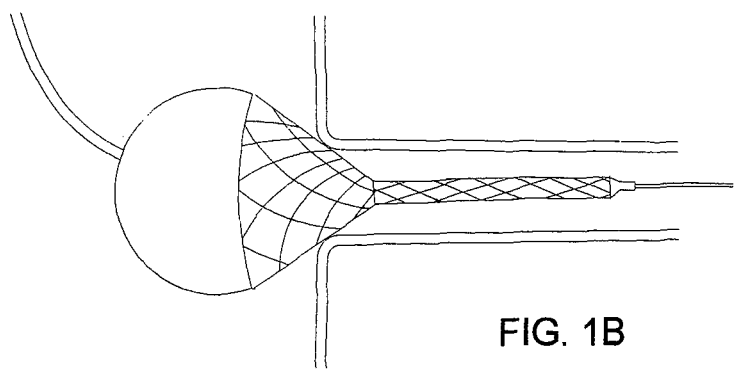
Figure 1C:
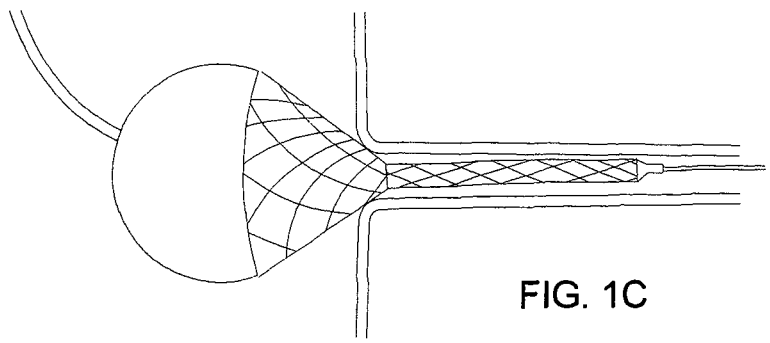
Figure 2A:
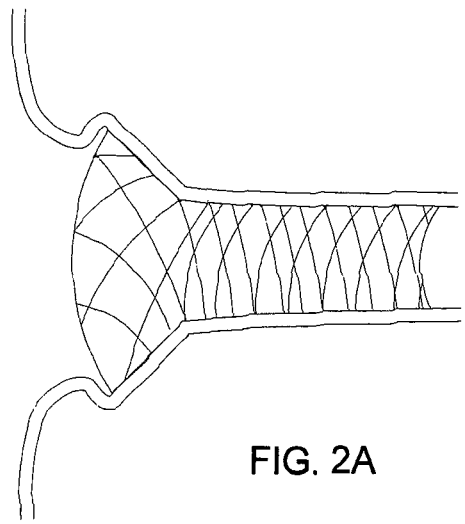
FIGS. 2A and 2B are cross-sectional side views of additional configurations of an ostium, showing a flared stent being deployed therein.
Figure 2B:
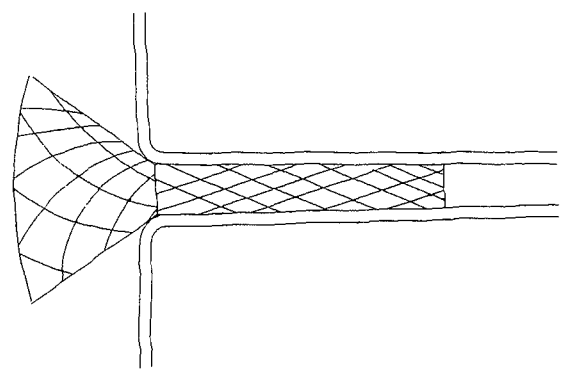
Figure 3A:
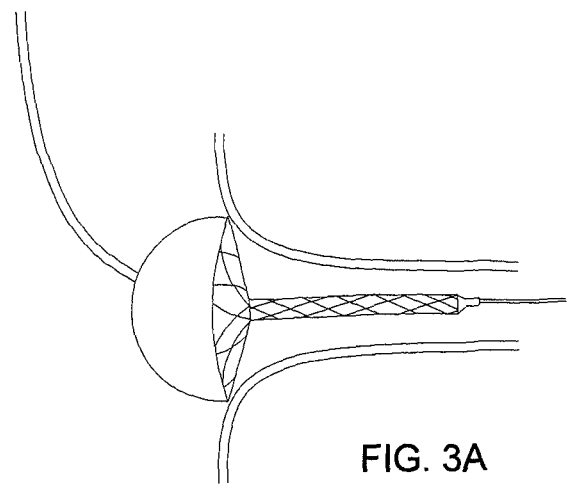
FIGS. 3A-3C are cross-sectional side views of still additional configurations of an ostium, showing a flared stent being deployed therein.
Figure 3B:
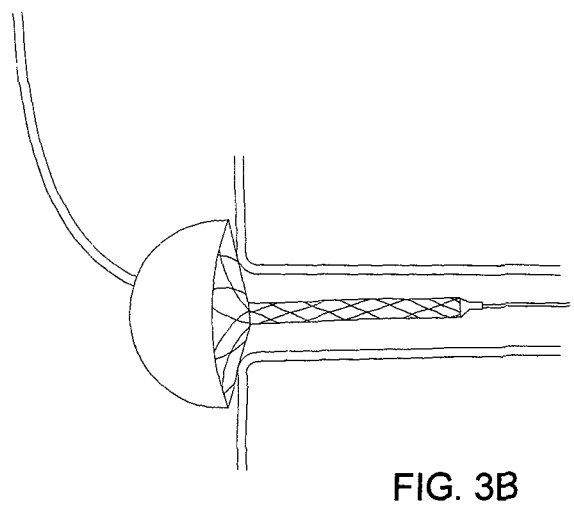
Figure 3C:
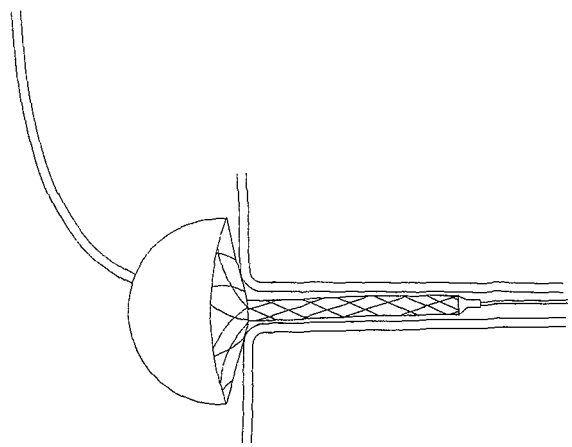

Turning to the drawings, FIGS. 4-6 show exemplary embodiments of a stent 40 that includes a generally cylindrical tubular member including a proximal or first end 42 and a distal or second end 44 defining a longitudinal axis 46 therebetween. The stent 40 is generally radially expandable from a contracted or delivery condition (not shown), to a flared condition (e.g., as shown in FIGS. 5A, 6A, and 6C), and to an enlarged or fully deployed condition (e.g., as shown in FIGS. 5B, and 6B-6E). For example, the stent 40 may include a first end portion 41 at the first end 42 and a second portion 43 adjacent the first end portion 41, and a plurality of connectors 10 connecting the second portion 43 to the first end portion 41.

In an exemplary embodiment, the stent 40 may include a plurality of annular bands of cells 47-49 disposed between the proximal and distal ends 42, 44. Each band of cells 47-49 may be defined by a plurality of struts or other elements extending axially along and/or circumferentially around the stent 40, e.g., in a zigzag or serpentine pattern, thereby defining an open-cell structure. Adjacent bands of cells may be connected to one another, directly or via links or other elements.

For example, with particular reference to FIG. 4A, the stent 40 may include first and second bands of cells 47, 48 defining the first end portion 41 of the stent 40. The first band of cells 47 at the first end 42 generally includes a zigzag or serpentine pattern defined by a plurality of axial elements 2 connected alternately by curved elements 3 extending about the circumference of the stent 40. The axial elements 2 may be substantially straight, e.g., extending substantially parallel to the longitudinal axis in the contracted condition, as shown in FIG. 4A. Alternatively, the axial elements 2 may include more complicated geometry, e.g., including one or more curves or bends, thereby including both an axial component and a circumferential component (not shown). Generally, the first band of cells 47 includes a first axial length 16 substantially parallel to the longitudinal axis 46, which may be defined at least partially by a length of the axial elements 2, e.g., depending upon whether the axial elements 2 extend substantially parallel to the longitudinal axis or extend at an angle relative to the longitudinal axis (i.e., diagonally or circumferentially).

The second band of cells 48 adjacent the first band of cells 47 also generally includes a zigzag or serpentine pattern defined by axial elements 5 connected alternately by curved elements 6 extending about the circumference of the stent 40. As shown, the second band of cells 48 may define an axial length 17, which may be substantially similar to the first band of cells 47. For example, the axial elements 2, 5 may have substantially the same length and the curved elements 3, 6 may have substantially the same radius of curvature.

As shown, the axial elements 2, 5 have a thickness and/or width that is greater than the curved elements 3, 6. Thus, the yield strength of the curved elements 3, 6 may be less than the axial elements 2, 5, which may facilitate radial flaring of the first end portion 41, as explained further below.

In addition, the second band of cells 48 is connected to the first band of cells 47 by one or more struts or other connectors 7. Generally, the connectors 7 extend between adjacent peaks of the zigzag patterns of the first and second bands of cells 47, 48. For example, the connectors may be a relatively short strut that extends between each adjacent peak of the first and second bands of cells 47, 48, i.e., the curved elements 3, 6 closer to the first end 42. Alternatively, the adjacent peaks may be connected directly to one another, e.g., by adjacent curved elements 3, 6. In a further alternative, the adjacent peaks may be intermittently connected, e.g., indirectly by connectors or directly. For example, only every second, third, or fourth set of adjacent peaks around the circumference may be connected to one another.

In addition, the stent 40 may include a plurality of additional bands of cells 49 defining the second portion 43 of the stent 40. Each of the additional bands of cells 49 may include axial elements 8 connected alternately to curved elements 9, thereby defining a zigzag or serpentine and a third axial length 19. Optionally, adjacent bands of cells 49 defining the second portion of the stent 40 may be connected via links 11, as shown, or directly (not shown).

As shown, the axial and curved elements 8, 9 may have a thickness and/or width that is greater than the axial elements 2, 5, and/or curved elements 3, 6. For example, the adjacent bands of cells 49 may be relatively stiff and/or may have a higher yield strength than the first and second bands of cells 47, 48. Thus, in one embodiment, the second portion 43 of the stent 40 may have a substantially uniform configuration requiring substantial plastic deformation to expand. This configuration may be particularly useful for dilating a branch vessel extending from an ostium.

Although each of the bands of cells 49 in the second portion 43 of the stent 40 are shown having similar configurations and axial lengths, it will be appreciated that the dimensions and configurations may be varied between the second band of cells 48 and the second end 44 of the stent 40, if desired. Thus, the portion of the stent 40 between the second band of cells 48 and the second end 44 of the stent may have a substantially homogenous cell structure or non-uniform cell and/or band configurations, e.g., as described elsewhere herein and in the applications incorporated by reference above. In addition, any number of annular bands 49 may be provided, e.g., such that the second portion 43 has a predetermined length corresponding to a length of a lesion being dilated or otherwise treated using the stent 40, e.g., between about three and twenty millimeters (3-20 mm).

Alternatively, the second (e.g., non-flaring) portion 43 of the stent 40 may include other configurations. For example, the second portion 43 may include cells that extend circumferentially, axially, and/or helically along the second portion. The cells may be formed from slotted tubes, rolled sheets, and/or other materials, as described in the applications incorporated by reference above. Alternatively, the second portion 43 may be formed from one or more wire structures, e.g., one or more helical wires extending from the first (e.g., flaring) portion 41 to the second end 44, a braid of multiple wires, and the like. Thus, in some embodiments, the second portion 43 may be formed from any known stent structure or configuration, while the first end portion 41 has the flared configuration described in the embodiments herein.

Returning to FIG. 4A, the first end portion 41 of the stent 40 may be connected to the second portion 43 by a plurality of connectors 10. In an exemplary embodiment, the connectors 10 may be relatively thin and/or otherwise more easily deformed than the first end portion 41 and/or the second portion 43. For example, the connectors 10 may include curvilinear struts, e.g., defining a portion of a sinusoid or other curve. In particular, the connectors 10 may be more flexible and/or easily deformed than the bands of cells 47-49, which may facilitate flaring and/or expansion of the first end portion 41, as described further elsewhere herein.

If desired, one or more portions of the stent 40 (or any of the other embodiments described herein) may include a membrane, film, or coating, e.g., as described in the applications incorporated by reference above. Optionally, the stent may include one or more radiopaque or other markers, e.g., to facilitate monitoring the stent during advancement, positioning, and/or expansion. For example, FIG. 4B shows a stent 40' that includes a plurality of rings 42a extending from the first end 42. The rings 42a may be formed or coated with radiopaque material. In addition or alternatively, the spaces within the rings 42a may be filled with radiopaque material, e.g., by melting, pressing, laser welding, or otherwise fixing material in the spaces. In addition or alternatively, the stent 40 may carry one or more therapeutic or other compounds (not shown) that may enhance or otherwise facilitate treatment of a target location within a patient's body.

Turning to FIGS. 6A-6E, the stent 40 may be provided initially in a contracted condition, in which the first end portion 41 has a reduced profile (not shown), which may be similar to the reduced profile of the second portion 43 shown in FIGS. 6A, 6C. For example, in the contracted condition, the stent 40 may have a substantially uniform diameter, e.g., between about one half and two millimeters (0.5-2 mm). The stent 40 may be configured to be directed to a flared condition, e.g., in which the first end portion 41 is flared and the second portion 43 remains in the reduced profile, as shown in FIGS. 5A, 6A, and 6C.

More particularly, as best seen in FIG. 5A, the first end portion 41 may be expanded such that the first end 42 defines a diameter or other periphery that is much larger than the second portion. For example, the first end portion 41 may be flared to an outer diameter of between about three to twelve millimeters (3-12 mm), e.g., about seven millimeters (7 mm). Thus, in the flared condition, the first end portion 41 may have an outer diameter that is two to five (2-5) times the diameter of the second portion 43.

Also, in the flared condition, the orientation of the struts 2, 5 of the first and second bands of cells 47, 48 may be directed from substantially axial orientations to at least partially radial and/or circumferential orientations. For example, as best seen in FIG. 5A, the struts 5 in the second set of cells 48 may be directed from a substantially axial orientation (not shown, see FIG. 4A) to a radially outward orientation. As shown, the struts 5 extend substantially radially outwardly from the central longitudinal axis 46 in the flared condition.

In addition, in the flared condition, the struts 2 of the first band of cells 47 may be directed from a substantially axial orientation (not shown, see FIG. 4A) to an at least partially radial and/or circumferential orientation. As shown in FIG. 5A, the first band of cells 47 remains in a zigzag pattern except that the struts 2 are forced away from one another by the connectors 7 to accommodate the flaring of the first end portion 41. As this occurs, the curved segments 3 of the first band of cells 47 may be plastically expanded, e.g., at least partially straightened, such that the struts 2 extend at least partially circumferentially around the first end 42 of the stent 40.

One feature that may accommodate the flared condition is the flexible connectors 10. The connectors 10 may bend easily compared to other structures of the stent 40 to allow the second band of cells 48 to move from a cylindrical shape to a flower-petal or frustoconical shape. Thus, it may be possible that the curved segments 6 further from the axis 46 remain substantially undeformed in the flared condition, and the curved segments 6 closer to the axis 46 may be minimally deformed, i.e., the connectors 10 may bear most of the stress induced by expansion of the stent 40 to the flared condition.

In addition, the relative flexibility of the connectors 10 may facilitate flaring the first end portion 41 closer to ninety degrees (90°). As the first end portion 41 is directed outwardly towards the flared condition, the second band of cells 48 may be pivoted about the connectors from the axial orientation to the radial orientation, thereby creating a more abrupt bend. In exemplary embodiments, the angle between the longitudinal axis and the second band of cells 48 may be between about forty five and ninety degrees (45-90°).

Thereafter, when the second portion 43 (and optionally the first end portion 41) of the stent 40 is expanded to the filly expanded or deployed condition, the struts 2, 5 of the first and second bands of cells 47, 48 may be directed to a more circumferential orientation. With particular reference to FIG. 5B, the struts 2 of the first band of cells 47 may be directed to a substantially circumferential orientation and the curved segments 3 may be further straightened, e.g., such that the first band of cells 48 approximates a circle, e.g., which may distribute the stresses substantially equally between the struts 2 and curved segments 3.

As the first band of cells 47 becomes approximately circular, the second band of cells 48 may be compressed between the first band of cells 47 and the expanding second portion 43. This may cause the struts 5 of the second band of cells 48 to separate from one another and extend at least partially circumferentially around the central axis 46, thereby causing the curved segments 6 to open. Thus, in the fully deployed condition, the ratio of the outer diameter of the first end 42 to the enlarged diameter of the second portion 43 may decrease, e.g., to about 1.1-1.8. For example, in the fully deployed condition, the second portion 43 may have a diameter between about two and eight millimeters (2-8 mm) and the first end 42 may have an outer diameter between about four and fifteen millimeters (4-15 mm).

The stent 40 may be delivered endoluminally, e.g., using a delivery apparatus, such as those described elsewhere herein and in the applications incorporated by reference herein. For example, turning to FIGS. 6A and 6B, a balloon catheter 10 may be provided tat includes a catheter or other elongate tubular member 12 having a proximal end (not shown), a distal end 16, and one or more lumens (not shown) extending between the proximal end and distal end 16. One or more balloons or other expandable members 22 are provided on the distal end 16, e.g., a first proximal balloon 22a and a second distal balloon 22b as shown. The stent 40 may be mounted around the distal end 16 of the catheter 12, e.g., surrounding the one or more expandable members 22.

Optionally, the apparatus 10 may include a sheath or other cover (not shown) that may surround or otherwise cover the stent 40. The sheath may be removable from over the proximal or distal portions of the stent 40 or the entire stent 40 to expose the stent 40 before deployment. In addition or alternatively, the catheter 12 may include one or more radiopaque markers, e.g., markers 29 positioned on the catheter 12 adjacent the ends 42, 44 of the stent 40.

The apparatus may be used to deliver the stent 40 into an ostium or bifurcation (not shown), i.e., an opening in a wall of a first or main body lumen that communicates with a second or branch body lumen. In an exemplary embodiment, the main body lumen may be the aortic root and the branch body lumen may be a coronary or renal artery. In another embodiment, the main body lumen may be the aorta, and the branch body lumen may be a renal artery, or other peripheral vessel. It will be appreciated that the apparatus and methods described herein may be applicable to a variety of bifurcations or branch body lumens that extend transversely, e.g., laterally or substantially perpendicular, from a main body lumen, e.g., within a patient's vasculature, gastrointestinal systems, or other systems.

Initially, a guidewire or other rail may be introduced from the main body lumen through the ostium into the branch, e.g., similar to the methods described elsewhere herein. Optionally, a guide catheter may be advanced over the guidewire into the main body lumen, e.g., until a distal end of the guide catheter is disposed adjacent or proximal to the ostium. The guide catheter may be used to advance one or more instruments over the guidewire and into the main body lumen and/or branch body lumen.

With the stent 40 in the contracted condition, the distal end 16 of the apparatus 10 may be advanced over the guidewire and/or through the guide catheter from the entry site into the main body lumen. The apparatus 10 may be positioned to place the stent 40 at least partially within the ostium, e.g., such that the first end 42 is disposed adjacent the ostium and the second end 44 is disposed within the branch.

As shown in FIG. 6A, the first balloon 22a may be inflated to expand the first end portion 41 of the stent 40 to the flared condition. If the first end portion 41 is expanded adjacent the ostium, the apparatus 10 may be advanced to abut the flared first end portion 41 against the ostium. Optionally, the apparatus 10 may be advanced with sufficient force to cause partial deformation of the flared first end portion 41, e.g., to conform the first end portion 41 at least partially to the shape of the ostium. Alternatively, if the first end portion 41 is disposed partially in the ostium, flaring the stent 40 may cause the stent 40 to back partially out of the ostium, e.g., as described in the applications incorporated by reference herein.

Turning to FIG. 6B, the second balloon 22b may then be inflated to expand the second portion 43 and/or further expand the first end portion 41. Thus, the second portion 43 may be expanded to engage the inner wall of the branch lumen and/or the first end portion 41 may be further expanded to engage the wall of the ostium, thereby substantially securing the stent 40 in position. The balloons 22 may then be deflated, and the apparatus 10 removed, leaving the stent 40 within the ostium.

As shown in FIGS. 6D and 6E, the stent 40 may be expanded to a variety of different shapes to accommodate ostia having different shapes. For example, as shown in FIG. 6D, the stent 40 may be expanded such that the second portion 43 assumes a relatively large diameter to accommodate a larger branch, while the first end portion 41 is flared more abruptly to accommodate an ostium having a minimal taper. By comparison, as shown in FIG. 6E, the stent 40 may also be expanded such that the second portion 43 assumes a relatively small diameter to accommodate a smaller branch, while the first end portion 41 is flared more gradually to accommodate an ostium having a more tapered contour.

During expansion of the stent 40, the ratio of the diameter or other cross-section of the ends of the stent 40 may vary. For example, as described above, when the first end portion 41 is flared, e.g., in the intermediate condition, the ratio of the diameter of the first end portion 41 to the second portion 43 may be relatively large, e.g., two to five. Thus, the first end portion 41 may be relatively large, which may facilitate positioning the stent 40 relative to the ostium. When the stent 40 is further expanded to the final deployed condition, the ratio of the first end portion 41 to the second portion 43 may then decrease, e.g., to between 1.1 and 1.8. This may be desirable to provide a more uniform distribution of the stent 40 relative to the ostium after deployment. In addition or alternatively, it may reduce the risk of the first end portion 41 extending into the main lumen and/or may facilitate recrossing the ostium later with a guidewire or other device.

Figure 7:
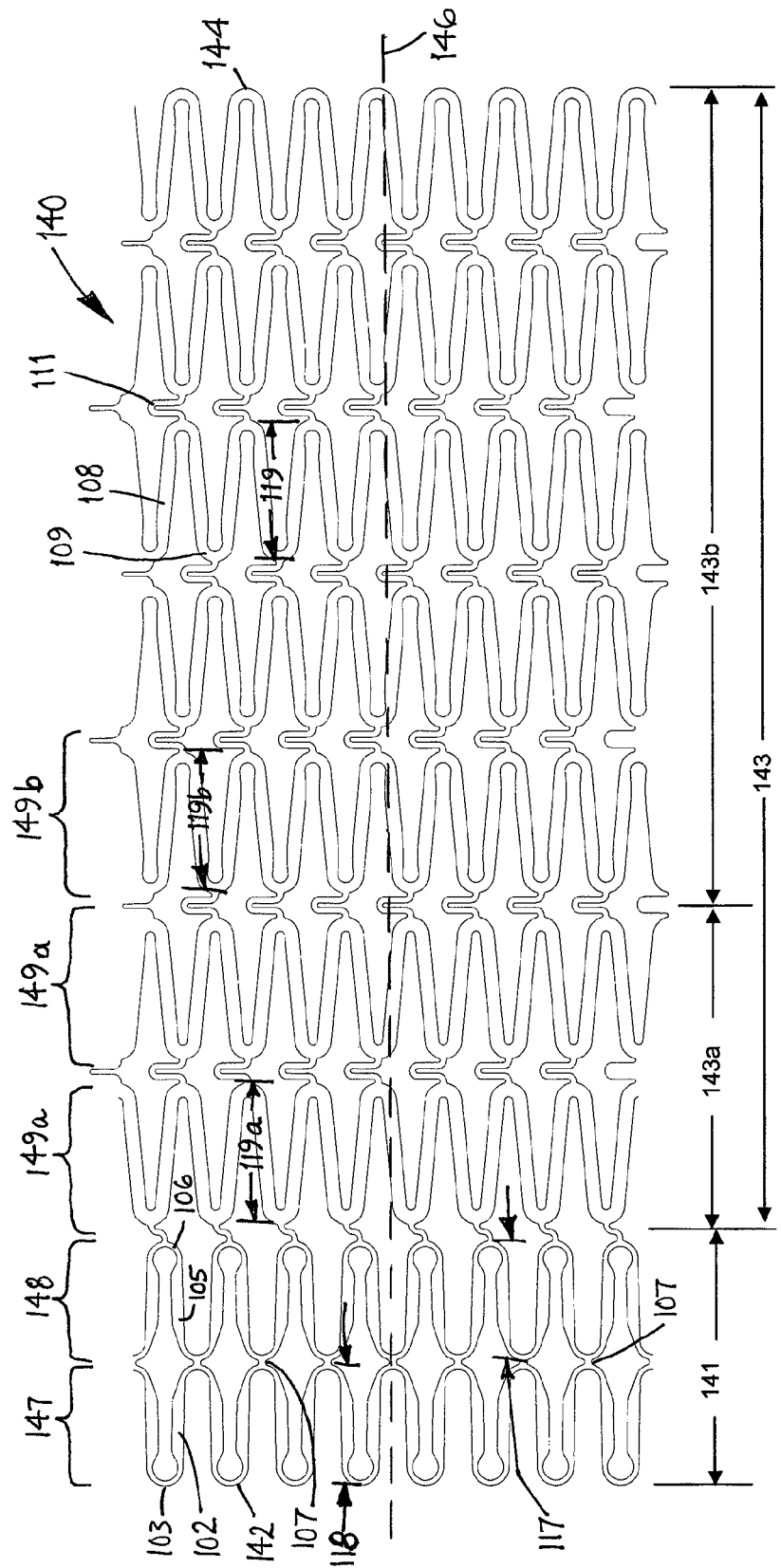
FIG. 7 is a top view of a cell pattern for a stent having a first flaring portion and a second main portion including a proximal main portion and a distal main portion.

Turning to FIG. 7, another embodiment of a stent 140 is shown that includes first and second ends 142, 144 defining a longitudinal axis 146 therebetween. Generally, the stent 140 includes a first or flaring portion 141 and a second or main body portion 143, similar to the previous embodiments.

Also similar to the previous embodiments, the stent 140 may include first and second bands of cells 147, 148 defining the first end portion 141 of the stent 140. The first band of cells 147 at the first end 142 generally includes a zigzag or serpentine pattern defined by a plurality of axial elements 102 connected alternately by curved elements 103 extending about the circumference of the stent 140. The axial elements 102 may be substantially straight, e.g., extending substantially parallel to the longitudinal axis in the contracted condition, as shown in FIG. 7.

Generally, the first band of cells 147 includes a first axial length 118 substantially parallel to the longitudinal axis 146. The first axial length 118 may be defined at least partially by a length of the axial elements 102, e.g., depending upon whether the axial elements 102 extend substantially parallel to the longitudinal axis 146, as shown, or extend at an angle relative to the longitudinal axis (not shown).

The second band of cells 148 adjacent the first band of cells 147 also generally includes a zigzag or serpentine pattern defined by axial elements 105 connected alternately by curved elements 106 extending about the circumference of the stent 140. As shown, the second band of cells 148 may define an axial length 117, which may be substantially similar to the first band of cells 147. For example, the axial elements 102, 105 may have substantially the same length and the curved elements 103, 106 may have substantially the same radius of curvature. In the embodiment shown, the first and second band of cells 147, 148 are substantial mirror images of one another.

As shown, the axial elements 102, 105 have a thickness and/or width that is greater than the curved elements 103, 106. Thus, the yield strength of the curved elements 103, 106 may be less than the axial elements 102, 105, which may facilitate radial flaring of the first end portion 141, as explained elsewhere herein.

In addition, the second band of cells 148 may be connected to the first band of cells 147 by one or more struts or other connectors 107. Generally, the connectors 107 extend between adjacent peaks of the zigzag patterns of the first and second bands of cells 147, 148. For example, the connectors 107 may be relatively short, axial struts that extend between adjacent peaks of the first and second bands of cells 147, 148, i.e., the curved elements 103, 106 closer to the first end 142. Alternatively, the adjacent peaks may be connected directly to one another, e.g., by adjacent curved elements 103, 106, and/or the first and second bands of cells 147, 148 may be only intermittently connected, similar to other embodiments described elsewhere herein. In a further alternative, the first and second bands of cells 147, 148 may be connected by sinusoidal struts (not shown).

With continued reference to FIG. 7, the second main portion 143 of the stent 140 may include a plurality of bands of cells 149 connected to one another along a length of the second portion 143. Each band of cells 149 may include axial elements 108 connected alternately to curved elements 109, thereby defining a zigzag or serpentine pattern, which may define a third axial length 119. Optionally, adjacent bands of cells 149 defining the second portion 143 of the stent 140 may be connected via links 111. The links 111 may be struts defining at least a portion of a generally sinusoidal wave or other curvilinear shape, as shown. Alternatively, the links 111 may be axial struts (not shown), or the adjacent bands of cells 149 may be connected directly, e.g., by adjacent curved elements 109 (also not shown). The links 111 may be relatively narrow and/or thin compared to the curved elements 109, e.g., to facilitate bending or conformability of the second portion 143 of the stent 140.

In an exemplary embodiment, the bands of cells 149 of the second main portion 143 may have a higher radial force than the bands of cells 147, 148 of the first flaring portion 141. For example, the axial and curved elements 108, 109 may have a thickness and/or width greater than the axial elements 102, 105, and/or curved elements 103, 106. Consequently, the bands of cells 149 may be relatively stiff and/or may have a higher yield strength than the first and second bands of cells 147, 148. For example, the bands of cells 149 may have a greater radial strength, thereby providing greater luminal support than the bands of cells 147, 148. In addition or alternatively, the bands of cells 149 may provide greater resistance to expansion than the bands of cells 147, 148, which may minimize expansion of the bands of cells 149 closest to the flaring portion 141 when the flaring portion 141 is flared, as described further below.

Unlike the previous embodiments, the second main portion 143 may include a proximal main portion 143a and a distal main portion 143b, having different characteristics from one another. For example, the proximal main portion 143a may have a greater radial strength than the distal main portion 143b, e.g., to enhance dilation of an ostium, as described further below. In order to increase the radial strength of the proximal main portion 143a, the axial and/or curved elements 108a, 109a may have a greater width than the axial and/or curved elements 108b, 109b. In an exemplary embodiment, the elements 108a, 109a may have a width between about 0.007-0.009 inch (0.18-0.23 mm), e.g., about fifteen and fifty percent (15-50%) greater than the elements 108b, 109b. Alternatively, one or more other dimensions, e.g., thickness and length, and/or cell configuration may be varied between the proximal main portion 143a and the distal main portion 143b to enhance the relative radial strength and/or stiffness of the proximal main portion 143a compared to the distal main portion 143b.

It will be appreciated that any number of annular bands 149 may be provided, e.g., such that the second main portion 143 has a predetermined length corresponding to a length of a lesion being dilated or otherwise treated using the stent 140, e.g., between about three and twenty millimeters (3-20 mm). Each of the proximal and distal main portions 143a, 143b may include a plurality of bands of cells 149a, 149b. In an exemplary embodiment, the distal main portion 143b may include more bands of cells 149b than the proximal main portion 143a. For example, as shown, the proximal main portion 143a includes two bands of cells 149a, while the distal main portion 143b includes at least three, four, five, six, or more bands of cells 149b. Thus, the proximal main portion 143a may be disposed in or immediately adjacent an ostium, while the distal main portion 143b may extend across and beyond a lesion (not shown) being treated, e.g., as explained further below.

Figure 8:
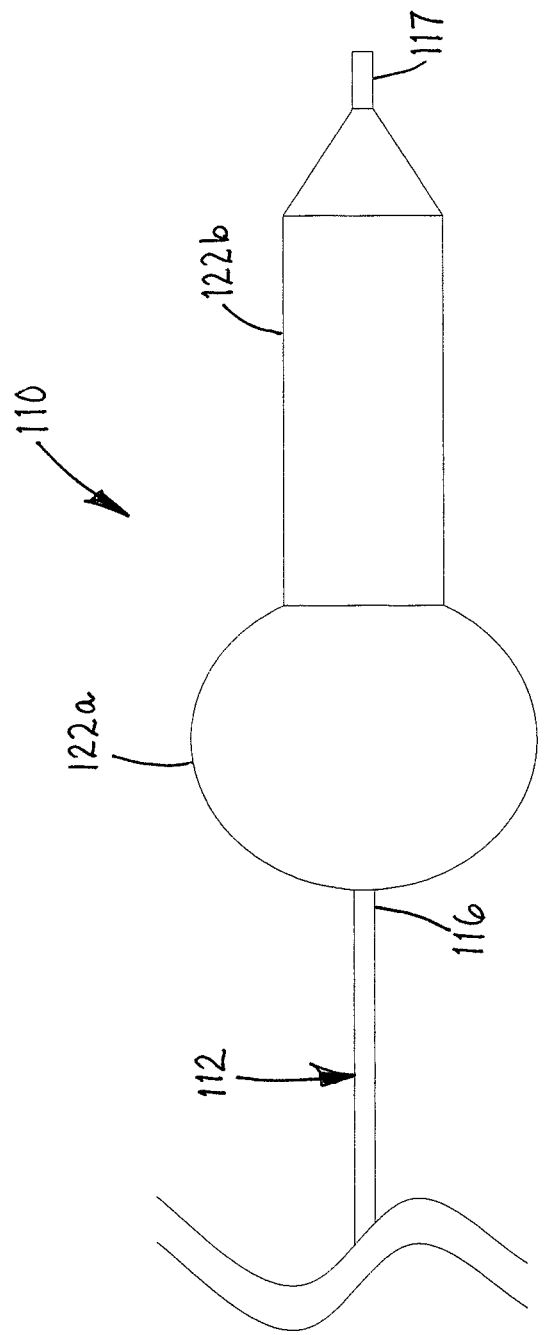
FIG. 8 is a side view of an exemplary embodiment of a distal end of a stent delivery catheter including inflated proximal and distal balloons, the proximal balloon having a substantially spherical shape and the distal balloon having a substantially cylindrical shape when inflated.
Figure 9:
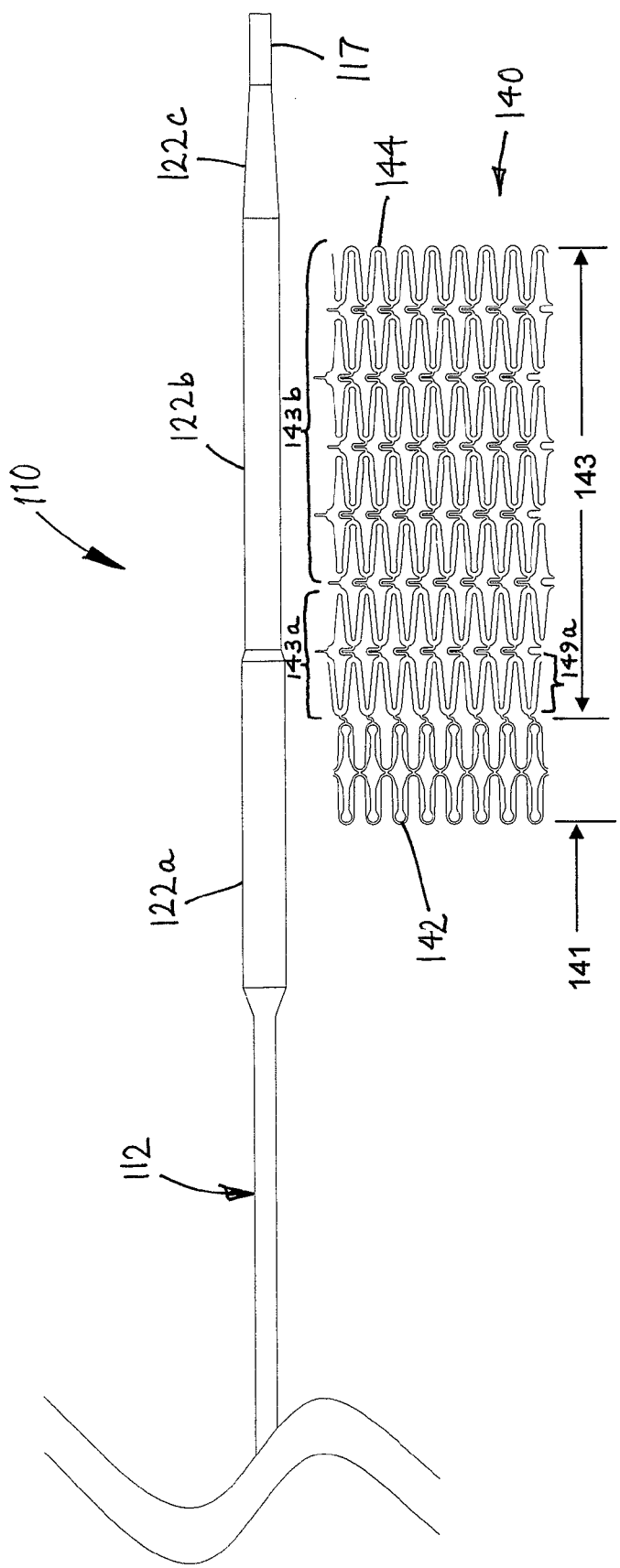
FIG. 9 is a side view of the distal end of the stent delivery catheter of FIG. 8 with the proximal and distal balloons in a collapsed configuration and showing an exemplary arrangement for loading the stent of FIG. 7 onto the distal end.

Turning to FIGS. 8 and 9, an exemplary embodiment of a delivery apparatus 110 is shown that includes a catheter or other elongate tubular member 112 having a proximal end (not shown), a distal end 116, and one or more lumens (also not shown) extending between the proximal end and distal end 116. One or more balloons or other expandable members 122 are provided on the distal end 116, e.g., a first proximal balloon 122a and a second distal balloon 122b adjacent a distal tip 117 of the catheter 112. Materials and methods for making the delivery apparatus 110 may be found in co-pending application Ser. No. 11/136,266, filed May 25, 2006, the entire disclosure of which is expressly incorporated by reference herein, or in the other applications incorporated by reference herein. In addition, the delivery apparatus 110 may include one or more sources of inflation media (not shown), e.g., one or more syringes filled with saline or other fluid that communicate with respective balloons 122.

Generally, the balloons 122 are expandable from a contracted condition (shown in FIGS. 9 and 10A) and an enlarged condition (shown in FIGS. 8 and 10B). An interior of each balloon 122a, 122b may communicate with a respective inflation lumen (not shown) in the catheter 112 such that the balloons may be independently inflated and/or deflated. In an exemplary embodiment, the proximal balloon 122a may be formed from a substantially complaint or semi-compliant material, e.g., polyethylene, polyurethane, and low to mid durometer PEBAX, and the distal balloon 122b may be formed from a semi-compliant or substantially non-compliant material, e.g., mid to high durometer PEBAX, nylon, or PET.

In addition or alternatively, the balloons 122 may require different internal pressures and/or pressures sufficient to fully expand the respective balloons 122. For example, the distal balloon 122a may require a greater inflation pressure to fully expand than the proximal balloon 122b. As explained further below, this may allow the proximal balloon 122a to be expanded using a lower inflation pressure to flare and/or shape a flaring portion of a stent thereon without substantial expansion of a main portion of the stent. Thereafter, the distal balloon 122b may be expanded using a higher inflation pressure to expand the main portion of the stent, which may enhance dilating an occlusion or other lesion at or adjacent an ostium.

Alternatively, during use, the proximal balloon 122a may be inflated based upon delivering one or more predetermined volumes of fluid therein, e.g., in multiple stages of expansion, as described further below. For example, the proximal balloon 122a may be partially inflated upon delivering a first predetermined volume of fluid therein to flare the stent before positioning the apparatus 110, e.g., between about 0.25-2 cubic centimeters. After positioning the stent and expanding the distal balloon 122b, the proximal balloon 122a may be fully inflated upon delivering a second larger predetermined volume of fluid therein, e.g., between about 0.5-4.2 cubic centimeters, to further flare or otherwise shape the stent, as explained further below. Volume-based delivery may be useful for describing the function of the proximal balloon 122a because of its relative compliance and/or low pressure requirements.

Optionally, a source of inflation media communicating with the proximal balloon 122a may include indicia or other features that identify or limit the source to facilitate delivering the first predetermined volume and the second predetermined volume successively to facilitate two-stage expansion of the proximal balloon 122a. For example, a syringe may be provided that includes first and second position markers (not shown). When a plunger of the syringe is depressed to the first marker, this may correspond to delivering the first predetermined volume into the proximal balloon 122a. When the plunger is depressed further to the second marker, this may correspond to delivering the second predetermined volume into the proximal balloon 122a.

As shown in FIG. 8, the proximal balloon 122a is shaped to expand to a substantially spherical shape in the enlarged condition, e.g., having a diameter between about ten and twenty millimeters (10-20 mm) when expanded using an inflation pressure between about one and five atmospheres (1-5 ATM). In an exemplary embodiment, the proximal balloon 122a may have a diameter of about thirteen millimeters (13 mm) at an inflation pressure of about two atmospheres (2 ATM). In contrast, the distal balloon 122b may be shaped to expand to a substantially cylindrical shape in the enlarged condition, e.g., having a diameter between about two and eight millimeters (2-8 mm) when expanded using an inflation pressure between about eight and twenty atmospheres (8-20 ATM).

In addition, the distal balloon 122b may have a substantially uniform diameter portion, e.g., having a length between about eight and thirty millimeters (8-30 mm). Beyond the uniform diameter portion, the distal balloon 122b may have a transition portion 122c adjacent the distal tip 117. The transition portion 122c may be tapered, as shown, or may be substantially blunt, i.e., extending inwardly to the distal tip 117 (not shown). Optionally, the distal balloon 122b may underlie at least a portion of the proximal balloon 122a, e.g., as disclosed in the applications incorporated by reference elsewhere herein. In an exemplary embodiment, the distal balloon 122b may have a diameter of about six millimeters (6 mm) in the enlarged condition and may have a length of at least about seventeen millimeters (17 mm) distally beyond the proximal balloon 122a.

With particular reference to FIG. 9, the stent 140 may be mounted around the distal end 116 of the catheter 112, e.g., surrounding at least a portion of the balloons 122. Generally, the first flaring portion 141 of the stent 140 overlies the proximal balloon 122a, e.g., a distal portion of the proximal balloon 122a, and the distal main portion 143b of the stent 140 overlies the distal balloon 122b, i.e., between the proximal balloon 122a and the transition portion 122c. The proximal main portion 143a of the stent 140 may overlie one or both of the proximal and distal balloons 122a, 122b. For example, as shown, at least a portion of one of the bands of cells 149a may overlie the proximal balloon 122a, while the remainder of the bands of cells 149a may overlie the distal balloon 122b. This overlap of the proximal main portion 143a of the stent 140 may allow a steeper flare of the stent 140, as explained further below.

Optionally, similar to other embodiments herein, the delivery apparatus 110 may include a sheath or other cover (not shown) that may surround or otherwise cover the stent 140. The sheath may be removable from over the proximal or distal portions of the stent 40 or the entire stent 40 to expose the stent 40 before deployment.

Turning to FIGS. 11A-11D, the apparatus 110 may be used to deliver the stent 140 into an ostium 90, i.e., an opening communicating between a first or main body lumen 92 and a second or branch body lumen 94, similar to other embodiments herein.

Initially, a guidewire or other rail 90 (see, e.g., FIG. 11D) may be introduced from the main body lumen 92 through the ostium 90 into the branch 94. For example, a guidewire may be advanced from a percutaneous puncture or other entry site (not shown), e.g., into a peripheral vessel, such as a femoral or carotid artery, through the patient's vasculature into the main body lumen 92, and into the branch 94. Optionally, as shown in FIG. 11A, a guide catheter 160 may be advanced over the guidewire into the main body lumen 92, e.g., until a distal end 164 of the guide catheter 160 is disposed adjacent or proximal to the ostium 90.

With the stent 140 in the contracted condition, the distal end 116 of the apparatus 110 may be advanced over the guidewire and/or through the guide catheter from the entry site into the main body lumen 92. The apparatus 110 may be positioned to place the stent 140 at least partially within the ostium 90. For example, as shown in FIG. 11A, the distal end 116 of the apparatus 110 may be advanced through the ostium 90 and into the branch 94, i.e., such that the stent 140 and/or balloons 122 cross the lesion being treated. The apparatus 110 may then be withdrawn to position at least the flaring portion 141 of the stent 140 within the main body lumen 92.

Figure 11B:
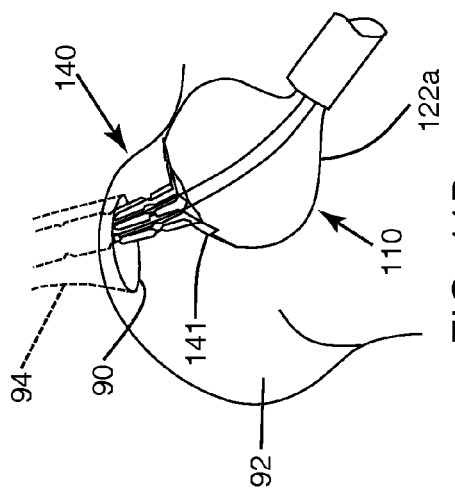
FIGS. 11A-11D are perspective views of an ostium communicating between a main vessel and a branch vessel, showing a method for delivering a stent using the stent delivery catheter of FIGS. 10A and 10B.

Turning to FIG. 11B, the proximal balloon 122a may be inflated to expand the flaring portion 141 of the stent 140, i.e., cause the first and second bands of cells 147, 148 to transition from the axial to peripheral and/or radial configurations, as described above. For example, as explained above, a first predetermined volume of fluid may be delivered into the proximal balloon 122a to partially expand the proximal balloon 122a. Although a portion of the proximal main portion 143a of the stent 140 overlies the proximal balloon 122a, the proximal main portion 143a may resist expansion, e.g., because of the greater radial strength of the proximal main portion 143a and/or the relatively lower inflation pressure used to inflate the proximal balloon 122a. Thus, the flaring portion 141 may be flared outwardly relatively steeply from the proximal main portion 143a.

The apparatus 110 may then be advanced to abut the flared flaring portion 141 against the ostium 90. Optionally, the apparatus 110 may be advanced with sufficient force to cause partial deformation of the flaring portion 141, e.g., to conform at least partially to the shape of the ostium 90. Alternatively, if the flaring portion 141 is disposed partially in the ostium 90 when the proximal balloon 122a is inflated, flaring the stent 140 may cause the stent 140 to back partially out of the ostium 90, e.g., as described further below.

Optionally, the apparatus 110 and/or stent 140 may be monitored during this manipulation, e.g., using fluoroscopy or other external imaging, to confirm proper positioning of the stent 140 within the ostium 90. In this option, the stent 140 and/or apparatus 110 may include radiopaque markers and the like (not shown), e.g., as described elsewhere herein.

Figure 11D:
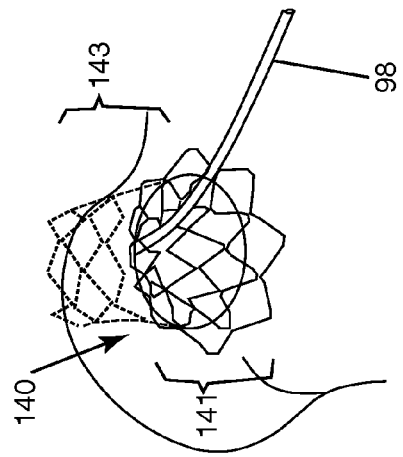
Figure 11A:
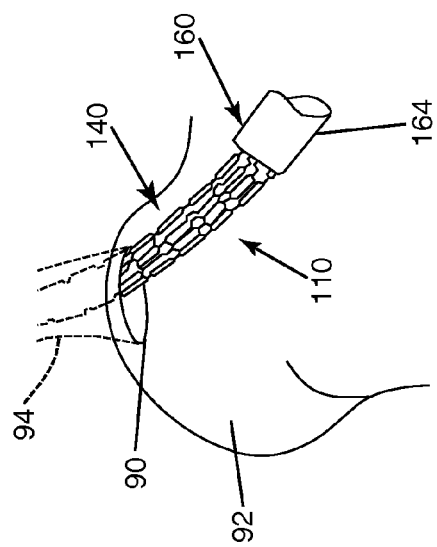
Figure 11C:
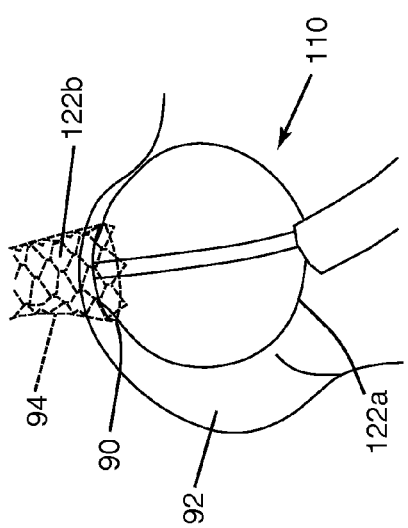

Turning to FIG. 11C, with the stent 140 properly positioned, the distal balloon 122b may be inflated to expand the main portion 143 of the stent 140 and/or further expand the flaring portion 141. For example, the proximal main portion 143a may be expanded to engage the inner wall of the ostium and/or branch, and the distal main portion 143b may be expanded to engage the inner wall of the branch, e.g., to dilate the lesion and/or substantially secure the stent 140 in position. Because of the greater radial strength of the main portion 143, the distal balloon 122b may be inflated to a greater pressure than the proximal balloon 122a, thereby ensuring the main portion 143 is expanded to dilate the lesion.

With the main portion 143 expanded, the stent 140 may be substantially secured from axial movement relative to the branch, e.g., to the friction or other engagement between the expanded main portion 143 and the wall of the branch. If desired, the proximal balloon 122a may then be expanded further, e.g., by delivering a second predetermined volume of fluid therein. This may further flare the flaring portion 141 of the stent 140 and/or compress the flaring portion 141 against the wall of the ostium. The hydraulic pressure applied to the flaring portion 141 by further expanding the proximal balloon 122a may be apply a greater force than can be applied manually, e.g., by advancing the apparatus 110 partially into the ostium.

Turning to FIG. 11D, the balloons 122 may then be deflated, and the apparatus 110 removed, leaving the stent 140 within the ostium 90 and branch 94. Because of the greater radial strength of the proximal main portion 143a, this portion of the stent 140 may have enhanced resistance to being compressed by surrounding tissue. For example, in some applications, the tissue surrounding a lumen may want to recoil, i.e., contract radially inwardly, particularly at the neck of an ostium. Thus, the main portion 143 of the stent 140, particularly, the proximal main portion 143 located within the ostium 90, may resist such recoil, which may enhance maintaining the ostium open for an indefinite time.

Figure 12:
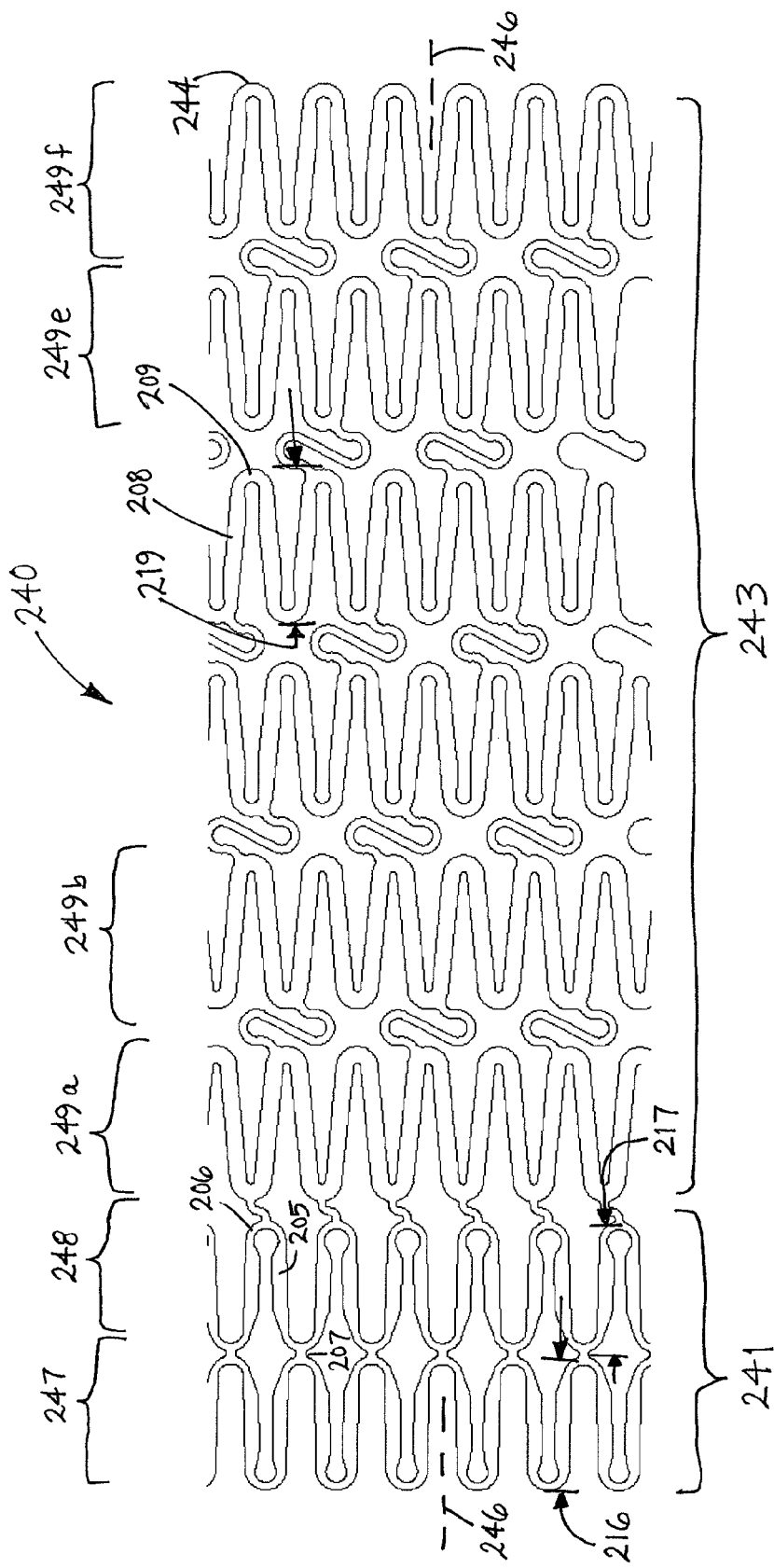
FIG. 12 is a top view of another cell pattern for a stent having a first flaring portion and a second main portion.

Turning to FIG. 12, still another embodiment of a stent 240 is shown that includes first and second ends 242, 244 defining a longitudinal axis 246 therebetween. Generally, the stent 240 includes a first or flaring portion 241 and a second or main body portion 243, similar to the previous embodiments.

Also similar to the previous embodiments, the stent 240 may include first and second bands of cells 247, 248 defining the first end portion 241 of the stent 240. The first band of cells 247 at the first end 242 generally includes a zigzag or serpentine pattern defined by a plurality of axial elements 202 connected alternately by curved elements 203 extending about the circumference of the stent 240. The axial elements 202 may be substantially straight, e.g., extending substantially parallel to the longitudinal axis in the contracted condition, as shown in FIG. 12. Generally, the first band of cells 247 includes a first axial length 216 substantially parallel to the longitudinal axis 246. The first axial length 216 may be defined at least partially by a length of the axial elements 202, e.g., depending upon whether the axial elements 202 extend substantially parallel to the longitudinal axis 246, as shown, or extend at an angle relative to the longitudinal axis (not shown).

The second band of cells 248 adjacent the first band of cells 247 also generally includes a zigzag or serpentine pattern defined by axial elements 205 connected alternately by curved elements 206 extending about the circumference of the stent 240. As shown, the second band of cells 248 may define an axial length 217, which may be substantially similar to the first band of cells 247. For example, the axial elements 202, 205 may have substantially the same length and the curved elements 203, 206 may have substantially the same radius of curvature. In the embodiment shown, the first and second band of cells 247, 248 are substantial mirror images of one another.

As shown, the axial elements 202, 205 have a thickness and/or width that is greater than the curved elements 203, 206. Thus, the yield strength of the curved elements 203, 206 may be less than the axial elements 202, 205, which may facilitate radial flaring of the first end portion 241, as explained elsewhere herein.

In addition, the second band of cells 248 may be connected to the first band of cells 247 by one or more struts or other connectors 207. Generally, the connectors 207 extend between adjacent peaks of the zigzag patterns of the first and second bands of cells 247, 248. For example, the connectors 207 may be relatively short, axial struts that extend between adjacent peaks of the first and second bands of cells 247, 248, i.e., the curved elements 203, 206 closer to the first end 242. Alternatively, the adjacent peaks may be connected directly to one another, e.g., by adjacent curved elements 203, 206, and/or the first and second bands of cells 247, 248 may be only intermittently connected. In a further alternative, the first and second bands of cells 247, 248 may be connected by sinusoidal struts (not shown).

With continued reference to FIG. 12, the second main portion 243 of the stent 240 may include a plurality of bands of cells 249 connected to one another along a length of the second portion 243. Each band of cells 249 may include axial elements 208 connected alternately to curved elements 209, thereby defining a zigzag or serpentine pattern, which may define a third axial length 219. Optionally, adjacent bands of cells 249 defining the second portion 243 of the stent 240 may be connected via links 211. The links 211 may be struts defining at least a portion of a generally sinusoidal wave or other curvilinear shape, as shown. Alternatively, the links 211 may be axial struts (not shown), or the adjacent bands of cells 249 may be connected directly, e.g., by adjacent curved elements 209 (also not shown). The links 211 may be relatively narrow and/or thin compared to the curved elements 209, e.g., to facilitate bending or conformability of the second portion 243 of the stent 240, as described elsewhere herein.

Unlike previous embodiments, as shown in FIG. 12, adjacent bands of cells 249 are intermittently connected to one another. Stated differently, the links 211 are provided only between every other opposing set of curved elements 209 around the circumference of the stent 240. It will be appreciated that other configurations of intermittent connections may be provided, e.g., links extending between every third, fourth, or fifth opposing set of curved elements 209 around the circumference of the stent 240.

The combination of curved links 211 and intermittent links 211 may enhance axial compressibility of the stent 240. For example, the links 211 may allow adjacent bands of cells 249 to move towards and/or away from one another and/or allow localized movement. Thus, particular opposing curved elements 209 that are not connected to one another by links 211 may move towards or away from one another relatively freely (as limited by the overall configuration and structure of the cells defining the stent 240). This feature may allow at least some of the bands of cells 249 to compress axially during deployment within an ostium and/or branch, which may facilitate seating of the stent 240 and/or increase support at the ostium, as described further below.

Similar to some of the embodiments described above, the bands of cells 249 of the second main portion 243 may have a higher radial force than the bands of cells 247, 248 of the first flaring portion 241. For example, the axial and curved elements 208, 209 may have a thickness and/or width greater than the axial elements 202, 205, and/or curved elements 203, 206. Consequently, the bands of cells 249 may be relatively stiff and/or may have a higher yield strength than the first and second bands of cells 247, 248. For example, the bands of cells 249 may a greater radial strength, thereby providing greater luminal support than the bands of cells 247, 248. In addition or alternatively, the bands of cells 249 may provide greater resistance to expansion than the bands of cells 247, 248, which may minimize expansion of the bands of cells 249 closest to the flaring portion 241 when the flaring portion 241 is flared, as described further elsewhere herein.

Optionally, similar to previous embodiments, the second main portion 243 may include a proximal main portion and a distal main portion, having different characteristics from one another (not shown). For example, the proximal main portion may have a greater radial strength than the distal main portion, e.g., to enhance dilation of an ostium and/or enhance resistance to recoil. In an exemplary embodiment, the elements of the proximal main portion may have a width between about 0.007-0.009 inch (0.18-0.23 mm), e.g., about fifteen and fifty percent (15-50%) greater than the elements of the distal main portion. Alternatively, one or more other dimensions, e.g., thickness and length, and/or cell configuration may be varied between the proximal main portion and the distal main portion to enhance the relative radial strength and/or stiffness of the proximal main portion compared to the distal main portion.

It will be appreciated that any number of annular bands 249 may be provided, e.g., such that the second main portion 243 has a predetermined length corresponding to a length of a lesion being dilated or otherwise treated using the stent 240, e.g., between about three and twenty millimeters (3-20 mm).

Turning to FIGS. 13-19, the stent 240 may be delivered into an ostium 90, i.e., an opening communicating between a first or main body lumen 92 and a second or branch body lumen 94, e.g., using apparatus and methods described elsewhere herein. In an exemplary embodiment, the main body lumen 92 may be the aortic root and the branch body lumen 94 may be a coronary or renal artery having a stenosis or other lesion 96 therein. It will be appreciated that the stent 240 may be implanted within a variety of bifurcations or branch body lumens that extend transversely, e.g., laterally or substantially perpendicular, from a main body lumen.

Figure 13:
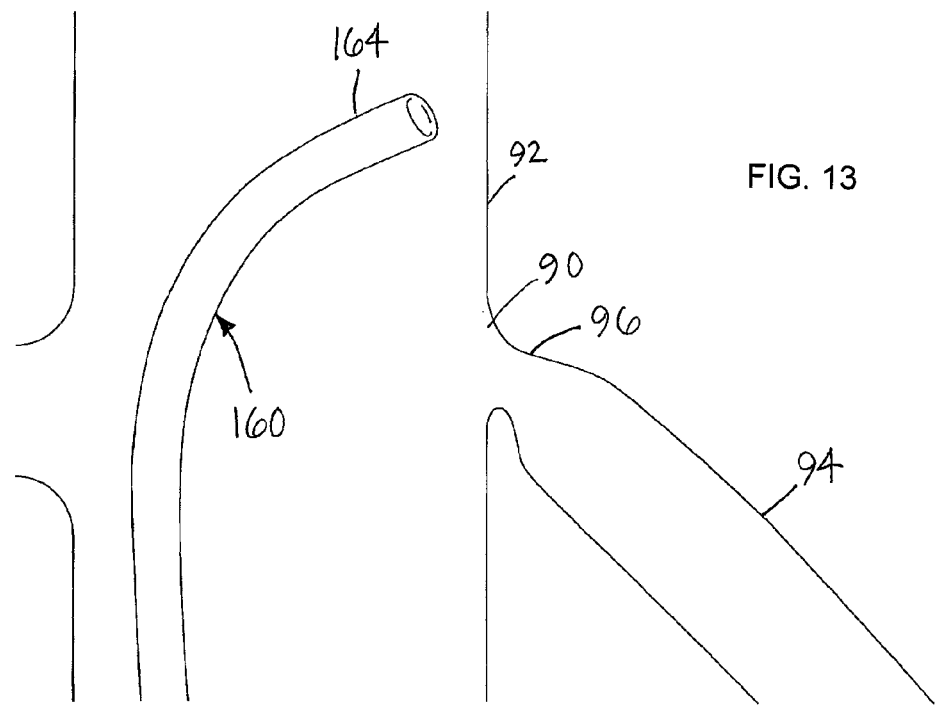
Figure 14:
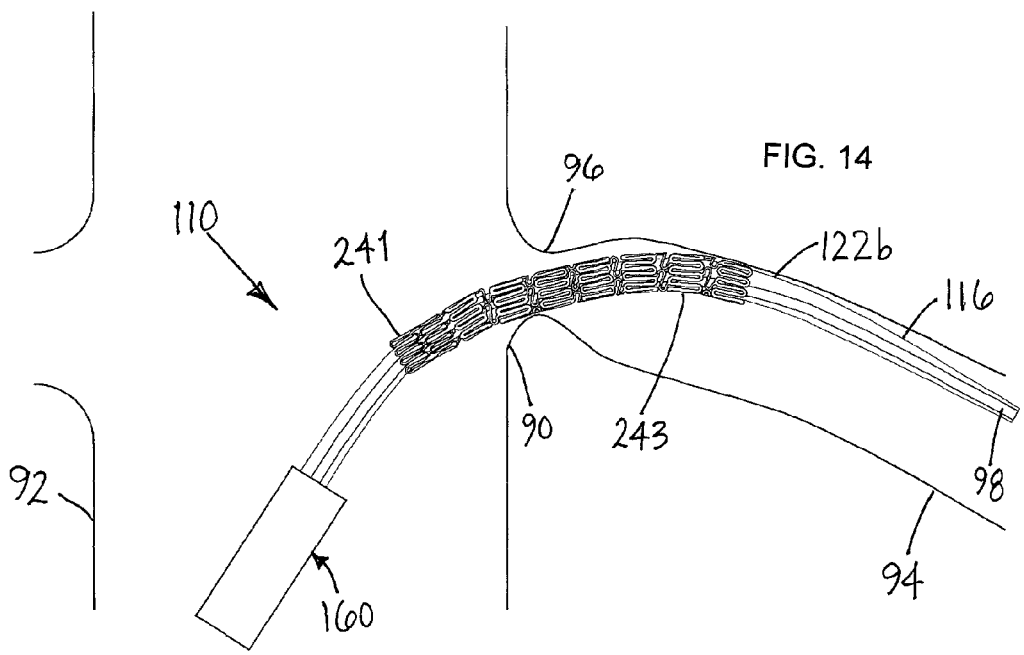

Initially, as shown in FIG. 13, a guide catheter 160 may be advanced into the main body lumen 92, e.g., until a distal end 164 of the guide catheter 160 is disposed adjacent or proximal to the ostium 90. Optionally, as shown in FIG. 14, a guidewire or other rail 98 may be introduced from the main body lumen 92 through the ostium 90 into the branch 94, e.g., via the guide catheter 160. For example, the guide catheter 160 may be advanced or otherwise manipulated until the distal end 164 is engaged in the ostium 90, and the guidewire 98 may be advanced through the guide catheter 160 and passed through the lesion 96. For vascular procedures, the guidewire 98 may be advanced from a percutaneous puncture or other entry site (not shown), through the patient's vasculature into the main body lumen 92, and into the branch 94, using known methods. Alternatively, the guidewire 98 may be introduced before or independent of the guide catheter 160.

Similar to the apparatus and methods described above, as shown in FIG. 14, the stent 240 may be loaded onto a delivery apparatus 100 (which may be any of the embodiments described herein). For example, the stent 240 may positioned over proximal and distal balloons 122a, 122b on a distal end 116 of the apparatus 110 with the stent 240 in the contracted condition. The distal end 116 of the apparatus 110 may be advanced over the guidewire 98 and/or through the guide catheter 160 from the entry site into the main body lumen 92.

For example, as shown in FIG. 14, the distal end 116 of the apparatus 110 may be advanced through the ostium 90 and into the branch 94, i.e., such that the stent 240 and/or balloons 122 at least partially cross the lesion being treated. The guide catheter 160 may then be at least partially retracted, e.g., to expose a proximal balloon 122a on the apparatus 110. If desired, the apparatus 110 may be withdrawn partially to position at least the flaring portion 241 of the stent 240 within the main body lumen 92.

Figure 15:
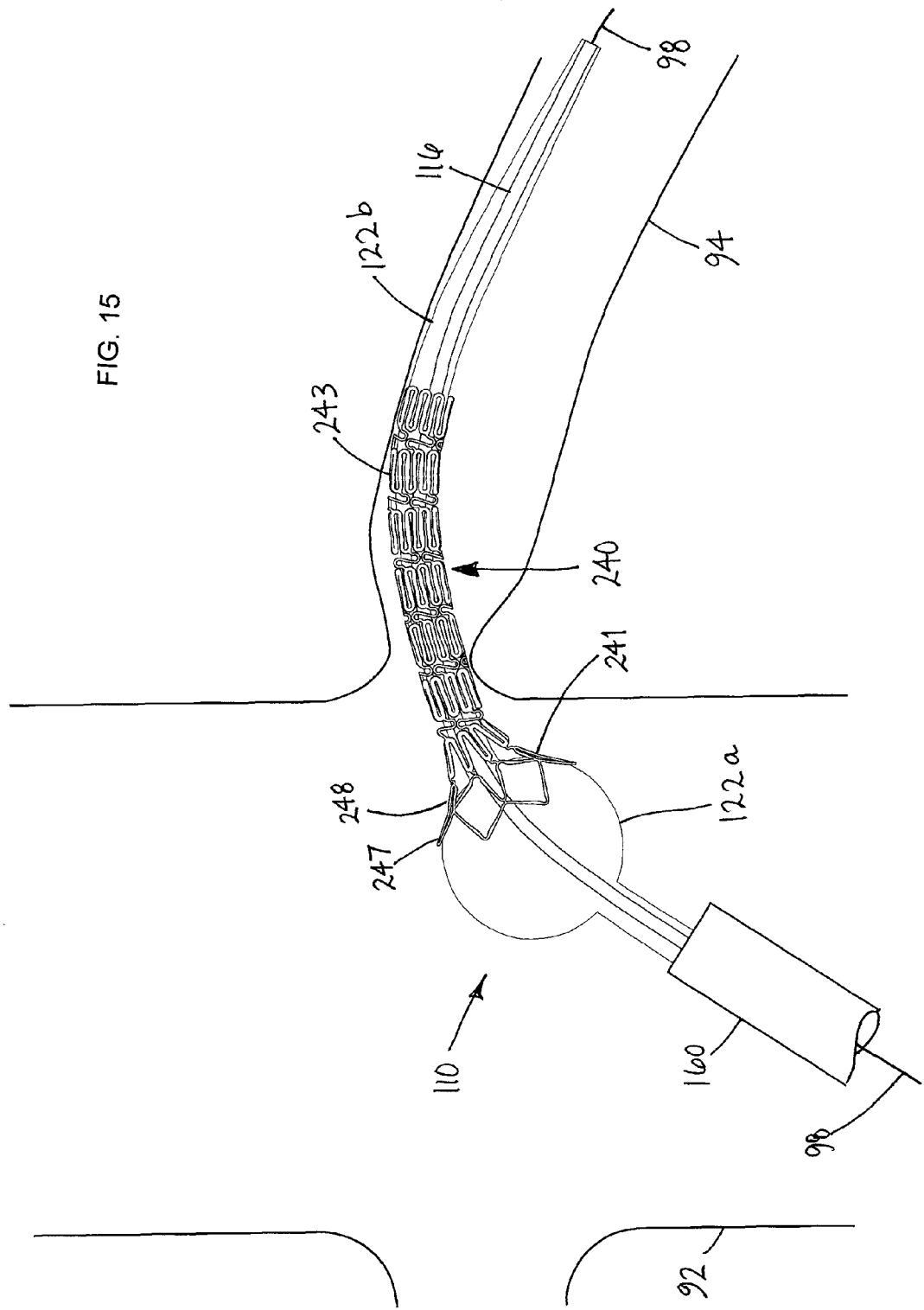

Turning to FIG. 15, the proximal balloon 122a may be inflated to expand the flaring portion 141 of the stent 140, i.e., cause the first and second bands of cells 247, 248 to transition from the axial to peripheral and/or radial configurations, as described above. For example, as explained above, a first predetermined volume of fluid may be delivered into the proximal balloon 122a to partially expand the proximal balloon 122a. Optionally, although a portion of the main portion of the stent 240 may overly the proximal balloon 122a, the proximal main portion may resist expansion, e.g., because of the greater radial strength of the proximal main portion and/or the relatively lower inflation pressure used to inflate the proximal balloon 122a. Thus, the flaring portion 241 may be flared outwardly relatively steeply from the proximal main portion, e.g., to provide a mechanical stop when the apparatus 110 is advanced again into the ostium 90.

Figure 16:
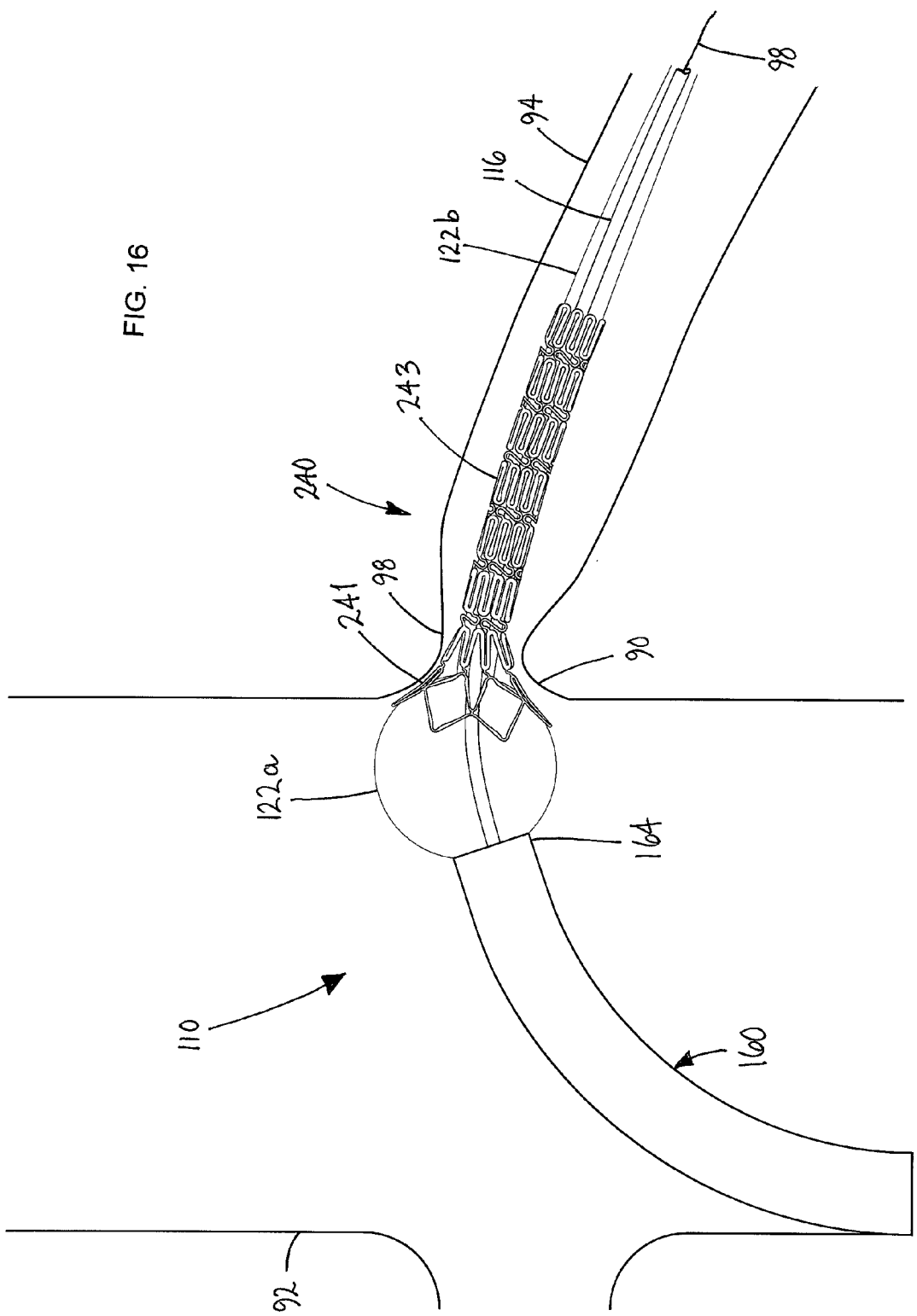

Turning to FIG. 16, the apparatus 110 may then be advanced into the ostium 90 to abut the flared flaring portion 241 against the ostium 90. This may be accomplished by pushing the apparatus 110 from its proximal end (not shown), thereby advancing the distal end 116 through the lesion 98 and at least partially into the branch 94. Alternatively, the guide catheter 160 may be advanced distally, thereby pressing the distal end 164 against the inflated proximal balloon 122a. Further advancement of the guide catheter 160 may push the proximal balloon 122a distally, thereby automatically advancing the apparatus 110 into the ostium 90.

Optionally, the apparatus 110 may be advanced with sufficient force to cause partial deformation of the flaring portion 241, e.g., to conform at least partially to the shape of the ostium 90. Alternatively, if the flaring portion 241 is disposed partially in the ostium 90 when the proximal balloon 122a is inflated, flaring the stent 240 may cause the stent 240 to back partially out of the ostium 90, e.g., as described further below.

Optionally, the apparatus 110 and/or stent 240 may be monitored during this manipulation (and/or other portions of the procedure), e.g., using fluoroscopy or other external imaging, to confirm proper positioning of the stent 240 within the ostium 90. In this option, the stent 240 and/or apparatus 110 may include one or more radiopaque markers and the like (not shown) at predetermined locations thereon.

Figure 17:
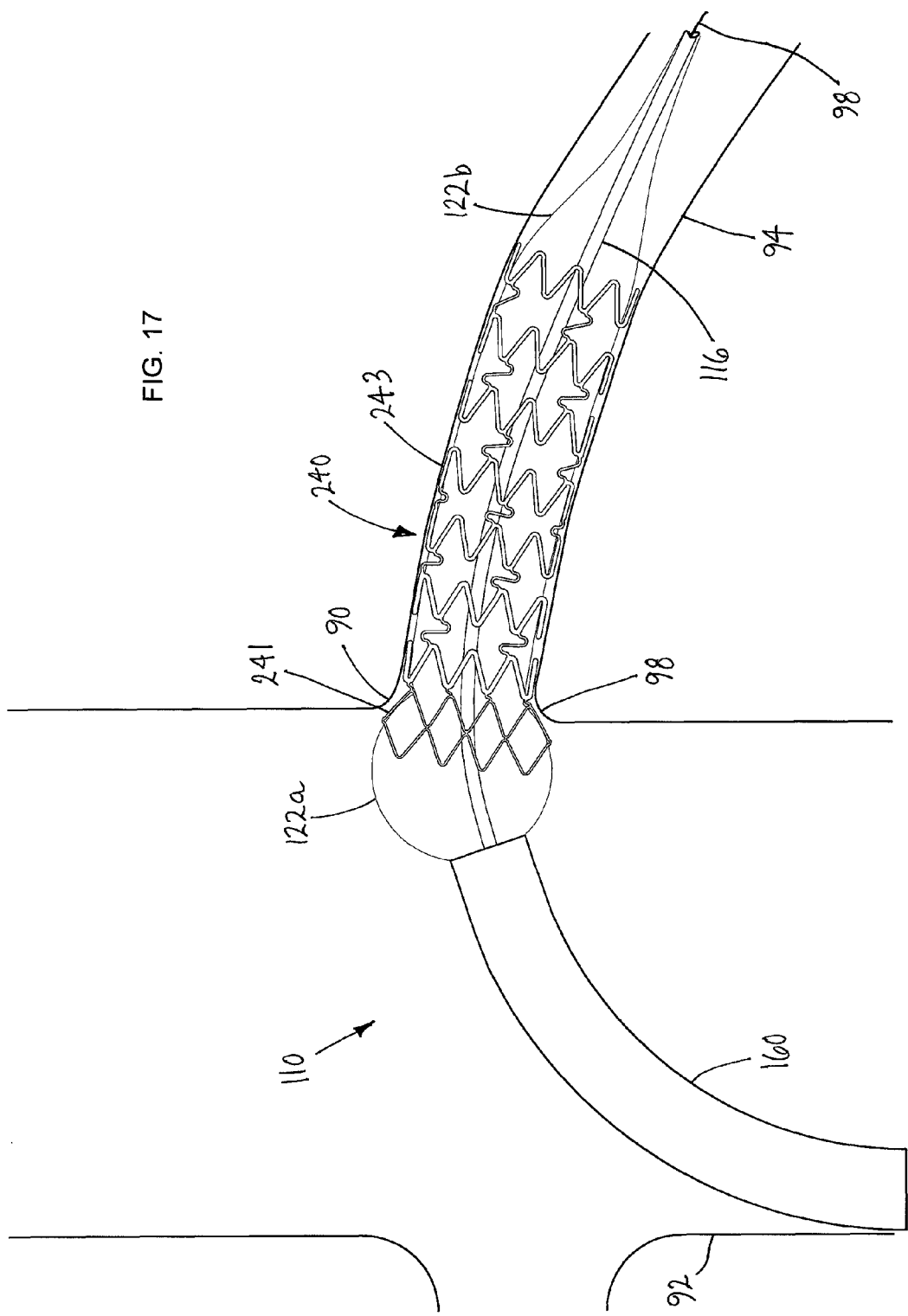

Turning to FIG. 17, with the stent 240 properly positioned, the distal balloon 122b may be inflated to expand the main portion 243 of the stent 240 and/or further expand the flaring portion 241. For example, the main portion 243 may be expanded sufficiently to engage the inner wall of the branch 94 and/or ostium 90, thereby substantially anchoring the stent 240 and/or apparatus relative to the branch 94 and/or ostium 90. Optionally, the main portion 243 may include proximal and distal portions that have different properties and, therefore, are expanded to enhance dilation of the lesion 98 and/or substantially secure the stent 140 in position, as described above.

Turning to FIG. 18, with the main portion 243 expanded and the stent 240 substantially secured within the branch 94, the proximal balloon 122a may then be expanded further, e.g., by delivering a second predetermined volume of fluid therein. This may further flare the flaring portion 241 of the stent 240 and/or compress the flaring portion 241 against the wall of the ostium 90. During this expansion, the stent 240 may be further deformed, e.g., causing axial compression of the main portion 243, as explained further below.

Finally, turning to FIG. 19, the balloons 122 may then be deflated, and the apparatus 110 removed, leaving the stent 240 within the ostium 90 and branch 94. Once the pressure of the balloons 122 is removed (upon deflation of the balloons 122), the flaring portion 241 of the stent 240 may rotate relative to an axis defined by the main body lumen 92, e.g., to define a smaller angle compared to when the balloons 122 are inflated. This is demonstrated by "Angle 2" shown in FIG. 19, which is smaller than "Angle 1" shown in FIG. 18. This change may occur because the stent 240 and surrounding tissue reach a new mechanical equilibrium, e.g., between the stored elastic forces in the stent 240 and in the wall of the branch 94.

Figure 20A:
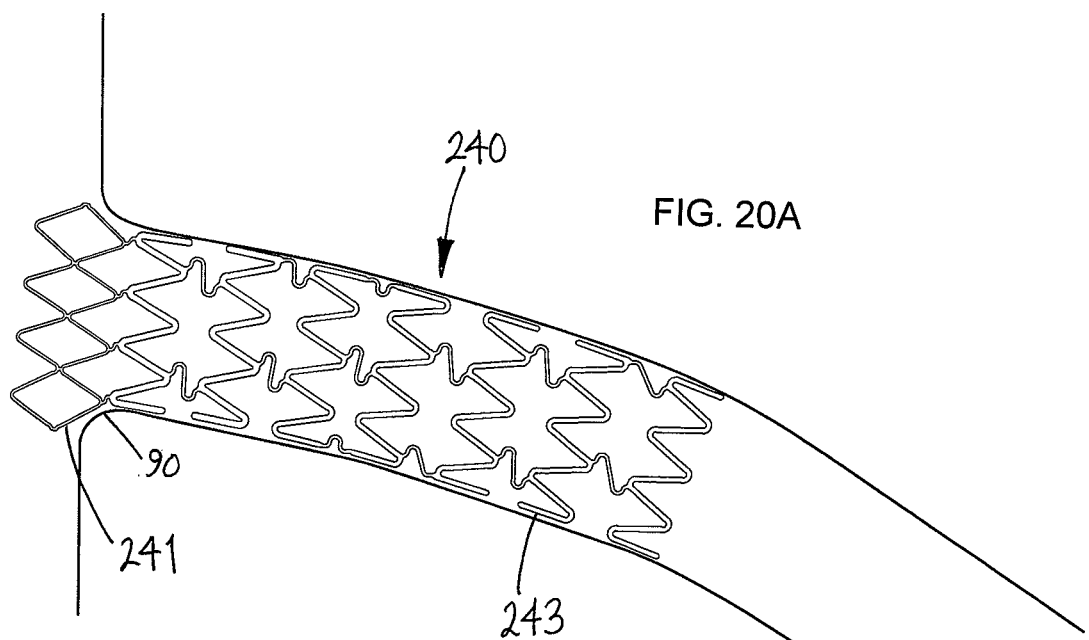
FIGS. 20A and 20B are details of the stent of FIGS. 12-19 before and after final flaring of the stent, respectively.
Figure 20B:
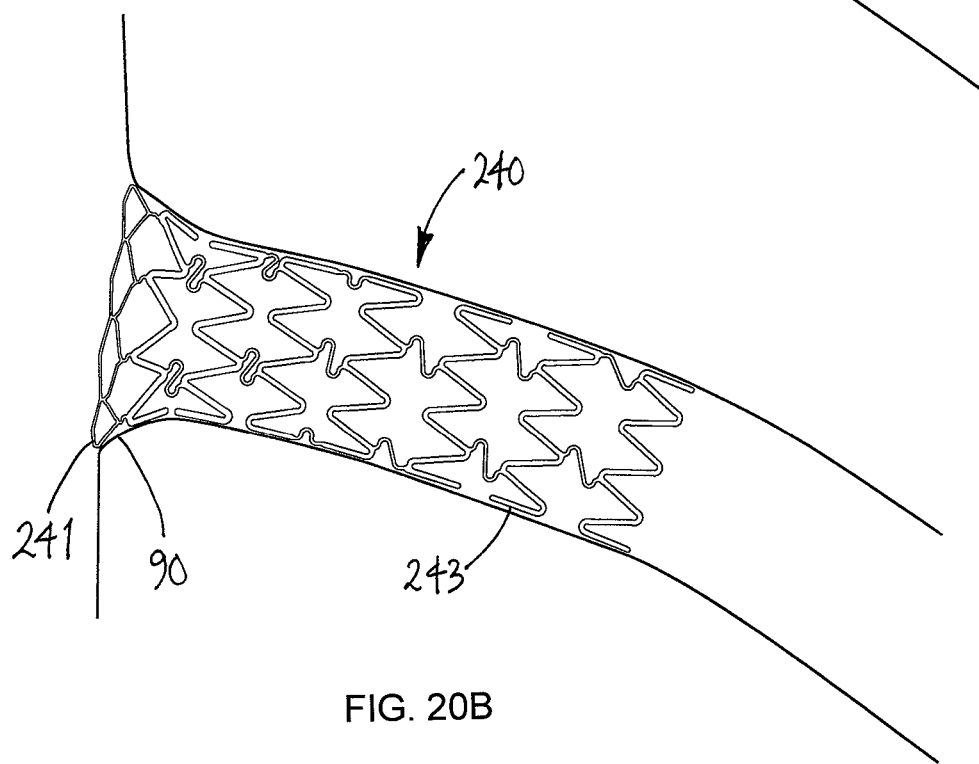

Turning to FIGS. 20A and 20B, the change in configuration of the stent 240 during full inflation of the proximal balloon 122a is shown in greater detail. As shown in FIG. 20A, before full expansion of the proximal balloon 122a (but after expansion of the distal balloon 122b), the stent 240 may have a first length "L-Total" defined by a length "L-flare" of the flaring portion 241 and a length of the main portion 243, which is the sum of "L1" to "L6." With additional reference to FIG. 12, the lengths L1 to L6 are defined at least partially by the length 219 of the bands of cells 249. Although the lengths L1 to L6 are initially substantially the same (as can be seen in FIG. 12), the lengths may vary upon partial expansion, as shown in FIG. 20A.

In particular, at least some of the lengths, e.g., L1, L2, and L3, may be shortened during expansion, e.g., to enhance apposition of the stent 240 relative to the ostium 90. For example, as shown in FIG. 20B, the stent 240 may be farther compressed axially during final inflation of the proximal balloon 122a. Thus, the stent 240 may have a new overall length "L-Total'" that is less than "L-Total." Further, the bands of cells 249 of the main portion 243 may be further foreshortened relative to one another. For example, the bands of cells 249 closest to the ostium 90 may be shortened further, while the bands of cells 249 away from the ostium 90 may remain substantially fixed relative to the branch 94. Thus, at least some of the lengths, e.g., L1,' L2,' and L3' shown in FIG. 20B, may be further shortened as compared to the lengths L1, L2, and L3 shown in FIG. 20A.

This foreshortening may be facilitated by the intermittent connection of the bands of cells 249 to one another, which may increase the density of struts within the lesion 96. Thus, in addition to facilitating conformance of the stent 240 to the ostium 90, the axial compression of the stent 240 may increase support within the lesion 96. Because the ostium 90 may have a thicker and/or more elastic wall than the branch 94, the stent 240 may carry a greater load within the ostium 90, e.g., to prevent the lesion 96 and/or ostium 90 from recoiling to a smaller diameter. Additional information on the advantages of the stent 240 may be found in provisional application Ser. No. 60/745,177, incorporated by reference above.

Figure 21A:
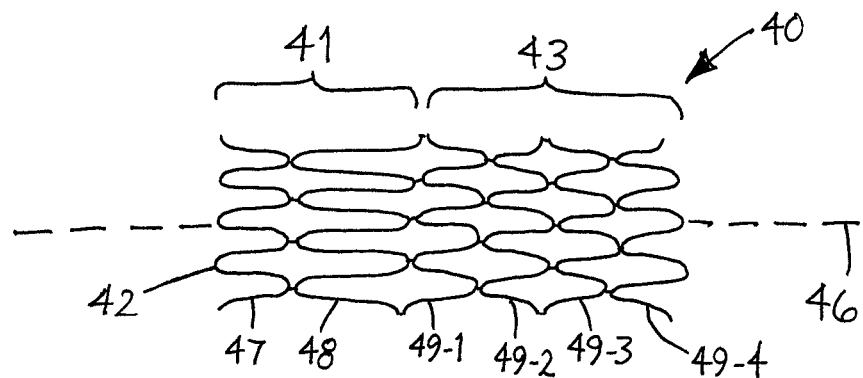
FIGS. 21A and 21B are side views of an exemplary embodiment of a stent in contracted and enlarged conditions, respectively.
Figure 21B:
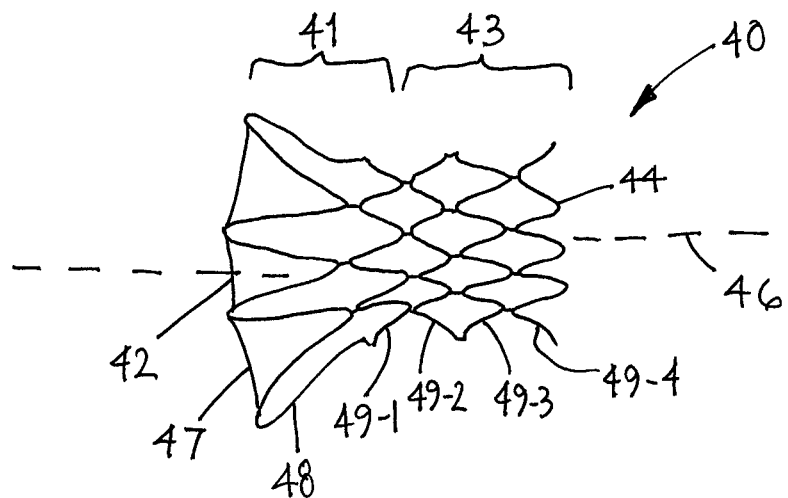
Figure 22:
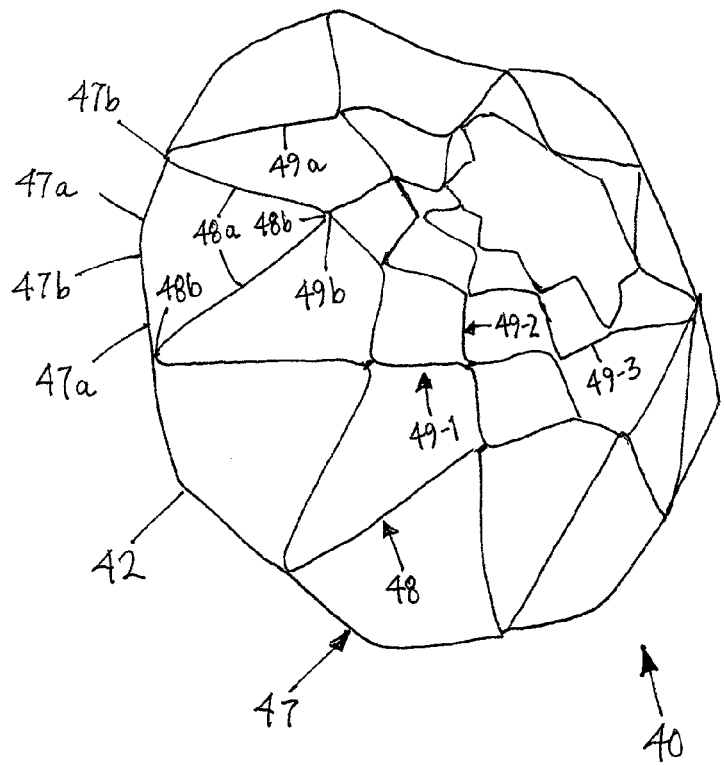
FIG. 22 is a perspective detail of a first end of the stent of FIG. 21B, showing a first end of the stent flared radially outwardly in the enlarged condition.
Figure 23:
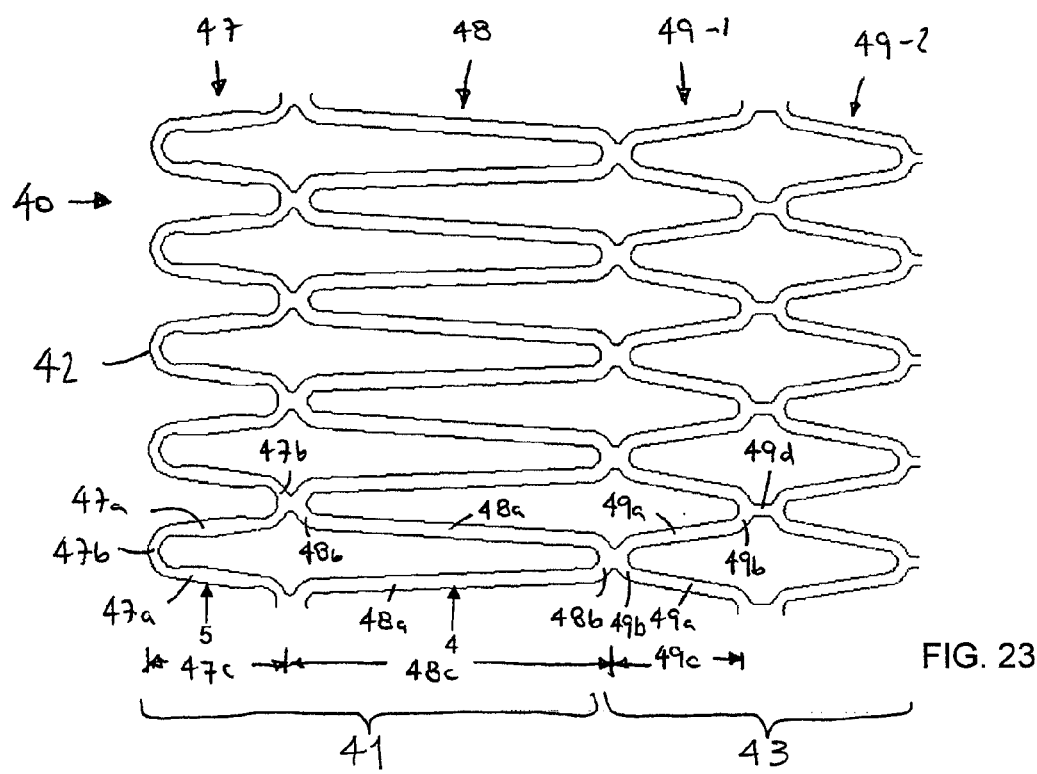
FIG. 23 is a top view of a portion of a cell pattern for the stent of FIGS. 21A-22.

Turning to FIGS. 21-23, another embodiment of a stent 340 that includes a generally cylindrical tubular member including a proximal or first end 342 and a distal or second end 344 defining a longitudinal axis 346 therebetween. The stent 340 is generally radially expandable from a contracted or delivery condition (FIG. 21A) to an enlarged or deployed condition (FIG. 21B). The stent 340 includes a plurality of annular bands of cells 347-349 disposed between the proximal and distal ends 342, 344. Each band of cells 347-349 may be defined by a plurality of struts or other elements extending axially along and/or circumferentially around the stent 340, e.g., in a zigzag or serpentine pattern, thereby defining an open-cell structure. Adjacent bands of cells may be connected to one another, e.g., directly or via links or other elements, similar to other embodiments described elsewhere herein.

As shown in FIG. 23, the stent 340 may include a first band of cells 347 at the first end 342 that includes a zigzag or serpentine pattern defined by a plurality of axial elements 347a connected alternately by curved elements 347b extending about the circumference of the stent 340. The axial elements 347a may be substantially straight, e.g., extending substantially parallel to the longitudinal axis 346 in the contracted condition, as shown in FIG. 21A. Alternatively, the axial elements 347a may include more complicated geometry, similar to other embodiments described elsewhere herein. Generally, with continued reference to FIG. 23, the first band of cells 347 includes a first axial length 347c substantially parallel to the longitudinal axis 346, which may be defined at least partially by a length of the axial elements 347a, e.g., depending upon whether the axial elements 347a extend substantially parallel to the longitudinal axis 46 or extend at an angle relative to the longitudinal axis 46 (i.e., diagonally or circumferentially).

Similarly, the stent 340 may include a second band of cells 348 adjacent the first band of cells 347 that includes a zigzag or serpentine pattern defined by axial elements 348a connected alternately by curved elements 348b extending about the circumference of the stent 340. As shown, the second band of cells 348 may be connected directly to the first band of cells 347, e.g., at adjacent curved elements 347b, 348b. As shown, the second band of cells 348 also includes a second axial length 348c, which may be substantially longer than the first axial length 347c. The first and second bands of cells 347, 348 may provide a first portion 341 of the stent 340 that may flare as the stent 340 is expanded, as explained further below. The set of curved elements 347b at the first end 342 may be substantially free to accommodate expansion and/or flaring of the first portion 341, also as described farther below.

Figure 24:
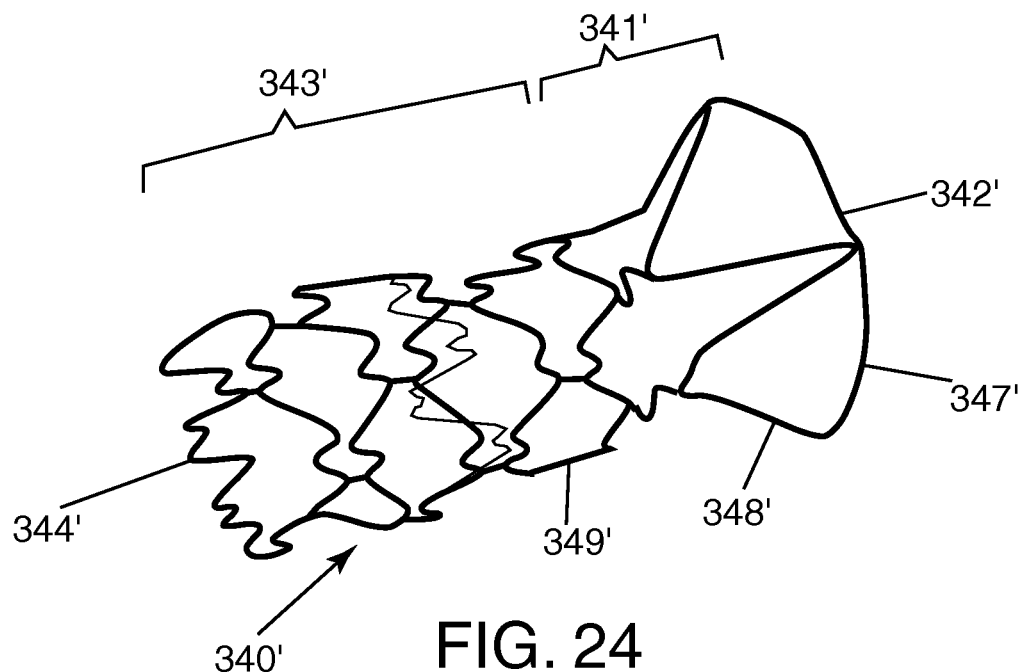
FIG. 24 is a perspective view of another embodiment of a stent expanded to an enlarged condition such one end of the stent is flared radially outwardly.

In addition, the stent 340 may include a plurality of additional bands of cells 349 defining a second portion 343 of the stent 340. Each of the additional bands of cells 349 may include axial elements 349a connected alternately to curved elements 349b, thereby defining a zigzag or serpentine and third axial length 349c. As shown in FIG. 23, the third axial length 349c may be substantially shorter than the second axial length 348c. Alternatively, the third axial length 349c may be substantially longer, shorter, or similar to the first axial length 347c and/or the second axial length 348c. The axial elements 349a may be substantially straight, as shown, or may have a curvilinear shape, such as that shown in FIG. 24.

Adjacent bands of cells 349 defining the second portion 343 of the stent 340 may be connected either directly or via links. For example, returning to FIG. 23, the band of cells 349-1 adjacent the second band of cells 348 may be connected directly to the second band of cells 348, e.g., at adjacent curved elements 348b, 349b. The next band of cells 349-2 are connected to the band of cells 349-1 by links 349d. Although the links 349d are shown being substantially straight, i.e., extending substantially parallel to the longitudinal axis 346, the links 349d may have other configurations, e.g., including curved elements defining at least a portion of a sinusoidal wave or other zigzag and the like (not shown), as described further below. In addition or alternatively, the length of the links 349d and/or the distance between the adjacent bands of cells 349 may be varied, if desired.

Although each of the bands of cells 349 in the second portion 343 of the stent 340 are shown having similar configurations and axial lengths 349c, it will be appreciated that the dimensions and configurations may be varied between the second band of cells 348 and the second end 344 of the stent 340, if desired. Thus, the portion of the stent 340 between the second band of cells 348 and the second end 344 of the stent may have a substantially homogenous cell structure or non-uniform cell and/or band configurations, e.g., as described further below. In addition, any number of annular bands 349 may be provided, e.g., such that the second portion 343 has a predetermined length corresponding to a length of a lesion being dilated or otherwise treated using the stent 340, e.g., between about three and twenty millimeters (3-20 mm). Alternatively, the second portion 343 of the stent 340 may include other configurations, similar to other embodiments described elsewhere herein.

Returning to FIGS. 21A and 21B, the stent 340 may be provided initially in the contracted condition shown in FIG. 21A, e.g., having a diameter between about one half and two millimeters (0.5-2 mm). The stent 340 may be delivered endoluminally, e.g., using a delivery apparatus, such as those described elsewhere herein. The stent 340 may then be expanded to the enlarged condition shown in FIG. 21B, e.g., using an internal balloon or other expandable member (not shown). In the enlarged condition, both of the first and second portions 341, 343 of the stent 340 define a circumference or other cross-sectional dimension that is larger than in the contracted condition. More particularly, the first portion 341 of the stent 340 may be expanded to assume a flared shape, e.g., having an outer diameter between about four and fifteen millimeters (4-15 mm), while the second portion 343 of the stent may be expanded to a generally uniform cylindrical shape, e.g., having a diameter between about two and seven millimeters (2-7 mm).

Turning to FIG. 22, the flared shape of the first portion 341 is shown in more detail, i.e., after the stent 340 has been expanded to the enlarged condition. Because of the difference in lengths between the first and second bands of cells 347, 348, the first portion 341 of the stent 340 flares radially outwardly as it expands. This flaring may be created by the mismatch of the first and second axial lengths 347c, 348c, i.e., because the first band of cells 347 are substantially shorter than the second band of cells 348. As the stent 340 expands, the axial elements 347a of the first band of cells 347 may be deflected from a substantially axial orientation in the contracted condition (as shown in FIG. 21A) to a substantially circumferential orientation, thereby reducing the curvature of the curved elements 347b at the first end 341 (as shown in FIGS. 21B and 22). This causes the axial elements 348a of the second band of cells 348 to expand to a greater diameter adjacent the first band of cells 347 than the third band 349-1, thereby causing the first portion 341 to flare radially outwardly. Thus, the first end 342 may have a diameter or other cross-sectional dimension that is substantially larger than the transition between the first and second portions 341, 343 and/or than the second end 344.

The stent 340 (or other embodiments described elsewhere herein) may be formed from a variety of materials that may be plastically deformed to allow expansion of the stent 340. For example, the stent 340 may be formed from metal, such as stainless steel, tantalum, MP35N, Niobium, Nitinol, and L605, plastic, or composite materials. In particular, the materials of the stent 340 may be plastically deformed under the pressures experienced when the stent 340 is expanded, e.g., such that the first and/or second portions 341, 343 of the stent 340 are deformed beyond their elastic limit. Thus, when the stent 340 is deployed, the stent 340 may maintain its enlarged condition (e.g., that shown in FIG. 21B) with minimal recoil. Stated differently, the stent 340 material may resist collapsing back towards its reduced configuration after deployment, e.g., if the tissue surrounding the body lumen attempts to constrict or otherwise return to its occluded shape.

Alternatively, at least a portion of the stent 340 may be self-expanding. For example, one or both of the first and second portions 341, 343 may be biased to expand at least partially outwardly yet may be constrained on a delivery device in a contracted condition to facilitate delivery. In this alternative, the stent 340 may be formed from Nitinol or other shape memory or superelastic materials.

The stent 340 may be formed from a tube of material having a solid wall initially. For example, portions of the tube may be removed, e.g., by laser cutting, etching, machining, and the like, to define the elements of the bands of cells and/or links. Alternatively, the stent 340 may be formed from a flat sheet and rolled into a tubular shape. For example, portions of the sheet may be removed and then the resulting cellular structure may be rolled and attached along its length, e.g., by welding, bonding, interlocking connectors (not shown), and the like. In other alternatives, the stent 340 may be a braided or other structure, e.g., formed from one or wires or other filaments braided or otherwise wound in a desired manner. Additional possible stent structures may include helical coil wires or sheets.

Optionally, the resistance of the stent 340 to expansion may be varied along its length. This performance of the stent 340 may be based upon mechanical properties of the material, e.g., which may involve heat treating one or more portions of the stent 340 differently than other portions. In addition or alternatively, the structure of the stent 340 may be varied, e.g., by providing struts, fibers, or other components in different portions having different widths, thicknesses, geometry, and the like, as described further below.

Figure 25:
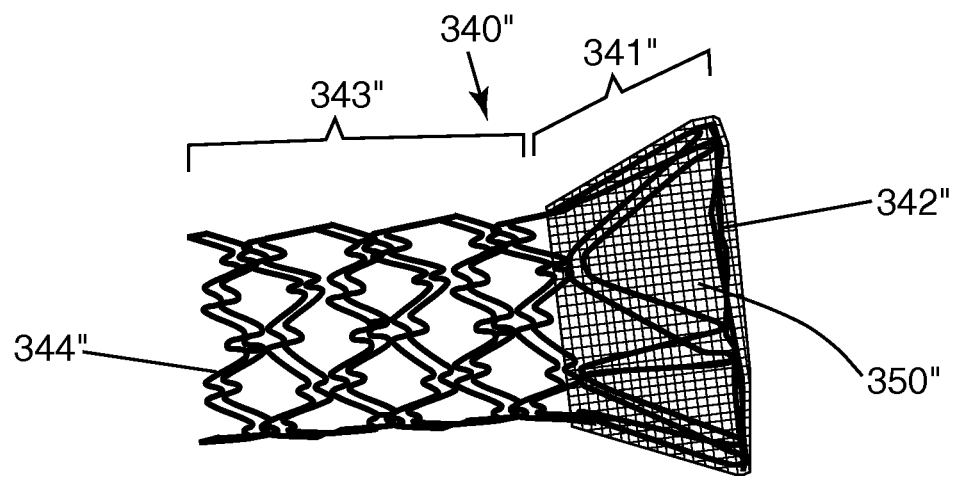
FIG. 25 is a side view of another embodiment of a stent including a flared first portion and an expanded second portion and including a membrane on the first portion.

If desired, one or more portions of the stent 340 (or other embodiments described elsewhere herein) may include a membrane, film, or coating (not shown), e.g., to create a nonporous, partially porous, or porous surface between cells of the stent 340. For example, as shown in FIG. 25, an alternative embodiment of a stent 340" is shown, that may be constructed and/or configured similar to other embodiments described herein (e.g., with like elements labeled with similar reference numbers followed by ""'"). The stent 340" may include a first flared portion 342" including a membrane 350" that may expand along with the first portion 342."

The membrane 350" may be formed from a relatively thin layer of material, e.g., PTFE, ePTFE, silicone, polyurethane, or polyethylene, that may be embedded into, coated onto, sandwiched around, or otherwise carried by the stent 340." The membrane 350" may be substantially elastic such that the membrane 350" may expand when the first portion 341" is flared or otherwise expanded. Alternatively, the membrane 350" may be folded or otherwise compressed such that the membrane 350" may unfold or otherwise to accommodate expansion as the stent 340" is expanded.

The membrane 350" may be provided on an outer and/or inner surface of the first portion 341." A membrane 350" on the inner surface may facilitate recrossing the stent 340" at a later time after implantation. For example, after the stent 340" is implanted within a patient, it may be desirable to advance a guidewire or other instrument (not shown) through the ostium into the branch vessel, e.g., to perform another procedure. This may occur during the same surgical procedure, or some time after the patient has recovered, e.g., when the branch vessel, lesion, or main vessel need subsequent treatment. The membrane 350" may prevent the tip of a guidewire or other instrument from catching or tangling in the struts, wires, cells, or other structures of the stent 340." Instead, the membrane 350" may provide a substantially smooth, possibly lubricious surface that may guide a guidewire through the stent 340" into the branch vessel.

In addition or alternatively, a membrane 350" on the stent 340" may carry therapeutic or other compounds or materials. For example, a membrane 350" on an outer surface of the stent 340" may be pressed into contact with the plaque, damaged tissue, or other material of the lesion, allowing the compound to act to enhance healing or otherwise treat the lesion.

Optionally, any of the stents described herein may include one or more radiopaque or other markers (not shown), e.g., to facilitate monitoring the stent during advancement, positioning, and/or expansion. For example, with reference to FIGS. 21A and 21B, radiopaque material, e.g., gold, platinum, iridium, tungsten, or their alloys, may be provided on each end 342, 344 of the stent 40 and/or adjacent the transition between the first and second portions 341, 343. In addition or alternatively, wires, rods, disks, or other components (not shown) may be provided on predetermined locations on the stent 340 that are formed from radiopaque material to facilitate monitoring the stent 340 using fluoroscopy or other external imaging.

In addition or alternatively, the stent 340 (or other embodiments described herein) may carry one or more therapeutic or other compounds (not shown) that may enhance or otherwise facilitate treatment of a target location within a patient's body. For example, the stent 340 may carry compounds that prevent restenosis at the target location.

Turning to FIGS. 26A-26F, another exemplary embodiment of an apparatus 310 is shown for delivering a stent 340 (which may be any of the embodiments described herein), e.g., into an ostium or other bifurcation 90 where a branch lumen extends from a main lumen 92. Generally, the apparatus 310 includes a catheter or other elongate tubular member 312 having a proximal end (not shown), a distal end 316, and one or more lumens 318 extending between the proximal end and distal end 316, thereby defining a longitudinal axis 320 therebetween. One or more balloons or other expandable members 322 are provided on the distal end 316, e.g., a first proximal balloon 322a and a second distal balloon 322b as shown.

The catheter 312 may include a plurality of lumens 318 extending between the proximal end (e.g., from a handle thereon, not shown) and the distal end 316. For example, the catheter 312 may include an instrument lumen (not shown) that extends from the proximal end to an opening in the distal tip 317. The instrument lumen may have sufficient size to allow a guidewire 98 or other rail or instrument (not shown) to be inserted therethrough, e.g., to facilitate advancing the catheter 312 over the rail, as explained further below. Optionally, the proximal end (or handle) may include one or more seals (not shown), e.g., a hemostatic seal that prevents fluid, e.g., blood, from flowing proximally out of the instrument lumen, yet allows one or more instruments to be inserted therethrough and into the instrument lumen.

In addition, the catheter 312 may include inflation lumens (not shown) that extend from respective ports in the proximal end (or handle) through the catheter 312 to openings communicating within an interior of a respective balloon 322a, 322b. A source of inflation media and/or vacuum, e.g., a syringe filled with saline (not shown), may be connected to the handle for expanding and/or collapsing the balloons 322. Additional information on apparatus and/or methods that may be used to deliver a stent may be found in co-pending application Ser. No. 11/136,266, filed May 23, 2005, incorporated by reference above.

As shown in 26A-26C, the apparatus 310 may initial carry a stent 340, such as any of the embodiments described elsewhere herein. The stent 340 may be mounted around the distal end 316 of the catheter 312, e.g., such that a first portion 341 of the stent 340 at least partially surrounds the proximal balloon 322a and a second portion 343 of the stent 340 surrounds the distal balloon 322b. Optionally, the apparatus 310 may include a sheath or other cover (not shown) that may surround or otherwise cover the stent 340. The sheath may be removable from over the proximal or distal portions 341, 343 of the stent 340 or the entire stent 340 to expose the stent 340 before deployment, as described further below.

Turning to FIGS. 26A-26F, an exemplary method is shown for delivering the stent 340 into an ostium 90, e.g., using an apparatus 310, which may be any of the embodiments described herein. The ostium 90 may be an opening in a wall of a first or main body lumen 92 that communicates with a second or branch body lumen 94, similar to other embodiments described elsewhere herein. An occlusion or other lesion 96 may exist at and/or adjacent to the ostium 90, e.g., extending at least partially into the branch 94. The lesion 96 may include atherosclerotic plaque or other material that partially or completely occludes blood or other fluid flow between the main body lumen 92 and the branch 94.

Figure 26A:
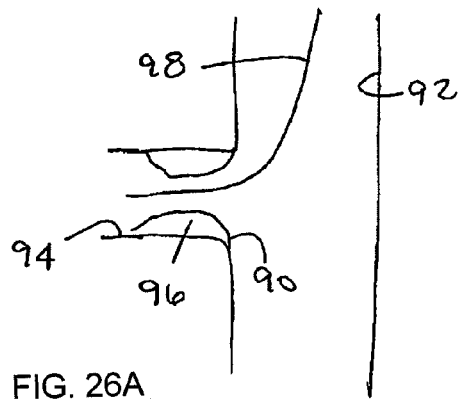
FIGS. 26A-26F are cross-sectional views of a patient's body, showing a method for implanting a stent at a bifurcation.

Initially, as shown in FIG. 26A, a guidewire 98 or other rail may be introduced from the main body lumen 92 through the ostium 90 into the branch 94. As shown, the lesion 96 at the ostium 90 partially occludes the ostium 90 and extends into the branch 94. The guidewire 98 may be placed using conventional methods. For example, a percutaneous puncture or cut-down may be created at a peripheral location (not shown), such as a femoral artery, carotid artery, or other entry site, and the guidewire 98 may be advanced through the patient's vasculature from the entry site, e.g., alone or with the aid of a guide catheter or sheath (not shown).

After the guidewire 98 is directed into the branch 94 beyond the lesion 96, it may be desirable to at least partially dilate the lesion 96. For example, a balloon or other dilatation catheter (not shown) may be advanced over the guidewire 98 into and through the lesion 96, whereupon a balloon or other element on the catheter may be expanded to at least partially dilate the lesion 96. If desired, other procedures may also be performed at the lesion 96, e.g., to soften, remove, or otherwise treat plaque or other material forming the lesion 96, before the stent 340 is implanted. After completing any such procedures, instruments advanced over the guidewire 98 may be removed.

Optionally, a guide catheter (not shown) may be advanced over the guidewire 98 into the main body lumen 92, e.g., until a distal end of the guide catheter is disposed adjacent or proximal to the ostium 90. The guide catheter may be used to advance one or more instruments (such as those just described) over the guidewire 98 and into the main body lumen 92 and/or branch body lumen 94. In addition, the guide catheter may facilitate advancement of the apparatus 310 into the main body lumen 92 and/or into the branch 94, in addition to or instead of the guidewire 98.

Figure 26B:
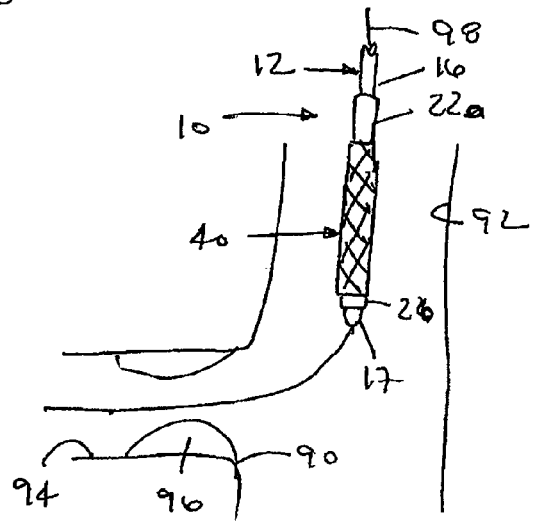
Figure 26C:
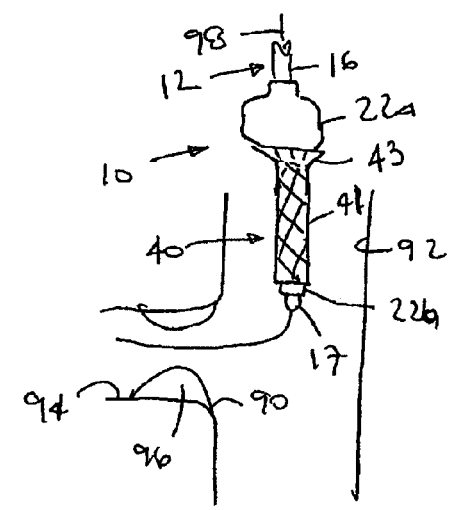

Turning to FIG. 26B, a distal end 316 of apparatus 310 may be advanced over the guidewire 98 (and/or through the guide catheter, not shown) from the entry site into the main body lumen 92 with the balloons 322 in their contracted conditions. When the distal tip 317 is adjacent to the ostium 90, as shown in FIG. 26C, the proximal balloon 322a may be expanded, for example, by delivering saline, nitrogen, or other inflation media into the interior of the proximal balloon 322a, e.g., from a syringe or other fluid source (not shown) coupled to the proximal end (also not shown) of the apparatus 310. As the proximal balloon 322a is expanded, a first portion 341 of the stent 340 is expanded, e.g., into a flared configuration.

Alternatively, the apparatus 310 may be advanced initially with the stent 340 and balloons 322 collapsed until the stent 340 passes entirely through the lesion into the branch vessel 94, e.g., to ensure that the stent 340 may be advanced sufficiently into the ostium 90. The apparatus 310 may then be retracted until at least the proximal balloon 322a is disposed within the main vessel 92, whereupon the proximal balloon 322a may be expanded as described above.

Figure 26D:
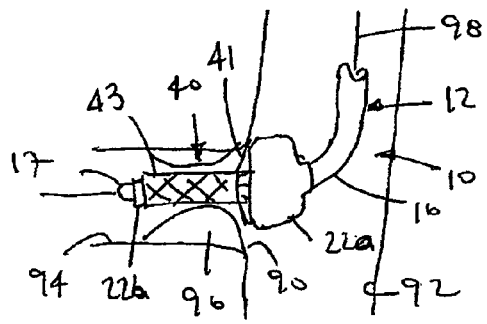

Turning to FIG. 26D, with the first portion 341 flared or otherwise expanded, the apparatus 310 may be advanced distally over the guidewire 98 into the ostium 90, e.g., until the first portion 341 contacts the wall of the main body lumen 92 surrounding the ostium 90. As the apparatus 310 is advanced, the distal tip 317 of the catheter 312 enters the ostium 90 and passes through the lesion 96 into the branch 94, e.g., until the second portion 343 of the stent 340 is disposed within the lesion 96, as shown. Optionally, if the stent 340 includes one or more radiopaque markers, fluoroscopy or other external imaging may be used to ensure that the stent 340 is positioned properly into the ostium 90 and branch 94.

Figure 26E:
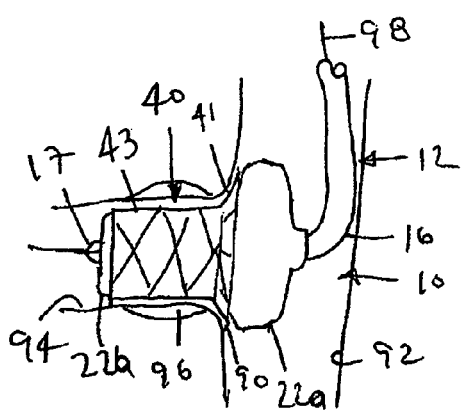

Turning to FIG. 26E, with the second portion 343 disposed within the lesion 96, the distal balloon 322b may be expanded, thereby dilating or otherwise lining the branch 94 within the lesion 96. For example, as the second portion 343 of the stent 340 is expanded, plaque and/or other material defining the lesion 96 may be directed radially outwardly to dilate the lesion 96 to a diameter comparable to the branch 94 downstream of the lesion 96. Again, if the stent 340 and/or apparatus 310 include one or more radiopaque markers or if contrast is delivered into the main body lumen 92 and/or into the branch 94, the ostium 90 and/or lesion 96 may be imaged to confirm the position of the stent 340 and/or to monitor the extent of dilation of the lesion 96, e.g., until a desired diameter or other cross-section is attained.

Optionally, additional distal force may be applied to the apparatus 310, e.g., to force the first portion 341 of the stent 340 against the ostium 90. This pushing may cause the first portion 341 to plastically deform further, e.g., to at least partially conform to the shape and/or contour of the ostium 90. This additional force may be applied before, during, or after inflation of the distal balloon 322b.

In addition or alternatively, if the proximal balloon 322a is elastically expandable, the proximal balloon 322a may be expanded initially (e.g., during the stage described with reference to FIGS. 26C and 26D) to a first enlarged configuration to allow the first portion 341 of the stent 340 to contact and/or otherwise seat into the ostium 90. Once the distal balloon 322b is inflated to expand the second portion 343 of the stent 340 and dilate the lesion 96 to a desired extent (e.g., as described with reference to FIG. 26E), the proximal balloon 322a may be inflated further, e.g., to further expand the first portion 341 of the stent 340 or cause the first portion 341 to conform further to the contour of the ostium 90. This additional expansion may further seat and/or secure the stent 340, and/or to dilate the ostium 90.

Alternatively, the distal balloon 322b may be at least partially expanded before expanding the proximal balloon 322a. In a further alternative, the stent 340 may be positioned in the ostium 90 before expanding either balloon 322. For example, radiopaque markers (not shown) on the stent 340 and/or delivery apparatus 310 may be monitored using fluoroscopy to facilitate positioning the stent 340. Once the stent 340 is properly positioned, the balloons 322 may be expanded, e.g. simultaneously or sequentially as described above. For example, the distal balloon 322b may be expanded first to anchor the stent 340 in the branch 94, e.g., as described elsewhere herein.

Figure 26F:
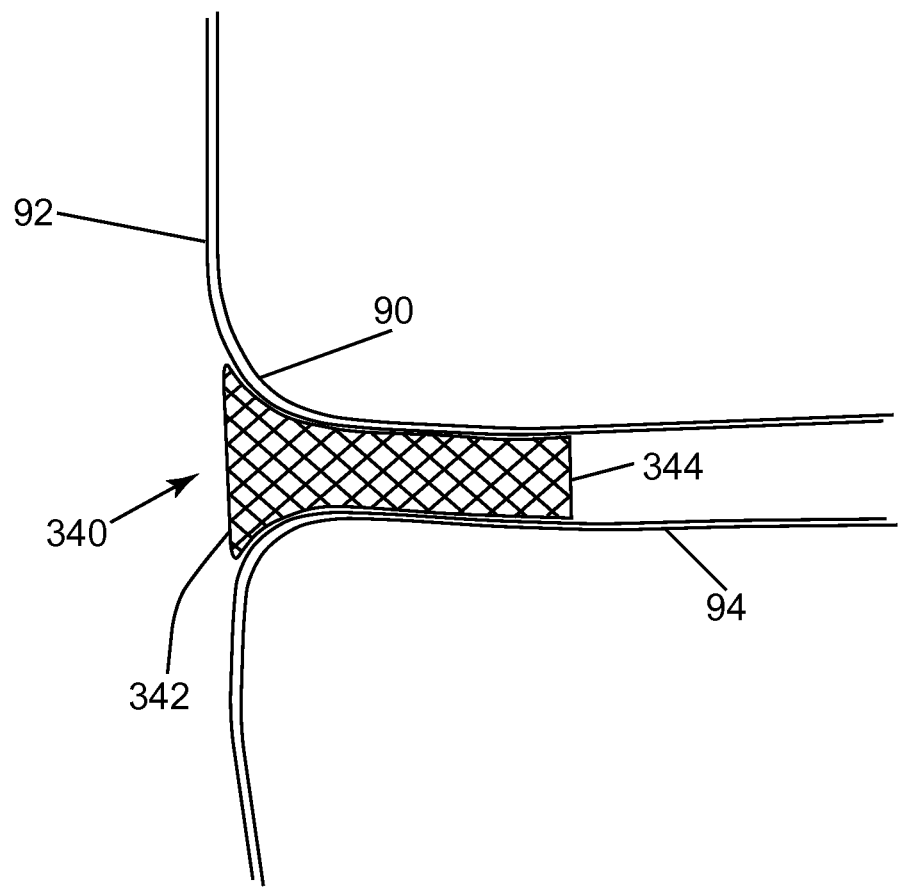

Turning to FIG. 26F, once the stent 340 is expanded and/or positioned in a desired manner, the balloons 322 may be collapsed, e.g., by evacuating the inflation media using a syringe or other device (not shown) at the proximal end (also not shown) of the catheter 312. The balloons 322 may be deflated simultaneously or sequentially, e.g., first deflating the distal balloon 322b, and then deflating the proximal balloon 322a (e.g., optionally after applying further distal force, if desired). With the balloons 322 collapsed, the apparatus 310 is withdrawn from the main body lumen 92 and out of the patient's body. If a guide catheter or other sheath (not shown) is used, the guide catheter or sheath may be advanced against or into the ostium 90 before the apparatus 310 is removed, e.g., to facilitate withdrawing the balloons 322 without dislodging the stent 340. The guidewire 98 (and/or the guide catheter or sheath, if used) may be removed before, after, or simultaneously with the apparatus 310. Thus, the stent 340 remains in place to dilate the lesion 96.

Other apparatus and methods for delivering a stent 340, such as any of those described herein, may be found in applications Ser. Nos. 11/419,997 and 11/439,717, both filed May 23, 2006, the entire disclosures of which are expressly incorporated by reference herein. For example, application Ser. No. 11/419,997 discloses various locator devices that may be provided on or with the apparatus 310 to facilitate locating the ostium and/or positioning the stent during delivery.

Figure 27A:
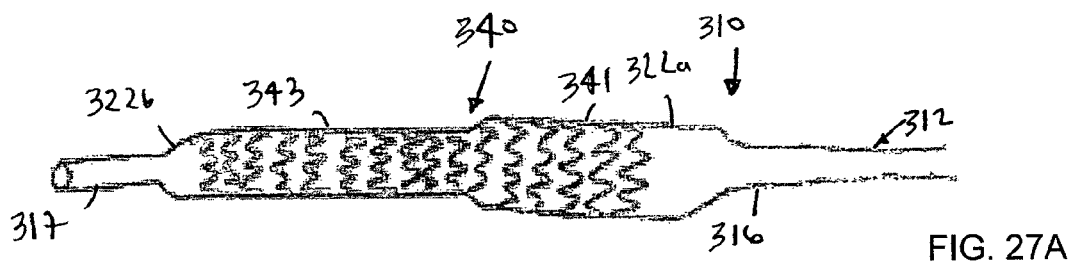
FIGS. 27A-27F are cross-sectional views of a patient's body, showing another method for implanting a stent at a bifurcation.
Figure 27B:
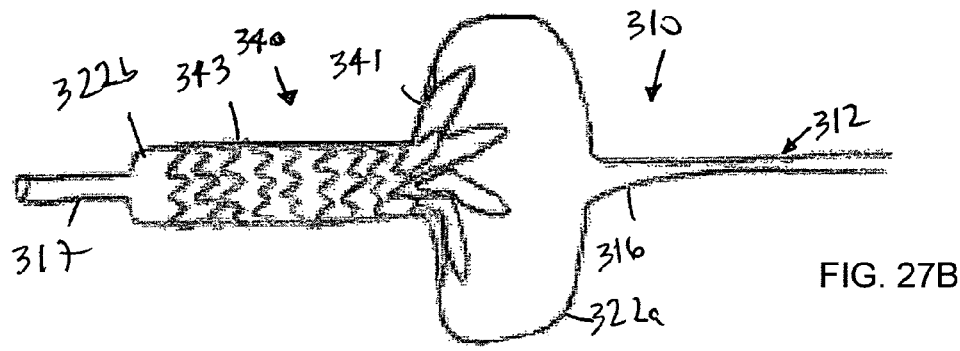

Turning to FIGS. 27A-27F, another method is shown for delivering a stent 340 into a bifurcation 90, similar to those described elsewhere herein. FIG. 27A shows the stent 340 in its contracted condition mounted on a distal end 316 of a catheter 312. Turning to FIG. 27B, after being delivered to a location adjacent the bifurcation, a proximal balloon 322a may be inflated to a predetermined size to expand and/or flare a first portion 341 of the stent 340. As shown, the first portion 341 may be over-flared, i.e., plastically deformed or otherwise flared to a greater angle than the shape of the corresponding ostium into which the stent 340 is being delivered. For example, the first portion 341 may be flared close to or even beyond ninety degrees (90°) relative to longitudinal axis 320.

Figure 27C:
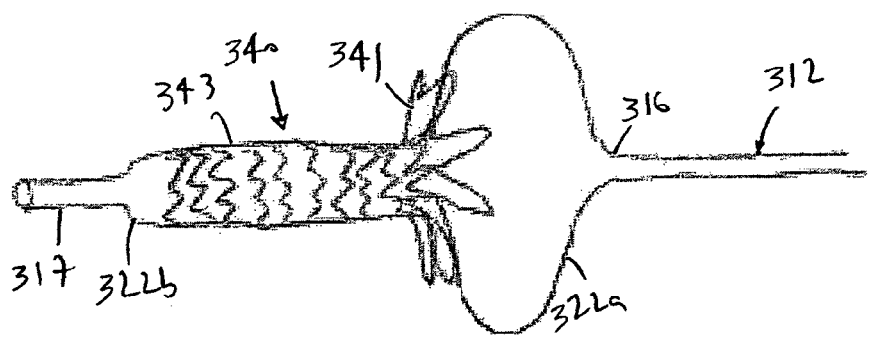

Turning to FIG. 27C, after expansion and/or flaring, the proximal balloon 322a may be partially deflated, e.g., such that the flared first portion 341 of the stent 340 is removed from the surface of the proximal balloon 322a.

Figure 27D:
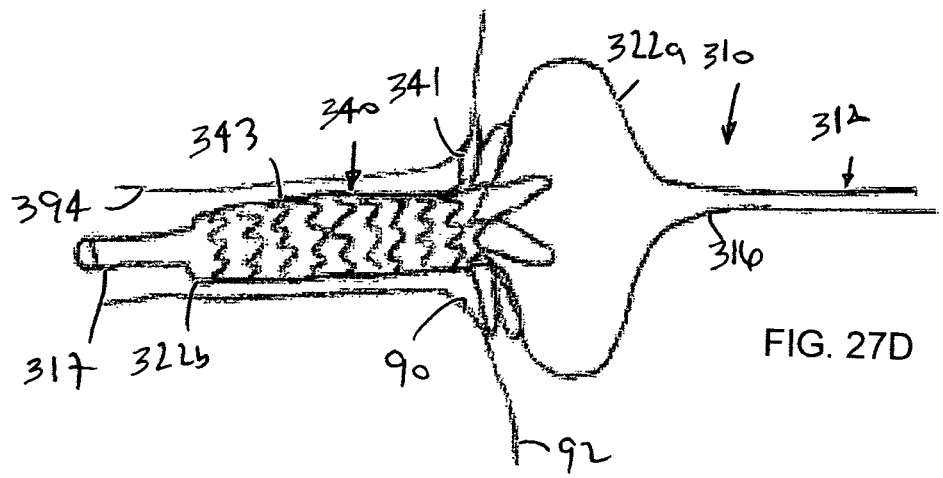

Turning to FIG. 27D, the distal end 316 of the catheter 312 may be inserted into the branch vessel 94, e.g., over a guidewire (not shown), similar to the embodiments described elsewhere herein. Because of the over-flaring, the first portion 341 of the stent 340 may be advanced into the ostium 90 with sufficient force to cause the first portion 41 to become slightly less flared, i.e., causing the first portion 341 to conform at least partially to the shape of the ostium 90. This advancement force may impose an elastic load on the first portion 341, which may enhance apposition and/or anchoring of the stent 340 relative to the ostium 90.

Figure 27E:
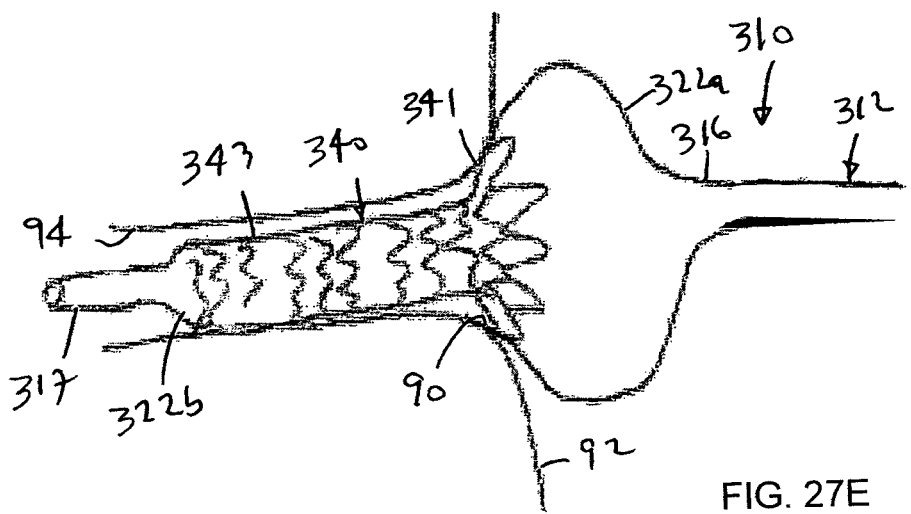
Figure 27F:
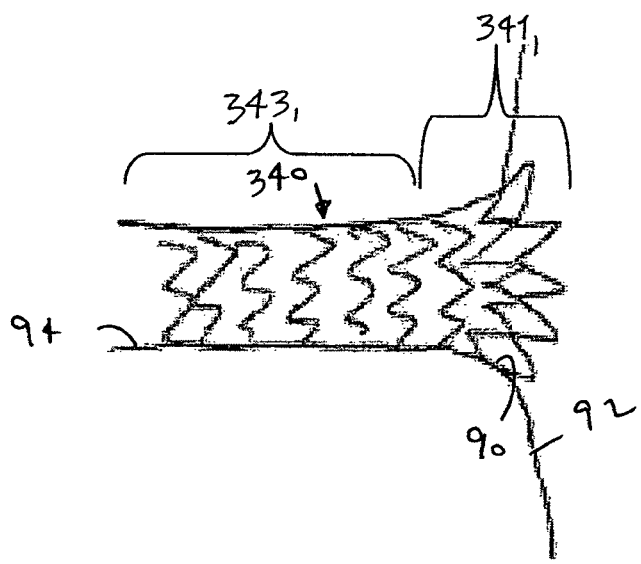

Turning to FIG. 27E, the apparatus 310 may be advanced to substantially seat the stent 340 in the ostium 90, whereupon the distal balloon 322b may be inflated to expand the second portion 343 of the stent 340, as shown in FIG. 27F. The balloons 322 may then be collapsed and the apparatus 310 removed from the ostium 90 and the patient's body, leaving the stent 340 in the ostium 90.

Optionally, with additional reference to FIG. 27F, if desired, the first and second portions 341, 343 of the stent 340 may be tempered to different degrees, e.g., to enhance the ability of the first portion 341 to hold a spring force upon advancement into the ostium 90. For example, the second portion 343 may be annealed, while the first portion 341 may be relatively harder, i.e., allowing a greater buildup of elastic deformation before plastic deformation occurs. Alternatively, the entire stent 340 may be hardened to a greater temper.

Figure 28A:
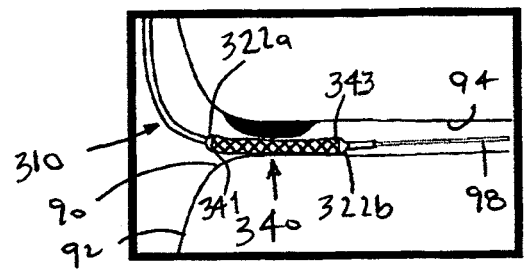
FIGS. 28A-28D are cross-sectional views of a patient's body, showing yet another method for implanting a stent at a bifurcation.

Turning to FIGS. 28A-28D, yet another method for delivering a stent 340 into an ostium 90 where a branch vessel 94 extends from a main vessel 92. In this embodiment, a distal portion of the distal balloon 322b may be expanded first to substantially anchor the stent 340 within the branch vessel 94 before the proximal portion of the stent 340 is expanded. Initially, as shown in FIG. 28A, the apparatus 310 may be advanced through the patient's vasculature and positioned such that the stent 340 extends into the ostium 90, e.g., using external imaging, locators (not shown) on the apparatus 310, and the like, similar to other embodiments described herein.

Figure 28B:
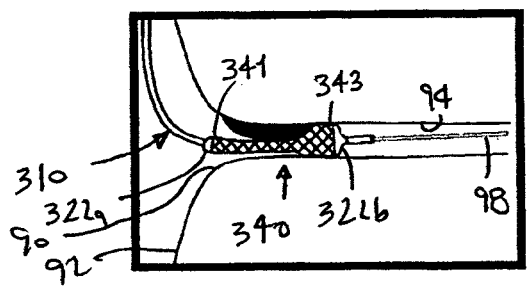
Figure 28C:
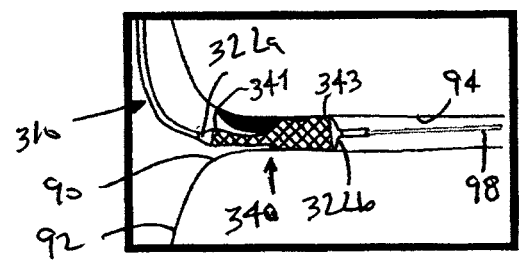

Turning to FIG. 28B, the distal balloon 322b may be inflated, which may cause the distal portion of the distal balloon 322b to inflate first, as shown, e.g., due to the lower resistance to expansion of the distal portion 343 of the stent 340. As the distal portion 343 of the stent 340 expands, it engages the wall of the branch 94, thereby gaining traction that may prevent or reduce migration of the stent 340. As shown in FIG. 28C, as the distal balloon 322b is expanded, the distal portion 343 of the stent 340 and distal balloon 322b may expand in the direction of the main lumen 92, thereby increasing traction and resistance of the stent 340 to migration, thereby substantially stabilizing the stent 340 relative to the ostium 90.

Figure 28D:
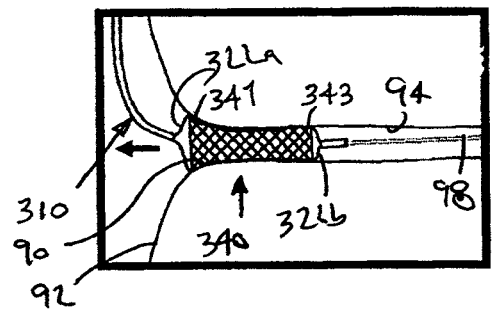

Turning to FIG. 28D, the proximal balloon 322a may be inflated to expand and flare the proximal portion 341 of the stent 340. As represented by arrow "A," expansion of the proximal portion 341 of the stent 340 may apply a proximal force on the stent 340. However, the traction provided by the expanded distal portion 343 may resist proximal movement, and allow the proximal portion 341 to flare and expand without causing the stent 340 to migrate. Optionally, the distal balloon 322b and/or proximal balloon 322a may be expanded further simultaneously or separately, similar to other embodiments described herein.

In an alternative embodiment, a separate balloon or other expandable member (not shown) may be provided on the apparatus 310, e.g., distally beyond the distal balloon 322b. This balloon may be inflated after positioning the apparatus 310 and stent 340 in the ostium to secure the apparatus 310, similar to the distal balloon 322b, as described above. The balloon may remain inflated until after the stent 340 is fully expanded, and then deflated before the apparatus 310 is removed.

Figure 29:
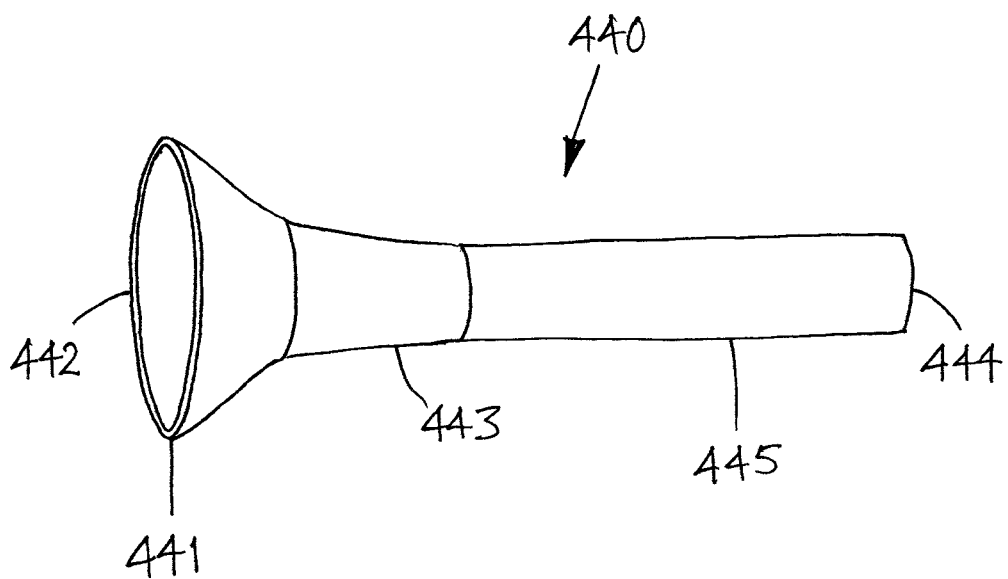
FIG. 29 is a perspective view of another embodiment of a flared stent including multiple portions having different mechanical properties.

Turning to FIG. 29, another embodiment of a stent 440 is shown that includes multiple portions having different properties than one another. Generally, the stent 440 is expandable from a contracted condition to an enlarged condition, similar to the embodiments described elsewhere herein. In the embodiment shown, the stent 440 includes a first portion 441 adjacent a first end 442, a second intermediate portion 443, and a third portion 445 adjacent a second end 444. The first portion 441 may include one or more bands of cells configured to expand and flare, e.g., similar to other embodiments described herein. Thus, the first portion 441 may be configured for delivery into an ostium (not shown) immediately adjacent a main lumen (also not shown). The first portion 441 may be relatively stiff compared to the second and third portions 443, 445, e.g., to resist elastic recoil of the ostium, e.g., after delivering the stent 440 into the ostium, as described further below.

The second, intermediate portion 443 may be relatively flexible compared to the first and third portions 441, 445, e.g., to provide a flexible transition, e.g., if a branch lumen (not shown) extends transversely other than perpendicularly from the main lumen. Thus, the intermediate portion 443 may accommodate a bend in the stent 440 between the first and third portions 441, 445 without substantial risk of kinking or otherwise significantly compromising the lumen through the stent 440. In addition, the second portion 443 may be relatively short compared to the third portion 445, e.g., such that the second portion 443 does not extend substantially into the branch lumen. For example, the second portion 443 may include a plurality of links or other flexible connectors (not shown), e.g., similar to those shown and described with reference to FIGS. 4A-6E. Alternatively, the second portion 443 may include one or more bands of cells (not shown), e.g., having relatively thin or otherwise flexible elements, similar to exemplary cell structures described elsewhere herein.

The third portion 445 may be relatively longer than the first and second portions 441, 443. The mechanical properties of the third portion 445 may be balanced, e.g., to provide desired hoop strength to reinforce the branch lumen while providing sufficient flexibility to facilitate delivery, similar to other embodiments described herein.

Figure 31:
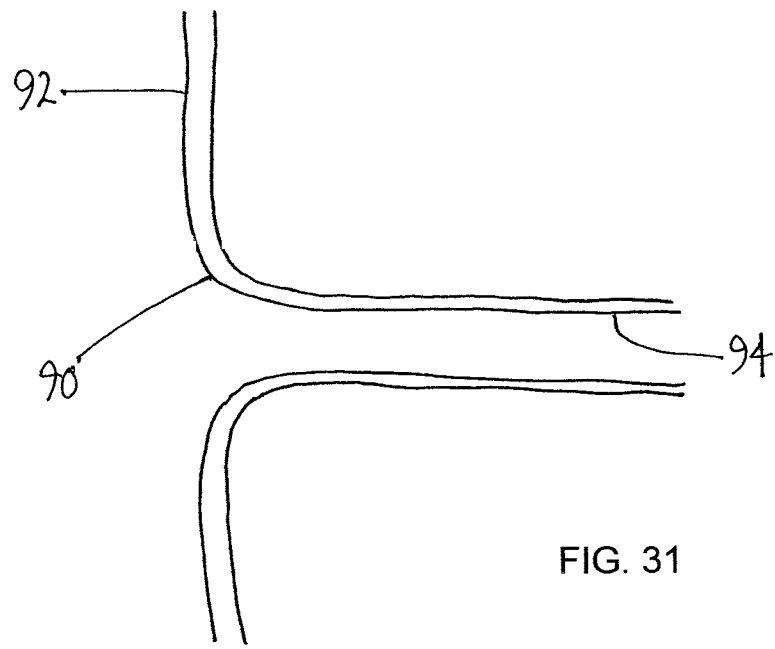
FIG. 31 is a cross-sectional view of a bifurcation where a branch vessel extends from a main vessel.
Figure 32:
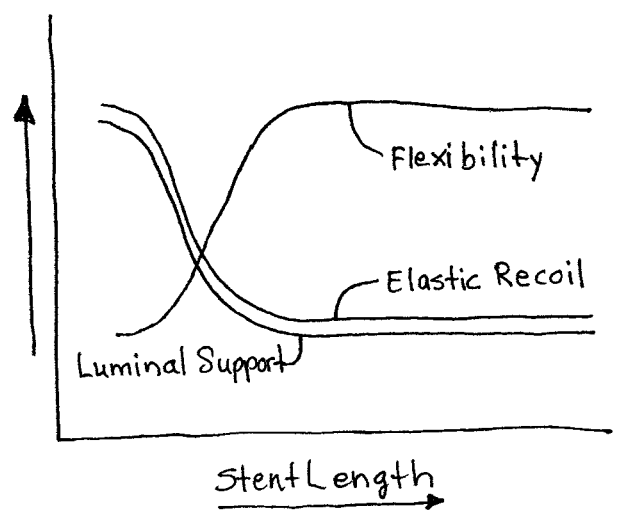
FIG. 32 is a graph showing exemplary desirable mechanical properties of a stent that may be implanted in the bifurcation of FIG. 31.

Turning to FIGS. 31 and 32, an exemplary bifurcation is shown, including an ostium 90 communicating between a main lumen 92 and a branch lumen 94. As explained elsewhere herein, the ostium 90 and/or branch lumen 94 may include plaque or other stenotic material (not shown) that may at least partially occlude the ostium 90. The desired properties for a stent to be deployed in such an ostium may be varied along its length, as just explained. In contrast, stents that are delivered into a non-bifurcated body lumen are generally designed to have substantially uniform properties along their lengths. Such uniformity is generally undesirable in a stent intended for delivery in a bifurcation.

For example, as shown in FIG. 31, the wall thickness of a bifurcation may vary between the main lumen 92 and the branch lumen 94. As shown, the wall thickness in the main lumen 92 may be substantially greater than the branch lumen 94. Thus, even if the ostium 90 is dilated, the thicker wall may create greater risk of recoil, i.e., of the wall at the ostium 90 being biased to constrict again after dilation. FIG. 32 graphically depicts the properties of a stent that may be desired given this problem. For example, line "R" represents the elastic recoil that the vessel wall may exhibit at the bifurcation. As shown, the recoil is greater immediately adjacent the main lumen 92 at least partially because of the greater wall thickness. The elastic recoil reduces into the ostium 90, and may have a substantially uniform recoil within the branch lumen 94 where the wall is located away from the ostium 90 that is substantially less than at the ostium 90.

To overcome this recoil, line "S" represents the luminal support desired for the stent along its length. Thus, it may be desirable to provide greater luminal support or rigidity upon expansion at the first end of the stent immediately adjacent the main lumen 92, and provide a lesser but substantially uniform rigidity within the branch lumen 94 away from the ostium 90. Conversely, line "F" represents the desired flexibility that may be desired for the stent along its length.

Figure 30:
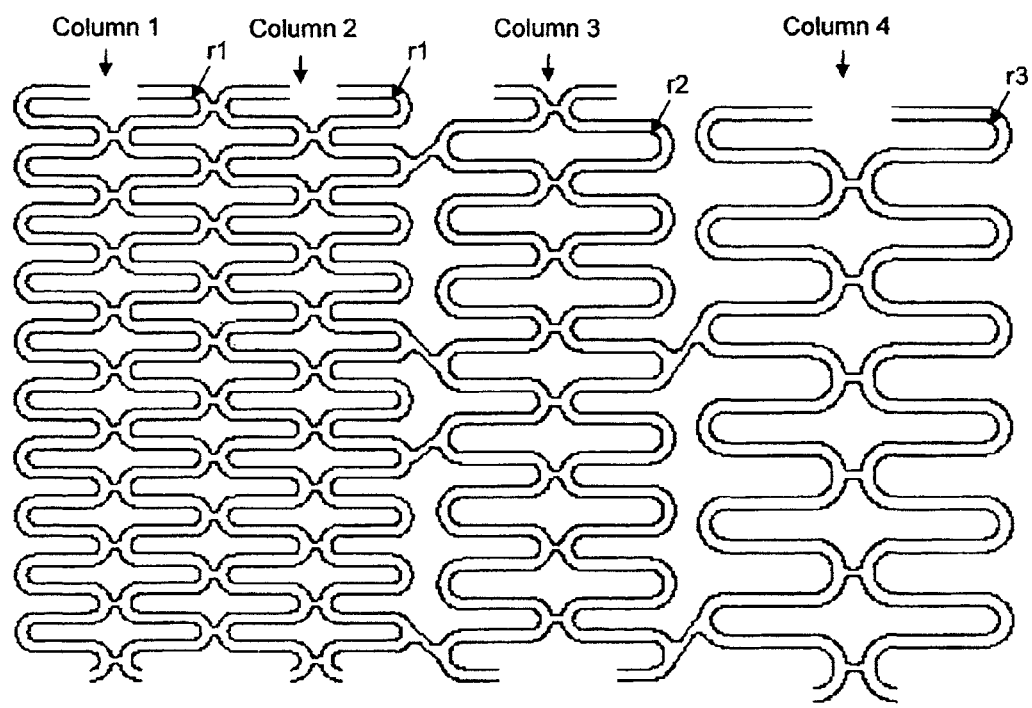
FIG. 30 is a top view of a portion of a cell pattern for a stent having variable properties along its length.

FIGS. 30 and 33-36 show various embodiments of cell patterns that may be provided that have variable mechanical properties along a length of a stent including the respective patterns. For example, FIG. 30 shows an embodiment of a stent structure having four different set of bands of cells. As shown, columns 1 and 2 include zigzag patterns having a shorter period than columns 3 and 4. Stated differently, columns 1 and 2 include more axial and curved elements disposed around a circumference of the stent than columns 3 and 4. Because of these differences, the bands of cells in columns 1 and 2 my have greater luminal support and/or less flexibility than the bands of cells in columns 3 and 4.

In addition, columns 1 and 2 are connected together using relatively short axial links extending between every adjacent curved element. These connections may also increase the support and/or reduce the flexibility in columns 1 and 2. In contrast, columns 2 and 3 and columns 3 and 4 are connected intermittently by longer diagonal links. These connections may increase flexibility in these columns.

Figure 33:
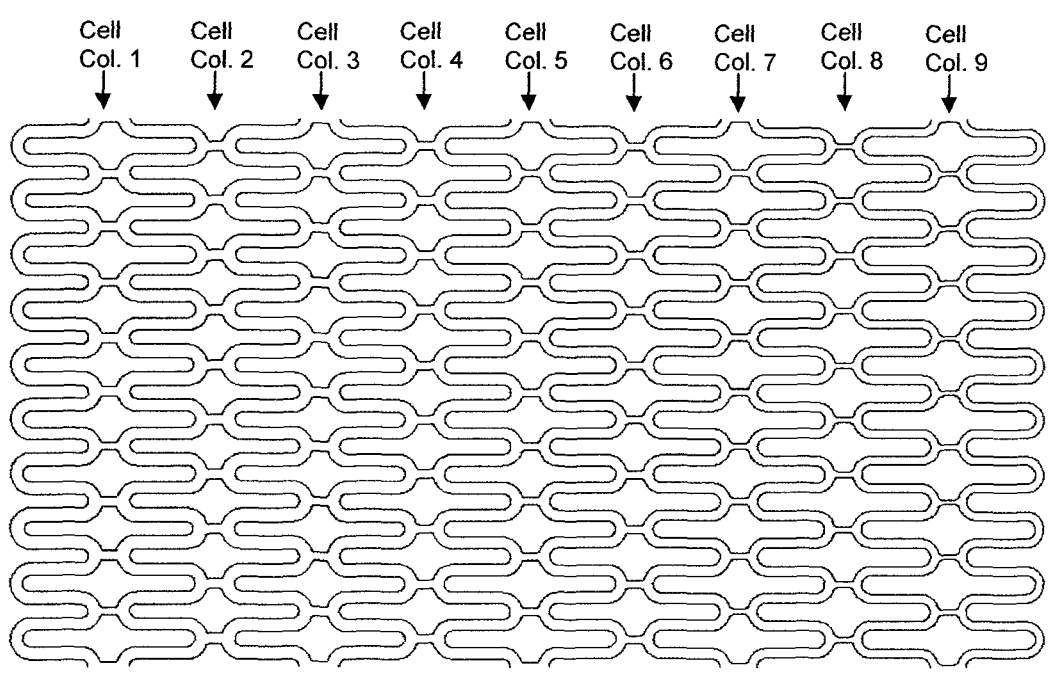

Turning to FIG. 33, another embodiment of a stent structure including a plurality of bands of cells disposed along a length of the stent. In this embodiment, the axial and curved elements defining the cells have similar length and spacing in each of the columns. However, the width or thickness of the axial and curved elements and/or links varies along the length of the stent. As shown, the thickness of the axial and curved elements and links is reduced from column 1 to column 9. This effectively reduces the luminal support from column 1 to column 9, while increasing flexibility.

Figure 34:
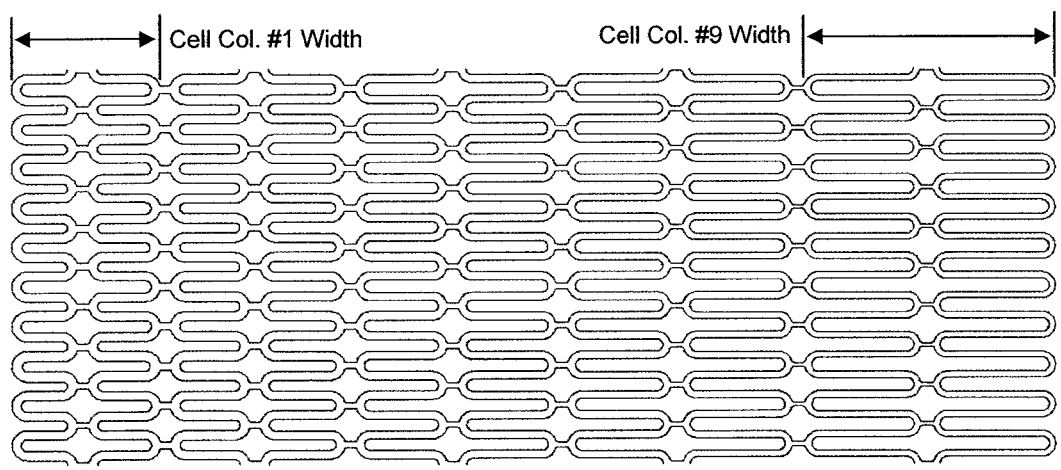

Turning to FIG. 34, another embodiment of a stent structure is shown having variable properties along its length. In this embodiment, the axial elements are longer at column 9 than at column 1. This configuration may also reduce the luminal support and/or increase flexibility from column 1 towards column 9. In addition, the thickness of the axial and curved elements and links may be reduced from column 1 to column 9, similar to the embodiment shown in FIG. 33.

Figure 35:
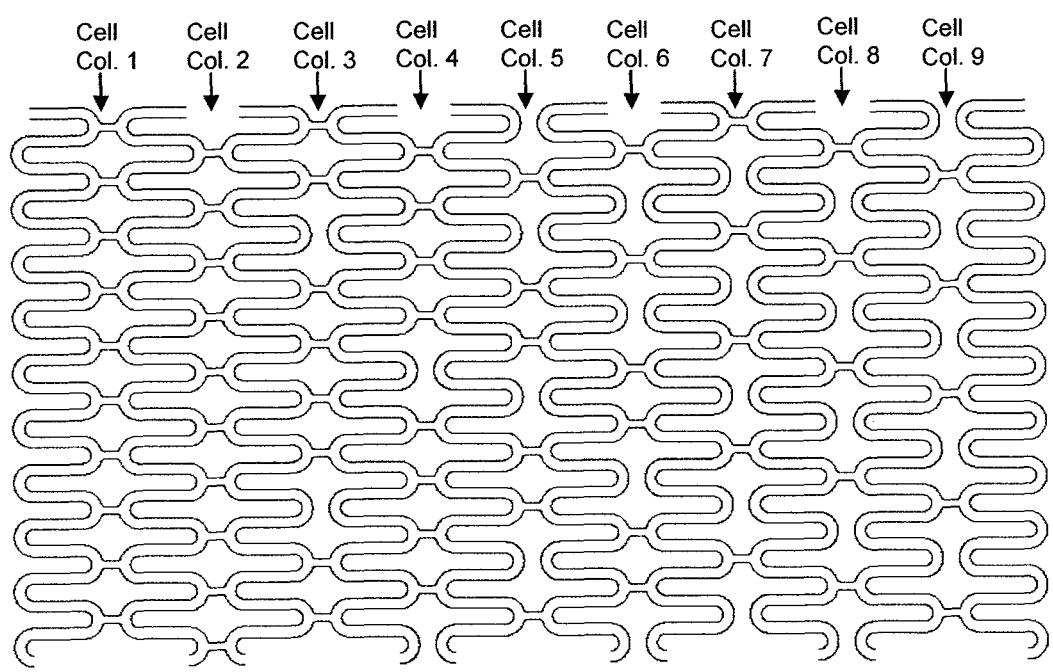

Turning to FIG. 35, yet another embodiment of a stent structure is shown that includes different numbers of links along its length. As shown, the bands of cells adjacent columns 1 and 2 include links connecting every adjacent curved element. Subsequent bands of cells towards column 9 include intermittent links, progressively increasing flexibility towards column 9. For example, the bands of cells adjacent columns 3 and 4 are missing one in every five links, the bands of cells adjacent column 5 are missing one in every three links, and the bands of cells adjacent columns 6-9 are missing every other link.

Turning to FIG. 36, still another embodiment of a stent structure is shown having different links between adjacent bands of cells between columns 1 and 9. As shown, columns 1 and 2 do not include links; instead adjacent curved elements are connected directly to one another, thereby providing relatively strong luminal support and reduced flexibility. Columns 4-6 include progressively longer axial links, while columns 7-9 include curved links, which may increase flexibility. The links in columns 7 and 8 have a slight curvature, e.g., defining an obtuse angle, while the links in column 9 have greater curvature, e.g., defining close to a ninety degree angle. Alternative embodiments of curved links including more complicated geometries are shown in FIGS. 36A-36C, e.g., including sinusoidal shapes.

Although different configurations are shown in these embodiments, it will be appreciated that various combinations of these features and configurations may be possible to provide a desired variability along the length of a stent, e.g., for delivery into an ostium, as described above.

Figure 37:
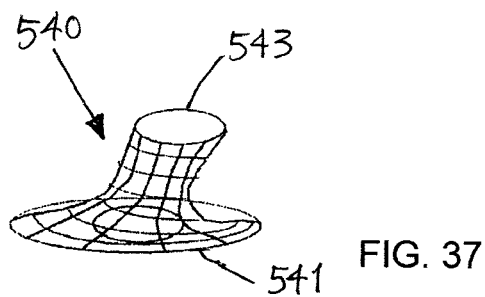
FIG. 37 is a perspective view of a rivet stent.
Figure 38A:
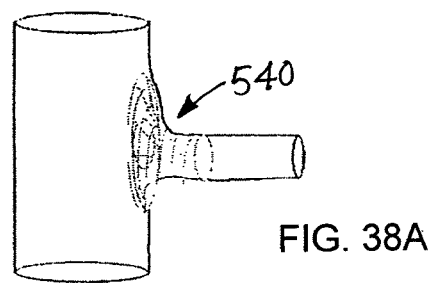
FIGS. 38A and 38B are cross-sectional views of a bifurcation where a branch vessel extends from a main vessel, showing a method for treating the bifurcation using the rivet stent of FIG. 37.

Turning to FIG. 37, another embodiment of a flared stent 540 is shown, which may be generally constructed similar to other embodiments described herein. Unlike previous embodiments, the stent 540 may have a relatively short length, e.g., such that the stent 540 may be deployed into an ostium 90 without extending substantially into the branch lumen 94, as shown in FIG. 38A. For example, the stent 540 may include a proximal or flaring portion 541 and a distal or substantially straight portion 543, which may be connected by flexible connectors and/or a flexible intermediate portion (not shown). The distal portion 543 may have a similar or shorter length than the proximal portion 541, or may have a length greater than the proximal portion 541, but less than two or three times the length of the proximal portion 541.

Figure 38B:
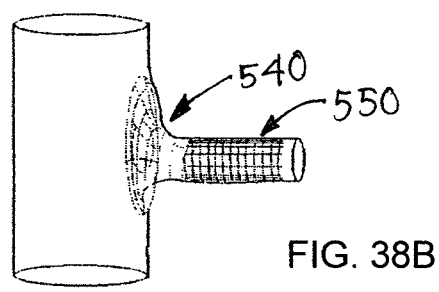
Figure 39A:
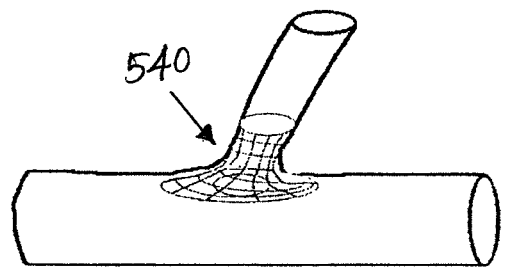
FIGS. 39A-39C are cross-sectional views of a bifurcation where a branch vessel extends from a main vessel, showing another method for treating the bifurcation using the rivet stent of FIG. 37.
Figure 39B:
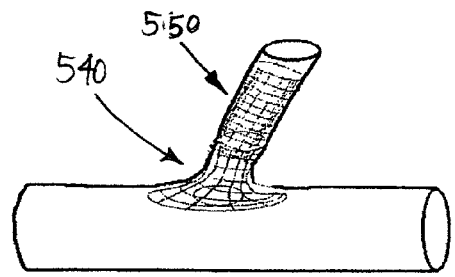
Figure 39C:
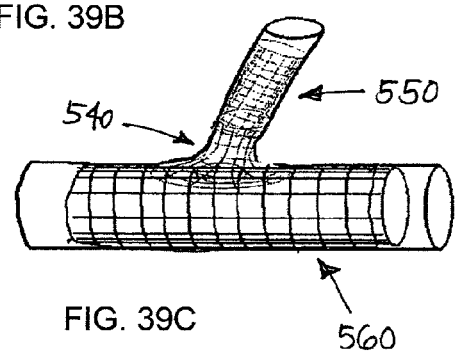

As shown in FIG. 38B, unlike previous embodiments, a separate stent 550 may be delivered into the branch lumen 94 beyond or overlapping the distal portion 543 of the stent 550. The additional stent may be any conventional uniform property stent or a variable property stent, similar to the distal portions of the stents described herein. FIGS. 39A-39C show another variation in which the stent 540 of FIG. 37 is delivered along with a first separate stent 550 in the branch lumen 94, e.g., similar to FIG. 38B, and a second separate stent 560 in the main lumen 92.

Figure 40:
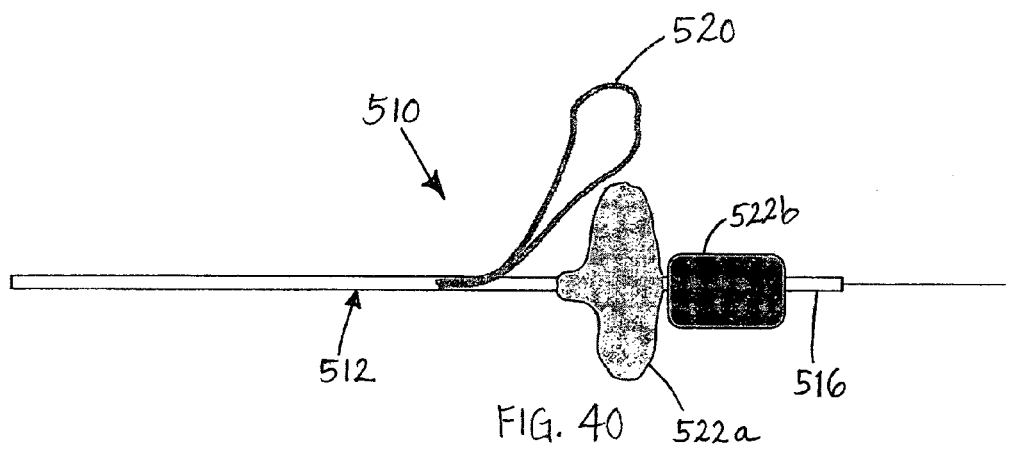
FIG. 40 is a side view of an exemplary apparatus for delivering a rivet stent, such as that shown in FIG. 37.

FIG. 40 shows an exemplary embodiment of a delivery apparatus 510 that may be used to deliver the stent 540 of FIG. 37 or other similar stent, either alone or with a separate branch lumen stent, such as the stent 550 shown in FIG. 38B. The apparatus 510 may include a locator device 520, e.g., such as those disclosed in the applications incorporated by reference above. In addition, the apparatus 510 may include one or more balloons, e.g., a larger proximal balloon 522a and a smaller distal balloon 522b, which may be inflated independently of one another to expand the stent 540 similar to other embodiments described elsewhere herein. For example, the proximal flaring portion 541 of the stent 540 may at least partially overly the proximal balloon 522a and the distal portion 543 may overly the distal balloon 522b.

Figure 41:
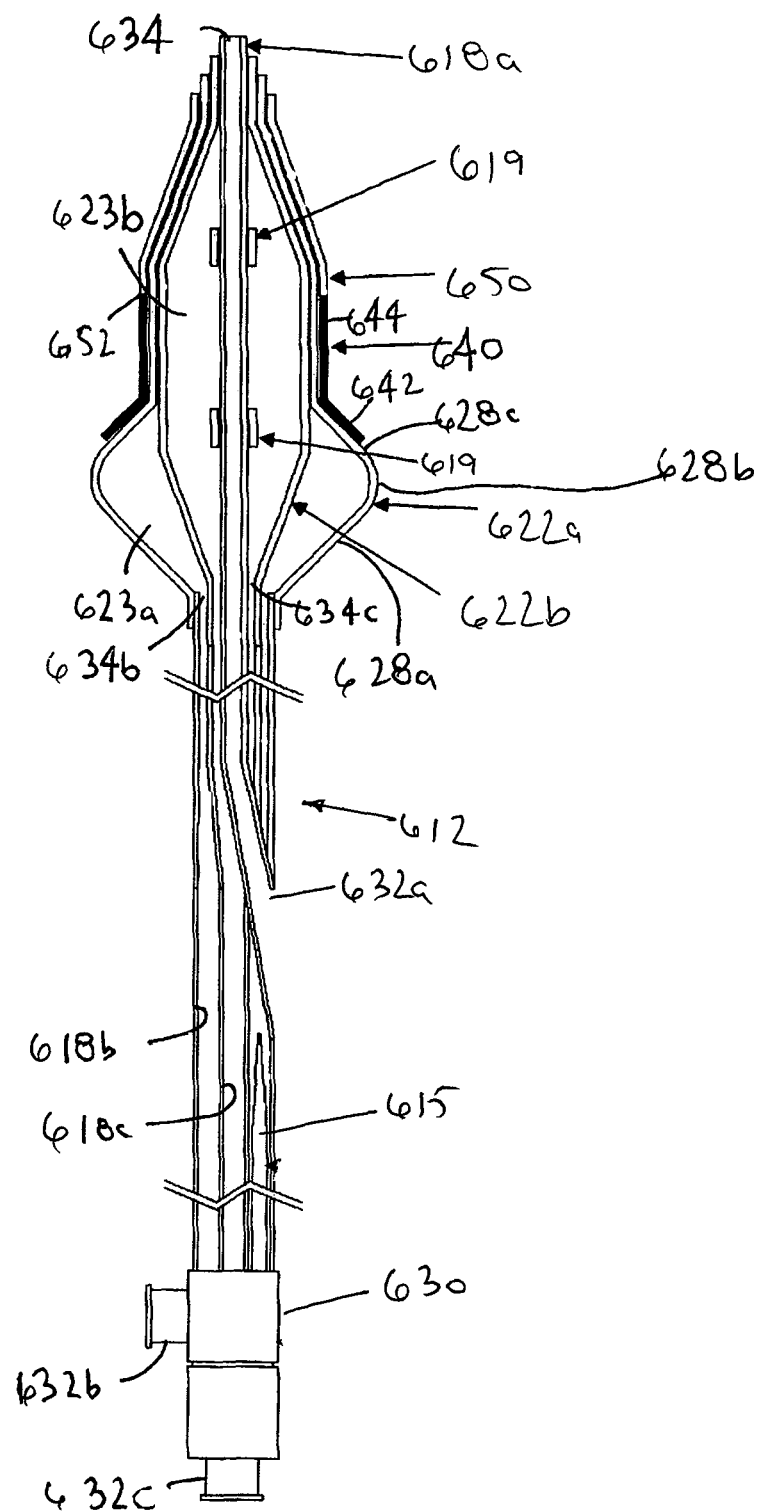
FIG. 41 is a cross-sectional side view of a delivery catheter including a distal end carrying a stent over a pair of balloons.
Figure 42:
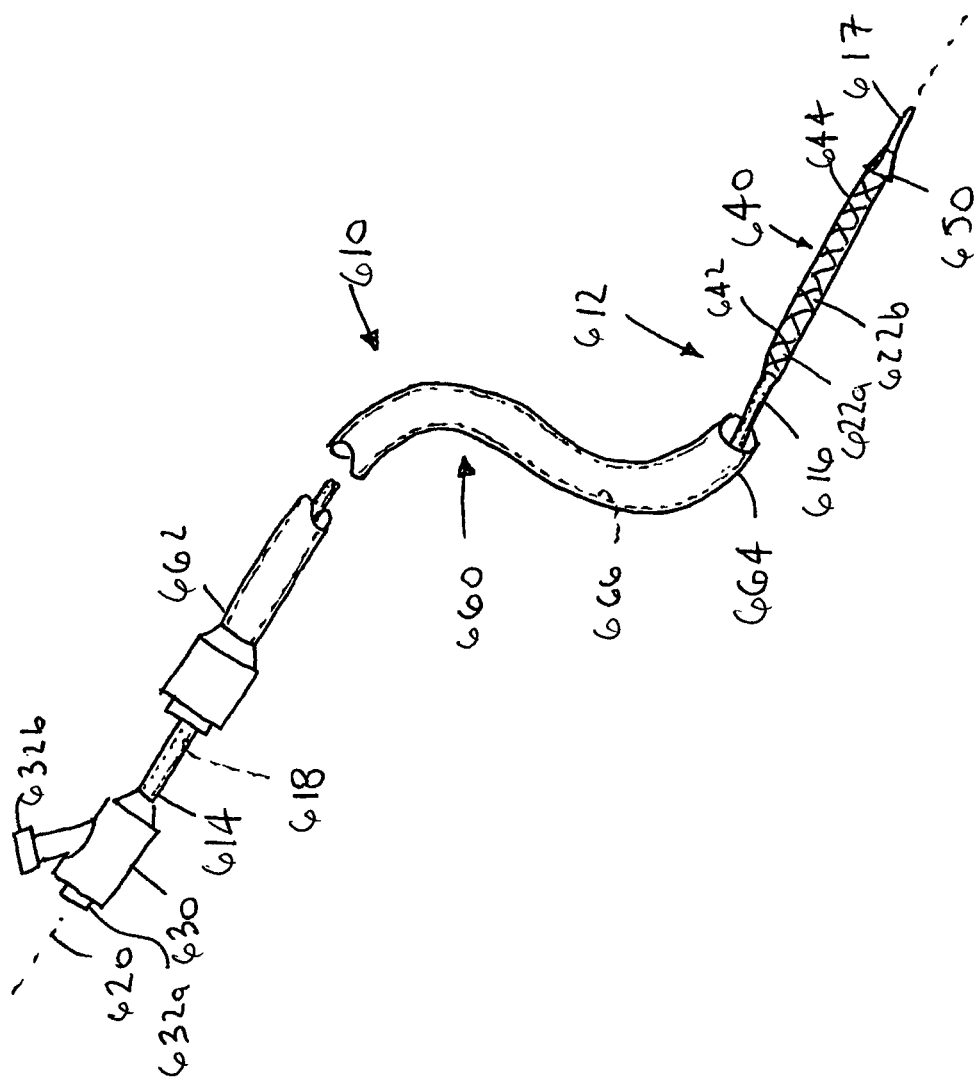
FIGS. 42 and 43 are perspective views of an apparatus for delivering a stent, including a guide catheter and the delivery catheter of FIG. 41, showing the balloons deflated and partially inflated, respectively, to expand the stent.
Figure 43:
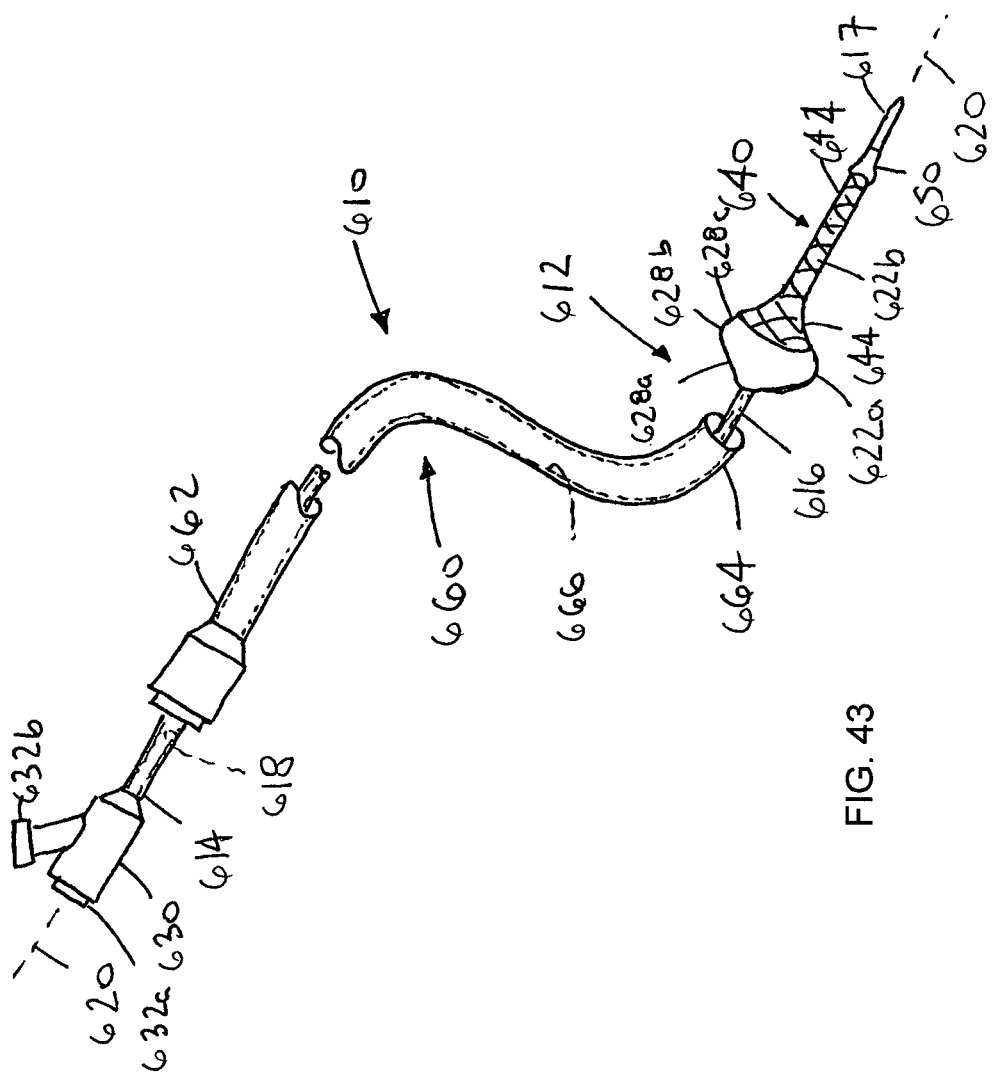

Turning to FIGS. 41-43, yet another exemplary embodiment of an apparatus 610 for delivering a stent or other prosthesis 640, e.g., into an ostium or other bifurcation between a main lumen and a branch lumen (not shown). Generally, the apparatus 610 includes a delivery catheter or other elongate tubular member 612 having a proximal end 614, a distal end 616, and one or more lumens 618 extending between the proximal and distal ends 614, 616, thereby defining a longitudinal axis 620 extending between the proximal and distal ends 614, 616.

As shown, the delivery catheter 612 may include one or more balloons or other expandable members 622 on the distal end 16 for expanding and/or deploying the stent 640, similar to other embodiments described herein. In addition, the distal end 616 may include one or more markers, e.g., one or more bands of radiopaque material 619 (two shown in FIG. 41), to facilitate positioning the delivery catheter 612 and/or stent 640. In addition or alternatively, the delivery catheter 612 may include one or more therapeutic and/or diagnostic elements (not shown) on the distal end 616, e.g., instead of or in addition to the stent 640 and/or balloon(s) 622.

Optionally, the delivery catheter 612 may include one or more locator elements (not shown) on the distal end 616, e.g., proximal or otherwise adjacent to the stent 640, such as those disclosed in applications Ser. No. 10/712,888, filed Nov. 12, 2003, and 60/722,182, filed Sep. 29, 2005 the entire disclosures of which are expressly incorporated by reference herein, and in application Ser. No. 11/419,997, incorporated by reference above.

The stent 640 may include a first or flaring portion 642 and a second or tubular portion 644. As shown, the first portion 642 is disposed proximal to the second portion 644, e.g., for antegrade delivery. Alternatively, the first and second portions 642, 644 may be reversed, e.g., for retrograde delivery, as may any of the other embodiments described herein. In this alternative, the orientation of the balloons 622 on the distal end 616 of the delivery catheter 612 (or other delivery device described herein) may be reversed from that described herein.

The stent 640 may be formed from a variety of materials that may be plastically deformed to allow expansion of the stent 640, e.g., similar to other embodiments described herein. Alternatively, at least a portion of the stent 640 may be self-expanding and/or the resistance of the stent 640 to expansion may be varied along its length, also similar to other embodiments described herein.

The stent 640 may be a generally tubular structure, e.g., including openings in a tubular wall that facilitate expansion of the stent 640 and/or allow tissue ingrowth. For example, the stent 640 may be an elongate tube that has slots or other openings formed in the tube wall, e.g., by laser cutting, mechanical cutting, chemical etching, machining, and the like. Alternatively, the stent 640 may be a braided or other structure, e.g., formed from one or wires or other filaments braided or otherwise wound in a desired manner. Additional possible stent structures may include helical coil wires or sheets, welding or otherwise attaching wire or other structures together, and the like. If desired, one or more portions of the stent 640 may include a membrane, film, or coating (not shown), e.g., to create a nonporous, partially porous, or porous surface between cells of the stent 640 and/or to carry one or more therapeutic compounds, similar to other embodiments described herein.

In addition, as shown in FIGS. 42 and 43, the apparatus 610 may include a guide catheter 660 including a proximal end 662, a distal end 664, and a lumen 666 extending therebetween. The distal end 664 may be sized and/or shaped to facilitate advancement into a patient's vasculature or other body lumen, as described further below. The lumen 666 may have sufficient size for receiving the distal end 616 of the delivery catheter 612 therethrough, e.g., with any locator elements (not shown) in a contracted condition. Optionally, the distal end 664 of the guide catheter 660 may be biased to a predetermined shape, e.g., a "J" shape, which may facilitate positioning the guide catheter 660 within or adjacent an ostium. The guide catheter 660 may be constructed from substantially flexible and/or floppy materials, e.g., plastic, having a braid or other reinforcement (not shown) that sufficiently supports the guide catheter 660 to prevent kinking or buckling, while allowing the guide catheter 660 to be directed easily through tortuous anatomy.

Optionally, the apparatus 610 may include other components to provide a system or kit for delivering the stent 640, e.g., a sheath that may be advanced over and/or retracted from the distal end 616 of the delivery catheter 612, one or more syringes or other sources of inflation media and/or vacuum, tubing, and/or one or more guidewires (all not shown).

Returning to FIGS. 41-43, the delivery catheter 612 may be formed from one or more tubular bodies, e.g., having variable flexibility along its length. For example, similar to other embodiments described herein, the distal end 616 may be substantially flexible to facilitate insertion through tortuous anatomy, e.g., terminating in a rounded, tapered, and/or other substantially atraumatic distal tip 617. The distal end 616 may be sized and/or shaped for introduction into a body lumen, e.g., having a diameter between about one and seven millimeters (1-7 mm), or less than 1.5 millimeters. The proximal end 614 may be substantially flexible or semi-rigid, e.g., having sufficient column strength to facilitate advancing the distal end 16 through a patient's vasculature by pushing on the proximal end 614. Optionally, as shown in FIG. 41, a shaft support wire or other stiffener 615 may be provided within the proximal end 614, e.g., to facilitate pushing the delivery catheter 12 from the proximal end 14. The delivery catheter 612 may be formed from plastic, metal, or composite materials, e.g., a plastic material having a wire, braid, or coil core, which may preventing kinking or buckling of the delivery catheter 612 during advancement.

As shown, the delivery catheter 612 may include a handle 630 on the proximal end 614, e.g., to facilitate manipulating the delivery catheter 612, which may be included in the other embodiments described herein. The handle 630 may include one or more ports 632 communicating with respective lumens 618 within the delivery catheter 612. The handle 630 may be molded, machined, or otherwise formed from plastic, metal, or composite material, e.g., providing an outer casing, which may be contoured or otherwise shaped to ease manipulation. The proximal end 614 of the delivery catheter 612 may be attached to the handle 630, e.g., by bonding, cooperating connectors, interference fit, and the like. Optionally, if the apparatus 610 includes any actuatable components (not shown) on the distal end 616, the handle 630 may include one or more actuators (not shown), such as one or more slides, dials, buttons, and the like, for actuating or otherwise manipulating the components from the proximal end 614.

As best seen in FIG. 41, the catheter 612 includes at least three lumens 618 extending between the proximal and distal ends 614, 616. For example, the catheter 612 may include an instrument lumen 618a that extends from a side port 632a to an opening 634 in the distal tip 617. The instrument lumen 618a may have sufficient size to allow a guidewire or other rail or instrument (not shown) to be inserted therethrough, e.g., to facilitate advancing the catheter 612 over the rail, as explained further below. Alternatively, rather than a "rapid exchange" instrument lumen 618a, an instrument lumen (not shown) may be provided that extends from the distal end 616 to the handle 630. In this alternative, the handle 630 may include a port (not shown) and/or one or more seals (also not shown) that prevent fluid, e.g., blood, from flowing proximally out of the port, yet allows one or more instruments to be inserted therethrough and into the instrument lumen 618a.

In addition, the catheter 612 may include inflation lumens 618b, 618c that extend from respective side ports 632b, 632c in the handle 630 through the catheter 612 to openings 634b, 634c on the distal end 616. Each opening 634b, 634c communicates within an interior 623a, 623b of a respective balloon 622a, 622b. The side ports 632b, 632c on the handle 630 may include connectors, e.g., a luer lock connector (not shown), one or more seals (also not shown), and the like. A source of inflation media and/or vacuum, e.g., a syringe filled with saline (not shown), may be connected to the side ports 632b, 632c, e.g., via tubing (also not shown), for expanding and/or collapsing the balloons 622a, 622b.

As shown in FIG. 41, the lumens 618 are disposed adjacent one another. Alternatively, the lumens 618 may be disposed in concentric or other arrangements within the body of the catheter 612. In addition, if the apparatus 610 includes additional balloons (not shown) on the distal end 616, the catheter 612 may include one or more additional inflation lumens (also not shown), and the handle 630 may include one or more additional ports (also not shown), similar to those shown and described with reference to FIG. 41.

Alternatively, other configurations of lumens may be provided for delivering fluid to and/or aspirating fluid from one or both balloons 622. For example, a single lumen may be provided (not shown) that communicates with the interiors 623 of both balloons 622. This embodiment may allow the balloons 622 to be expanded and/or collapsed substantially simultaneously using a single syringe or other source of fluid/vacuum. In another alternative, the catheter 612 may include separate inflation lumens 618b, 618c, but the handle 630 may include a single side port (not shown) to which a syringe or other source of fluid/vacuum may be connected. In this alternative, the handle 630 may include a switch, stopcock, valve, or other device for selectively connecting one or both inflation lumens 618b, 618c to the side port.

For example, a three-way valve (not shown) may be directed to first or second positions to allow the side port to be connected to either of the inflation lumens 615b, 618c, e.g., for inflating/collapsing an individual balloon 622a, 622b. In a third position, the side port may be connected to both lumens 618b, 618c for inflating/collapsing both balloons 622 simultaneously. This configuration may be particularly useful for quickly collapsing both balloons 622 after implanting the stent 640 before removing the apparatus 610. In addition, the configuration may facilitate expanding the entire stent 640, e.g., after expanding and anchoring the first portion 642 and/or after flaring the second portion 644.

Returning to FIGS. 41-43, the delivery catheter 612 includes an outer or proximal balloon 622a and an inner or distal balloon 622b on the distal end 616. As shown, the first portion 642 of the stent 640 is disposed over a portion of the proximal balloon 622a, and the second portion 644 of the stent 640 is disposed over at least a portion of the distal balloon 622b. Alternatively, the delivery catheter 612 may include a single or multiple balloons (not shown) on the distal end 616 over which the stent 640 may be placed. Additional information on balloon catheters and methods for using them are disclosed in the applications incorporated by reference herein.

The balloons 622 may be bonded or otherwise secured to the distal end 16 of the delivery catheter 612. For example, ends of the balloons 622 may be attached to the distal end 616 by bonding with an adhesive, by sonic welding, using an annular collar or sleeve, and the like. The distal balloon 622b may include a proximal end 624a attached to the distal end 616 of the catheter 612 proximal to opening 634c and a distal end 626a attached adjacent the distal tip 617. The proximal balloon 622a may extend at least partially over the distal balloon 622b. For example, the distal end of the proximal balloon 622a may extend entirely over the distal balloon 622b and be attached over or adjacent to the distal end of the distal balloon 622b, e.g., by bonding, sonic welding, and the like, as described elsewhere herein.

The distal balloon 622b may be expandable from a contracted condition (shown in FIG. 42) to an enlarged condition (shown in FIG. 41). Similarly, the proximal balloon 622a may also be expandable from a contracted condition (shown in FIG. 42) to an enlarged condition (shown in FIGS. 41 and 43). As shown, the proximal balloon 622a and distal balloon 622b may be expandable independently from one another.

With particular reference to FIG. 41, in the enlarged condition, the proximal balloon 622a may include proximal and distal ramped surfaces 628a, 628c meeting at an outermost intermediate region 628b. As shown, the intermediate region 628b is disposed proximal to the stent 640 such that the distal surface 628b extends beneath the first portion 642 of the stent 640, e.g., for flaring the first portion 642, and proximally beyond the first portion 642, e.g., for facilitating positioning the stent 640, as described further below.

The balloons 622 may be formed from substantially inelastic material, e.g., PET, nylon, or PEBAX, such that each balloon 622 expands to a predetermined size in its enlarged condition once sufficient fluid is introduced into the interior of the balloon 622. Alternatively, the balloon 622 may be formed from substantially elastic material, e.g., silicone, polyurethane, or polyethylene, such that the balloon 622 may be expanded to a variety of sizes depending upon the volume and/or pressure of fluid within the interior.

Optionally, the delivery catheter 612 may include a stop 650 disposed adjacent the second portion 644 of the stent 640. As shown in FIG. 41, the stop 650 may be a section of tubular material formed, bonded, or otherwise attached over a portion of the balloons 622. The stop 650 may include a substantially blunt proximal edge 652 adjacent the stent 640, which may abut the second portion 644 of the stent 640, e.g., to prevent distal migration of the stent 640 when the first portion 642 of the stent 640 is flared, as described further below. In addition or alternatively, a sleeve (not shown) may extend from the stop 650, e.g., to partially cover the distal end 644 of the stent 644, e.g., to prevent the distal end 644 from dislodging and passing over the stop 650. Alternatively, other structures (not shown) may be provided to constrain, secure, or otherwise limit distal migration of the stent 40, such as the sleeves disclosed in application Ser. No. 136,266, incorporated by reference above.

Turning to FIGS. 44-48, an exemplary method is shown for using the apparatus 610 (which may be any of the embodiments described herein) to deliver a stent 640 into an ostium 90. The ostium 90 may be an opening in a wall of a first or main body lumen or trunk 92 that communicates with a second body lumen or branch 94, such as those described elsewhere herein. An occlusion or other lesion 96 may exist at and/or adjacent to the ostium 90, e.g., extending at least partially into the branch 94. The lesion 96 may include atherosclerotic plaque or other material that partially or completely occludes blood or other fluid flow between the trunk 92 and the branch 94.

Figure 44:
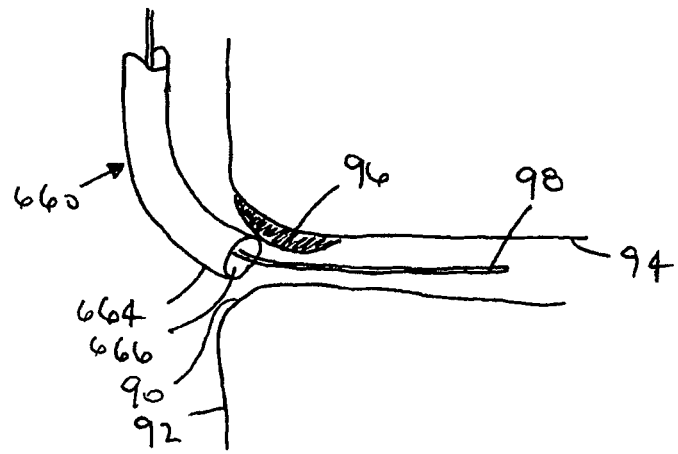
FIGS. 44-51 are cross-sectional views of a patient's body, showing a method for positioning and/or delivering a stent within an ostium of a body lumen using the apparatus of FIGS. 41-43.

Initially, as shown in FIG. 44, a guidewire 98 or other rail may be introduced from the trunk 92 through the ostium 90 into the branch 94. As shown, the lesion 96 at the ostium 90 partially occludes the ostium 90 and extends into the branch 94. The guidewire 98 may be placed using conventional methods. For example, a percutaneous puncture or cut-down may be created at a peripheral location (not shown), such as a femoral artery, carotid artery, or other entry site, and the guidewire 98 may be advanced through the patient's vasculature from the entry site, e.g., alone or with the aid of guide catheter 660. If the lesion 96 completely occludes the branch 94, the guidewire 98 may be directed through the occlusion, or other devices (not shown) may be advanced over the guidewire 98 or otherwise in conjunction with the guidewire 98 to create a passage through the lesion 96 for the guidewire 98.

After the guidewire 98 is directed into the branch 94 beyond the lesion 96, it may be desirable to at least partially dilate the lesion 96. For example, an angioplasty catheter (not shown) may be advanced through the guide catheter 660 and/or over the guidewire 98 into and through the lesion 96, whereupon a balloon or other element on the catheter may be expanded to at least partially dilate the lesion 96. If desired, other procedures may also be performed at the lesion 96, e.g., to soften, remove, or otherwise treat plaque or other material forming the lesion 96, before the stent 640 is implanted. After completing any such procedures, any instruments advanced over the guidewire 98 may be removed.

As shown in FIG. 44, the distal end 664 of the guide catheter 660 has been advanced over the guidewire 98 into the trunk 92, e.g., until the distal end 664 is disposed adjacent or proximal to the ostium 90. The guide catheter 660 may be used to advance one or more instruments (such as those just described) over the guidewire 98 and into the trunk 92 and/or branch 94.

Figure 45:
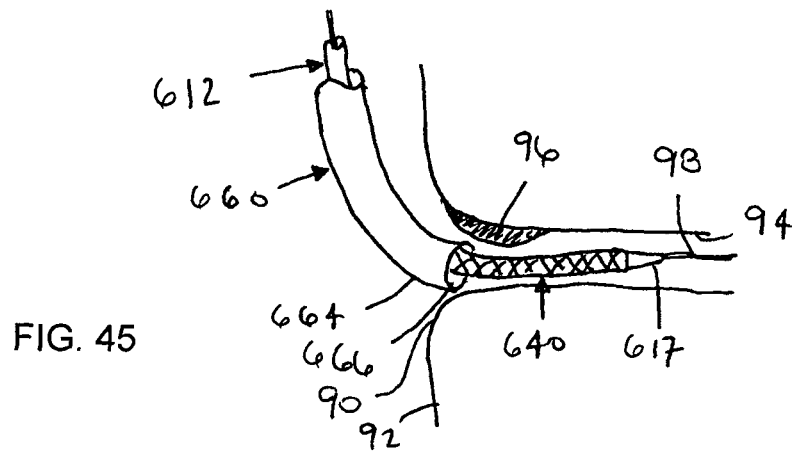
Figure 46:
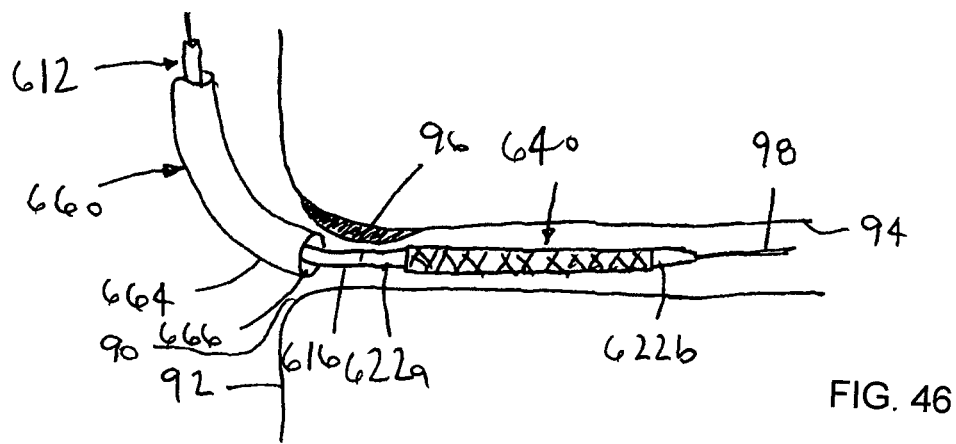

Turning to FIG. 45, to deliver the stent 640, the distal end 616 of the delivery catheter 612 may be advanced over the guidewire 98 and through the lumen 666 of the guide catheter 660 from the entry site into the trunk 92. As shown, the stent 640 and balloons 622 are in their contracted conditions during advancement. With the distal end 664 of the guide catheter 660 against or adjacent the ostium 90, the distal end 616 of the delivery catheter 612 may be advanced from the guide catheter 660, through the ostium 90, and into the branch 94. For example, as shown in FIG. 46, the delivery catheter 612 may be advanced until the stent 640 extends into and through the lesion 96, e.g., to ensure that the stent 640 may be positioned fully within the lesion 96 before any portion of the stent 640 is expanded.

Figure 47:
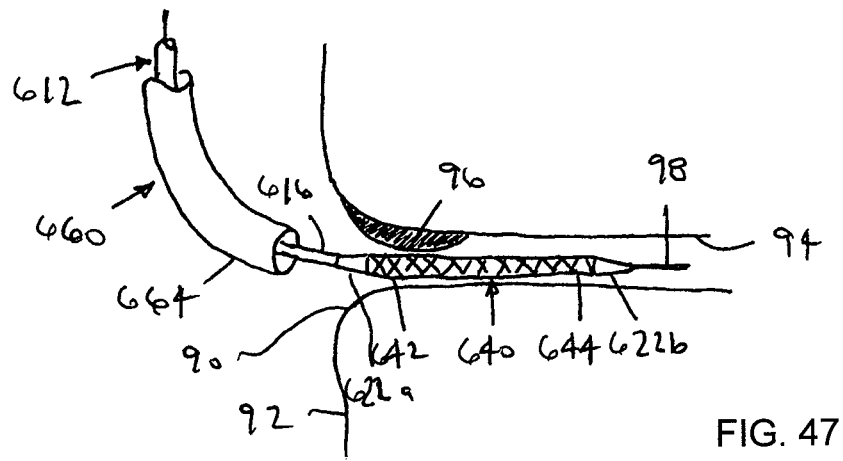

Turning to FIG. 47, the delivery catheter 612 may be partially withdrawn (or otherwise positioned) to dispose the stent 640 within the lesion 96, e.g., such that the first portion 642 of the stent 640 is positioned adjacent the ostium 90 within the branch 94. To facilitate positioning, the delivery catheter 612 may be monitored using fluoroscopy or other external imaging, e.g., to observe and monitor markers 619 (not shown, see FIG. 41) on the distal end 616. In addition, if desired, the guide catheter 660 may be partially withdrawn into the trunk 92 such that the guide catheter 660 does not interfere with movement of the distal end 616 of the delivery catheter 612.

Figure 48:
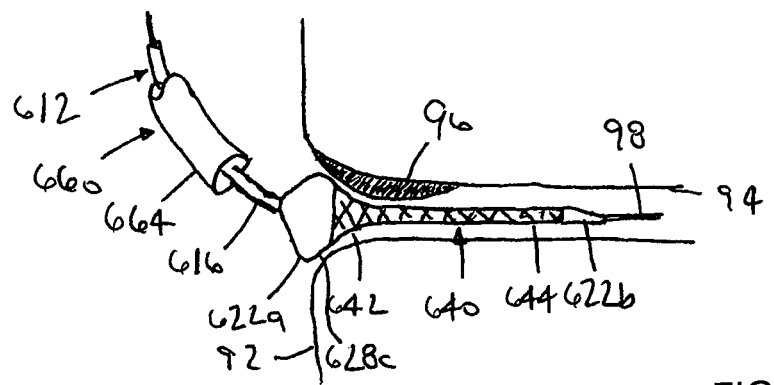

Turning to FIG. 48, with the delivery catheter 612 and stent 640 property positioned, the proximal balloon 622a may be expanded, e.g., by delivering saline, nitrogen, or other inflation media into the interior 623a (not shown, see FIG. 41) of the proximal balloon 622a from a syringe or other fluid source (not shown) coupled to the proximal end (also not shown) of the delivery catheter 612. As the proximal balloon 622b is expanded, the first portion 642 of the stent 640 is expanded, e.g., into a flared configuration conforming to the distal surface 628c of the proximal balloon 622a.

Figure 49:
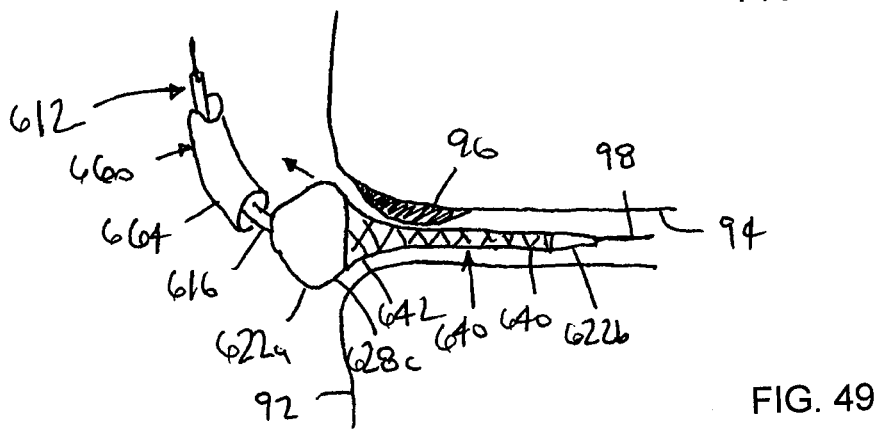

As shown in FIG. 49, as the proximal balloon 622a is expanded, the distal surface 628c of the proximal balloon 622a beyond the stent 640 may contact the branch 94 adjacent the ostium 90. Because of the tapered or ramped shape of the distal surface 628c, the radial expansion of the proximal balloon 622a may translate into a proximal force, causing the distal end 616 of the delivery catheter, and consequently the stent 640, to move proximally. Stated differently, as the proximal balloon 622a is expanded, the stent 640 may migrate partially out of the branch 94, e.g., such that the first portion 642 is disposed within the ostium 90. Thus, if the stent 640 is positioned distally further into the branch 94 than desired (e.g., despite monitoring using fluoroscopy), the proximal balloon 622a may automatically correct the position of the stent 640 within the ostium 90. Optionally, at least the distal surface 628c of the proximal balloon 622a may be formed from a lubricious material and/or may include a lubricious coating, e.g., to reduce friction between the distal surface 628c and the wall of the branch 94 to facilitate migration and/or other automatic correction in positioning of the stent 640.

Figure 50:
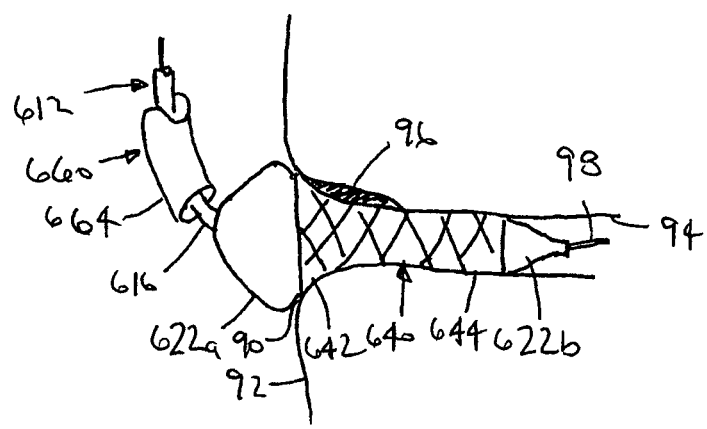

Turning to FIG. 50, after inflating the proximal balloon 622a, the distal balloon 622b may be inflated to expand the stent 640 fully. With the distal balloon 622b disposed within the proximal balloon 622a, as shown in FIG. 41, the distal balloon 622b may cause the proximal balloon 622a, and consequently the first portion 642 of the stent 640, to expand further. Thus, the distal balloon 622b may expand the second portion 644 of the stent 640 within the branch 94, while simultaneously enhancing the proximal balloon 622a further expanding and/or flaring the first portion 642 of the stent 640 to contact the wall of the ostium 90. In addition or alternatively, the proximal balloon 622a may be inflated further to flare and/or expand the first portion 642 of the stent 640 such that the first portion 642 contacts and/or dilates the ostium 90. As the stent 640 expands, the lesion 96 may be directed radially outwardly, thereby dilating the ostium 90 and/or branch 94. Optionally, if desired, distal force may be applied to the delivery catheter 612 to direct the first portion 642 of the stent 640 against the ostium 90, e.g., to enhance securing the stent 640 and/or conforming the first portion 642 of the stent 640 to the shape of the ostium 90.

Figure 51:
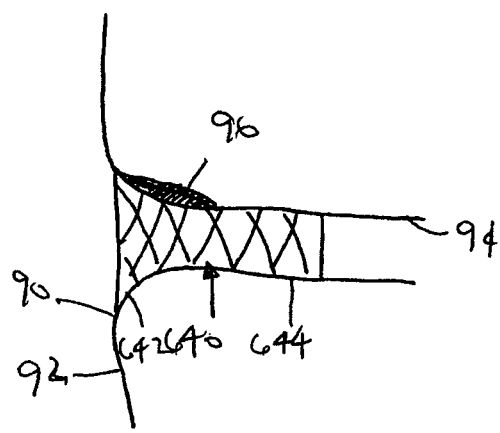

Turning to FIG. 51, with the stent 640 fully deployed, the balloons 622 may be deflated or otherwise collapsed, and the delivery catheter 612 may be withdrawn into the guide catheter 660. Optionally, the guide catheter 660 may be advanced towards or against the ostium 90 and/or against a proximal end of the stent 640 before the delivery catheter 612 is removed. This action may facilitate withdrawing the distal end 616 (and the balloons 622) back through the stent 640, e.g., without substantial risk of dislodging the stent 640 from the ostium 90 and/or branch 94. The delivery catheter 612, guide catheter 660, and/or guidewire 98 may then be removed from the patient's body, leaving the stent 640 in place.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. An apparatus for treating an ostium communicating between a main body lumen and a branch body lumen, comprising:

an elongate member comprising a proximal end, a distal end sized for introduction into the main body lumen and the branch body lumen;

a first expandable member formed from substantially compliant material on the distal end, the first expandable member being expandable from a collapsed configuration to a substantially spherical expanded configuration;

a second expandable member formed from substantially non-compliant material on the distal end adjacent the first expandable member, the second expandable member being expandable from a collapsed configuration to a substantially cylindrical expanded configuration; and a stent on the distal end over the first and second expandable members, the stent comprising a first flaring portion overlying a portion of the first expandable member, and a second main portion comprising a distal main portion overlying the second expandable member, and a proximal main portion connecting the first flaring portion to the distal main portion, the proximal main portion overlying a transition between the first and second expandable members;

the first and second expandable members being independently expandable such that, when the first expandable member is expanded, the first flaring portion of the stent is expanded to a flared condition while the second expandable member remains in the collapsed configuration, and when the second expandable member is subsequently expanded, the second main portion is expanded radially outwardly and the first flaring portion is further expanded radially outwardly, wherein the first flaring portion of the stent comprises:

a first set of cells disposed at the first end;

a second set of cells including first ends coupled to the first set of cells and second ends opposite the first ends, and a plurality of flexible connectors coupled to the second ends of the second set of cells to connect the second set of cells to the second portion of the stent, wherein the second set of cells comprises struts connected to curved segments, the curved segments having a lower yield strength than the struts.

2. The apparatus of claim 1, wherein the proximal main portion has a greater stiffness than the first flaring portion such that the proximal main portion resists expansion when the first expandable member is expanded.

3. The apparatus of claim 1, wherein the proximal main portion has a greater radial strength than the distal main portion, and the distal main portion has a greater radial strength than the first flaring portion.

4. The apparatus of claim 1, wherein the first and second expandable members require respective inflation pressures to expand to the expanded configuration, and wherein the inflation pressure of the first expandable member is less than the inflation pressure of the second expandable member.

5. The apparatus of claim 1, wherein the first expandable member is expandable independently of the second expandable member using an inflation pressure that is less than an inflation pressure necessary to expand the second expandable member.

6. The apparatus of claim 1, wherein the struts are directed from a generally axial orientation towards a generally radially outward orientation when the first expandable member is expanded.

7. The apparatus of claim 1, wherein the struts are directed from the generally radially outward orientation in the flared condition towards a circumferential orientation when the second expandable member is expanded.

8. The apparatus of claim 1, the first set of cells comprising struts that extend substantially axially when the stent is in a contracted condition, the first end portion flaring such that the struts are directed towards a circumferential orientation in the flared condition.

9. The apparatus of claim 1, wherein the connectors comprise curvilinear segments having a thickness and a width, at least one of the thickness and the width being thinner than segments comprising the first end portion.

10. The apparatus of claim 1, further comprising a source of inflation media communicating with an interior of the first expandable member for delivering first and second predetermined volumes into the first expandable member to partially and fully expand the first expandable member, respectively.

11. The apparatus of claim 10, wherein the source of inflation media comprises a syringe comprising a barrel including inflation media therein and a plunger, the barrel comprising first and second markers such that, when the plunger is depressed successively to the first and second markers, the first and second predetermined volumes are delivered into the interior of the first expandable member, respectively.

12. The apparatus of claim 1, wherein the first expandable member comprises a distal portion that extends distally from a substantially spherical portion at least partially over the second expandable member.

13. The apparatus of claim 3, wherein the radial strength of the second main portion decreases from the proximal main portion to the distal main portion.

\* \* \* \* \*